(12) United States Patent
Fan et al.

(10) Patent No.: US 10,035,768 B2
(45) Date of Patent: Jul. 31, 2018

(54) C5AR ANTAGONISTS

(71) Applicant: CHEMOCENTRYX, INC., Mountain View, CA (US)

(72) Inventors: Pingchen Fan, Fremont, CA (US); Kevin Lloyd Greenman, Sunnyvale, CA (US); Manmohan Reddy Leleti, West San Jose, CA (US); Yandong Li, San Diego, CA (US); Jay Powers, Pacifica, CA (US); Hiroko Tanaka, Mountain View, CA (US); Ju Yang, Palo Alto, CA (US); Yibin Zeng, Foster City, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 15/722,819

(22) Filed: Oct. 2, 2017

(65) Prior Publication Data

US 2018/0179160 A1   Jun. 28, 2018

Related U.S. Application Data

(63) Continuation of application No. 15/400,820, filed on Jan. 6, 2017, which is a continuation of application No. 14/846,487, filed on Sep. 4, 2015, now Pat. No. 9,573,897, which is a continuation of application No. 13/806,339, filed as application No. PCT/US2011/041910 on Jun. 24, 2011, now Pat. No. 9,126,939, which is a continuation of application No. 13/072,616, filed on Mar. 25, 2011, and a continuation of application No. 12/823,039, filed on Jun. 24, 2010.

(51) Int. Cl.
| | |
|---|---|
| *C07D 211/60* | (2006.01) |
| *C07D 413/12* | (2006.01) |
| *C07D 405/10* | (2006.01) |
| *C07D 401/12* | (2006.01) |
| *C07D 401/10* | (2006.01) |
| *C07D 401/06* | (2006.01) |
| *A61K 31/5377* | (2006.01) |
| *A61K 31/4545* | (2006.01) |
| *A61K 31/454* | (2006.01) |
| *A61K 31/451* | (2006.01) |
| *A61K 31/445* | (2006.01) |
| *C07D 413/14* | (2006.01) |
| *C07D 401/14* | (2006.01) |
| *C07D 405/12* | (2006.01) |

(52) U.S. Cl.
CPC ......... *C07D 211/60* (2013.01); *A61K 31/445* (2013.01); *A61K 31/451* (2013.01); *A61K 31/454* (2013.01); *A61K 31/4545* (2013.01); *A61K 31/5377* (2013.01); *C07D 401/06* (2013.01); *C07D 401/10* (2013.01); *C07D 401/12* (2013.01); *C07D 401/14* (2013.01); *C07D 405/10* (2013.01); *C07D 405/12* (2013.01); *C07D 413/12* (2013.01); *C07D 413/14* (2013.01)

(58) Field of Classification Search
CPC ........................... C07D 211/56; C07D 213/02
USPC ........................................................ 546/192
See application file for complete search history.

(56) References Cited

U.S. PATENT DOCUMENTS

| | | |
|---|---|---|
| 4,686,100 A | 8/1987 | Raffin et al. |
| 6,713,502 B2 | 3/2004 | Dhanak et al. |
| 7,105,567 B2 | 9/2006 | Ishibuchi et al. |
| 7,169,775 B2 | 1/2007 | Thurkauf et al. |
| 7,455,837 B2 | 11/2008 | Guo et al. |
| 7,635,698 B2 | 12/2009 | Rosse et al. |
| 7,834,035 B2 | 11/2010 | Bessis et al. |
| 8,007,767 B2 | 8/2011 | Thurkauf et al. |
| 8,026,367 B2 | 9/2011 | Allegretti et al. |
| 8,198,454 B2 | 6/2012 | Nakamura et al. |
| 8,206,716 B2 | 6/2012 | Fung et al. |
| 8,372,404 B2 | 2/2013 | Fung et al. |
| 8,445,515 B2 | 5/2013 | Fan et al. |
| 8,906,938 B2 | 12/2014 | Fan et al. |
| 9,126,939 B2 | 9/2015 | Fan et al. |
| 9,573,897 B2 | 2/2017 | Fan et al. |
| 9,745,268 B2 | 8/2017 | Fan et al. |
| 2003/0195192 A1 | 10/2003 | Haviv et al. |
| 2003/0195195 A1 | 10/2003 | Haviv et al. |
| 2004/0014744 A1 | 1/2004 | Haviv et al. |
| 2004/0014782 A1 | 1/2004 | Krause |
| 2004/0166988 A1 | 8/2004 | Zimmermann et al. |
| 2006/0004049 A1 | 1/2006 | Yao et al. |
| 2006/0019995 A1 | 1/2006 | Rault et al. |
| 2006/0030557 A1 | 2/2006 | Haviv et al. |

(Continued)

FOREIGN PATENT DOCUMENTS

| | | |
|---|---|---|
| JP | 5819730 B2 | 6/2012 |
| WO | 00/12074 A2 | 3/2000 |

(Continued)

OTHER PUBLICATIONS

Extended European Search Report corresponding to EP 09835688.4 (PCT/US2009/068941) dated Aug. 2, 2012, 5 pages.

(Continued)

*Primary Examiner* — Rita J Desai
(74) *Attorney, Agent, or Firm* — Mintz Levin Cohn Ferris Glovsky and Popeo PC

(57) ABSTRACT

Compounds are provided that are modulators of the C5a receptor. The compounds are substituted piperidines and are useful in pharmaceutical compositions, methods for the treatment of diseases and disorders involving the pathologic activation of C5a receptors.

10 Claims, 69 Drawing Sheets

(56) References Cited

U.S. PATENT DOCUMENTS

| | | |
|---|---|---|
| 2006/0154917 A1 | 7/2006 | Zhang et al. |
| 2007/0117802 A1 | 5/2007 | Borzilleri et al. |
| 2010/0074863 A1 | 3/2010 | Or et al. |
| 2010/0104558 A1 | 4/2010 | Tharaux et al. |
| 2010/0179150 A1 | 7/2010 | Basarab et al. |
| 2010/0190824 A1 | 7/2010 | Kumar et al. |
| 2010/0311753 A1 | 12/2010 | Fan et al. |
| 2011/0275639 A1 | 11/2011 | Fan et al. |
| 2012/0225056 A1 | 9/2012 | Rother et al. |
| 2013/0317028 A1 | 11/2013 | Fan et al. |
| 2015/0126492 A1 | 5/2015 | Dechantsreiter et al. |
| 2015/0141425 A1 | 5/2015 | Fan et al. |
| 2017/0065604 A1 | 3/2017 | Fan et al. |
| 2017/0114017 A1 | 4/2017 | Fan et al. |
| 2017/0202821 A1 | 7/2017 | Bekker |

FOREIGN PATENT DOCUMENTS

| | | |
|---|---|---|
| WO | 00/12074 A3 | 3/2000 |
| WO | 02/29187 A1 | 4/2002 |
| WO | 02/049993 A2 | 6/2002 |
| WO | 02/049993 A3 | 6/2002 |
| WO | 03/008828 A1 | 1/2003 |
| WO | 03/082826 A1 | 10/2003 |
| WO | 03/084524 A1 | 10/2003 |
| WO | 2004/018460 A1 | 3/2004 |
| WO | 2004/043925 A2 | 5/2004 |
| WO | 2004/043925 A3 | 5/2004 |
| WO | 2004/100975 A1 | 11/2004 |
| WO | 2005/007087 A2 | 1/2005 |
| WO | 2005/007087 A3 | 1/2005 |
| WO | 2006/012226 A2 | 2/2006 |
| WO | 2006/012226 A3 | 2/2006 |
| WO | 2007/051062 A2 | 5/2007 |
| WO | 2007/051062 A3 | 5/2007 |
| WO | 2008/022060 A2 | 2/2008 |
| WO | 2008/022060 A3 | 2/2008 |
| WO | 2010/019210 A2 | 2/2010 |
| WO | 2010/019210 A3 | 2/2010 |
| WO | 2010/025510 A1 | 3/2010 |
| WO | 2010/075257 | 7/2010 |
| WO | 2011/035143 A2 | 3/2011 |
| WO | 2011/163640 A1 | 12/2011 |

OTHER PUBLICATIONS

Extended European Search Report corresponding to EP 11799027.5 (PCT/US2011/041910) dated Dec. 18, 2013, 4 pages.
Extended European Search Report corresponding to EP 16167779.4 dated Jun. 30, 2016; 6 pages.
International Search Report corresponding to PCT/US2009/068941 dated Mar. 5, 2010; 1 page.
International Preliminary Report on Patentability corresponding to PCT/US2009/068941 dated Jun. 29, 2011, 8 pages.
International Search Report corresponding to PCT/US2011/041910 dated Nov. 15, 2011, 1 page.
International Preliminary Report on Patentability corresponding to PCT/US2011/041910 dated Dec. 28, 2012, 8 pages.
International Search Report and Written Opinion corresponding to PCT Application No. PCT/US2015/052697 dated Jan. 7, 2016, 8 pages.
International Preliminary Report on Patentability corresponding to PCT/US2015/052697 dated Apr. 13, 2017, 6 pages.
International Search Report and Written Opinion corresponding to PCT/US2017/013132 dated Apr 7, 2017; 10 pages.
Abdellatif, A. A. et al., "True vasculitis in lupus nephritis," *Clinical Nephrology* (Jan. 22, 2010), 74(2): 106-112.
Aboab et al., "Emerging drugs for the treatment of sepsis," Exp. Opin. Emerg. Drugs., 2006, vol. 11(1), pp. 7-22.
Allegretti, Marcello et al., "Allosteric Modulation of Chemoattractant Receptors," *Frontiers in Immunology* (May 2, 2016); vol. 7, Article 170; 9 pages.
Ayala et al., "Differential induction of apoptosis in lymphoid tissues during sepsis: variation in onset, frequency and the nature of the mediators," Blood, 1996, 87:4261-4275.
Bao et al., "C5a promotes development of experimental lupus nephritis which can be blocked with a specific receptor antagonist," *Eur. J. Immunol.* (Accepted Jun. 20, 2005); 35:2496-2506.
Bekker, Pirow et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," *PLOS One* [DOI:10.1371/journal.pone.0164646 (Oct. 21, 2016); 19 pages.
Blagg et al., "Small, non-peptide C5a receptor antagonists: Part 1," Bioorganic & Medicinal Chemistry Letters, 2008, vol. 18, pp. 5601-5604.
Braga et al., "Making crystals from crystals: a green route to crystal engineering and polymorphism," 2005, The Journal of the Royal Society of Chemistry, Chem. Commun., 2005, pp. 3635-3645.
Brodbeck; Robbin M. et al., "Identification and Characterization of NDT 9513727 [N,N-bis(1,3-Benzodioxol-5-ylmethyl)-1-butyl-2,4-diphenyl-1H-imidazole-5-methanamine], a Novel, Orally Bioavailable C5a Receptor Inverse Agonist," *The Journal of Pharmacology and Experimental Therapeutics* (2008; accepted Aug. 26, 2008); 327(3):898-909.
Chemcats (AN) 0078873838 (2011).
ChemiCool "rotamer," 2012, p. 1.
Chronic-Obstructive-Pulmonary disease (COPD), Treatment Overview, www.webmd.com/lung/copd/tc/chronic-obstructive-pulmonary-disease-copd-treatme . . . p. 1-2, retrieved Apr. 22, 2014.
Cravedi et al., "Immune Cell-Derived C3a and C5a Costimulate Human T Cell Alloimmunity" *Am. J. Transplant* (Jun. 27, 2013); 13(10):2530-2539.
Dairaghi D.J. et al., "Chemokine Receptor CCR3 Function Is Highly Dependent on Local pH and Ionic Strength," The Journal of Biological Chemistry, Nov. 7, 1997, vol. 272, No. 45, pp. 28206-28209.
Dairaghi D.J. et al., "HHV8-encoded vMIP-I selectively Engages Chemokine Receptor CCR8 Agonist and Antagonist Profiles of Viral Chemokines," The Journal of Biological Chemistry, Jul. 30, 1999, vol. 274, No. 31, pp. 21569-21574.
Drugnews, "CSC168 ChemoCentryx Identifies C5a receptor antagonist GlaxoSmithKline milestone payment ChemoCentryx milestone payment," R & D Focus Drug News, May 2009, pp. 1-2, http://business. hgihbeam.com/436989/article-1G1-199837927/ccx-168-chemocentryx-identi . . . , retrieved Sep. 5, 2015.
Gerber B. O. et al., "An Activation Switch in the Ligand Binding Pocket of the C5a Receptor," The Journal of Biological Chemistry, Feb. 2, 2001, vol. 276, No. 5, pp. 3394-3400.
Horiuchi, Takahiko et al., "Complement-targeted therapy: development of C5- and C5a-targed inhibition," *Inflammation and Regeneration* (published online Jun. 3, 2016); 36(11): 1-6.
Hu et al., "Small molecules in treatment of sepsis," Current Drug Targets, 2011, vol. 12, pp. 256-262.
Huber-Lang et al., "Protection of innate immunity by C5aR antagonist in septic mice," The FASEB Journal, Oct. 2002, vol. 16, pp. 1567-1574.
Huber-Lang et al., "Role of Complement in Multi-Organ Dysfunction Syndrome," *The Complement System*, Abstract, (© 2004; Print/DOI: 10.1007/1-4020-8056-5_22); pp. 465-480.
"Improper Markush," (Feb. 9, 2011); Fed. Registry 76(27):7162-7175, slide 1, 64-67.
Inflammation, Wikipedia, https://en.wikipedia.org/wiki/inflammation, retrieved Sep. 7, 2015, pp. 1-30.
"Ischemia-reperfusion injury in vascular disease," Sebastian de la Fuente, Apr. 2009, pp. 1-54.
Jayne et al., "Oral C5A Receptor Antagonist CCX168 Phase 2 Clinical Trial in ANCA-Associated Renal Vasculitis", Ann Rheum Dis, 2014, vol. 73(suppl 2), p. 148.
Kumar et al., "Cell-derived anaphylatoxins as key mediators of antibody-dependent type II autoimmunity in mice," *J. Clin. Invest.*, (Feb. 2006; accepted in revised form Nov. 15, 2005); 116(2):512-520.

(56) References Cited

OTHER PUBLICATIONS

Kusner et al., "Effect of complement and its regulation on myasthenia gravis pathogenesis," *Expert Rev. Clin. Immunol.* (Jan. 2008; doi:10.1586/1744666X.4.1.43); 4(1):43-52.
Lachmann, P. J. et al., "Taking Complement to the Clinic—has the Time Finally Come?," *Scandinavian Journal of Immunology* (pub online Apr. 1, 2009); 69:471-478.
Lally, Lindsay et al., "Current Therapies for ANCA-Associated Vasculitis," *Annu. Rev. Med.* (2015; first Pub online Oct. 17, 2014); 66:227-240.
Lee, Hyun et al., "Receptors for complement C5a. The importance of C5aR and the enigmatic role of C5L2," *Immunol. Cell Biol.* (published online Jan. 29, 2008); 86(2):153-160.
Le Quintrec, Moglie, M.D., Ph.D., "Eculllizumab for Treatment of Rapidly Progressive C3 Glomerulopathy," *Am J Kidney Dis.* (2015; originally published on-line Dec. 16, 2014); 65(3):484-489.
Lupus Nephritis Definition *Wikipedia* https://en.wikipedia.org/wiki/Lupus_nephritis (May 26, 2017); 3 pages.
March, Darren R. et al., "Potent Cyclic Antagonists of the Complement C5a Receptor on Human Polymorphonuclear Leukocytes. Relationships between Structures and Activity," *Molecular Pharmacology* (2004; accepted Jan. 7, 2004); 65(4):868-879.
MedlinePlus "Sepsis," 2012, pp. 1-3.
Mizuno et al., "Novel C5a regulators in inflammatory disease," Exp. Opin. Investig. Drugs, 2005, vol. 14(7), pp. 807-821.
Monk et al., "Function, structure and therapeutic potential of complement C5a receptors," British Journal of Pharmacology, 2007, vol. 152, pp. 429-488.
Nikforovich et al., "Modeling Molecular Mechanisms of Binding of the Anaphylatoxin C5 to the C5a Receptor," Biochemistry, 2008, 47, 3117-3130.
Noël, Romain, et al., "Synthesis of New Chiral 6-Carbonyl 2,3,8,8a-Tetrahydro-7H-oxazolo[3,2-α]pyridines," *J. Org. Chem.* (Oct. 1, 2005); 70(22):9044-9047.
Noël, Romain, et al., "Diastereoselective Reduction of Bicyclic β-Enamino Carbonyl Piperidines—Application to the Total Syntehsis of (−)-Deoocassine," *Eur. J. Org. Chem.* (2007; published online Nov. 17, 2006 DOI: 10.1002/ejoc.200600777); 476-486.
Noël, Romain, et al., "Convenient One-Pot Synthesis of Chiral Tetrahydropyridines via a Multicomponent Reaction," *Synthesis* (2008; advanced online publication May 16, 2008); 12:1948-1954.
Osoda, Tsutomu et al., "2D-Qsar for 450 types of amino acid induction peptides with a novel substructure pair descriptor having wider scope," *Journal of Cheminformatics* (Nov. 2, 2011);3:50; 9 pages.
Paczkowski et al., "Pharmacological characterization of antagonists of the C5a receptor," British J. of Pharmacology, 1999, 128, 1461-1466.
Penfold M.E.T. et al., "Cytomegalovirus encodes a potent α chemokine," Proc. Natl. Acad. Sci. USA, Aug. 1999, vol. 96, pp. 9839-9844.
Press Release: ChemoCentryx Announces Presentation of Positive Results from Phase II ANCA-Associated Vasculitis Clear Trial of Orally Administered Complement 5a Receptor Inhibitor CCX168 at the 53$^{rd}$ ERA-EDTA Congress (May 23, 2016); 5 pages.
Press Release: ChemoCentryx Announces Presentation of Positive Data from Ongoing Pilot Phase II Trial of CCX168 (Avacopan) in Atypical Hemolytic Uremic Syndrome (AHUS) at ASN Kidney Week 2016 (Oct. 17, 2016); 3 pages.
Procter, Lavinia M. et al., "Recent developments in C5/C5a inhibitors," *Expert Opinion on Therapeutic Patents*, (Mar. 24, 20016); 16(4):445-458.
PubChem-CID-58506549; Create date Aug. 19, 2012, p. 3 Fig.
PubChem-CID-58506538; Create date Aug. 19, 2012, p. 3, Fig.
PubChem-CID-68717675; Create date Nov. 30, 2012, p. 3, Fig.
PubChem-CID-68607180; Create date Nov. 30, 2012, p. 3, Fig.
Qu et al., "Recent developments in low molecular weight complement inhibitors," Molecular Immun., 2009, vol. 47, pp. 185-195.
Rheumatoid Arthritis Definition *Johns Hopkins Arthritis Center* https://www.hopkinsarthritis.org/arthritis-info/rheumatoid-arthritis/ra-treatment/ (May 26, 2017); 3 pages.
Ricklin, Daniel et al., "Complement-targeted therapeutics," *Nature Biotechnology* (pub online Nov. 7, 2007); 25(11):1265-1275.
Ricklin, Daniel, et al., "Complement in immune and inflammatory disorders: therapeutic interventions," *J. Immunol.* (Apr. 15, 2013); 190(8):3839-38 47.
Riedemann et al., "The enigma of sepsis," The Journal of Clinical Investigation, 2003, vol. 112, No. 4, pp. 460-467.
Rittirsch et al., "Harmful molecular mechanisms in sepsis," Nat. Rev. Immunol., Oct. 2008, vol. 8(10). pp. 776-787.
RN 1348614-10-7 Database:GVK BIO (2011).
Sarma et al., "New developments in C5a receptor signaling," Cell Health and Cytoskeleton, 2012, vol. 4, pp. 73-82.
Seddon, "Pseudopolymorph: A Polemic," Crystal Growth & Design, 2004, vol. 4, No. 6, p. 1087.
Short et al., "Effects of a new C5a receptor antagonist on C5a- and endotoxin-induced neutropenia in the rat," British J. Pharma., 1999, vol. 125, pp. 551-554.
Short, Anna J. et al., "Response-selective C5a agonists: differential effects on neutropenia and hypotension in the rat," *British J. Pharma* (1999; accepted Jul. 21, 1999); 128:511-514.
Siciliano et al., "Two-site binding of C5a by its receptor: An alternative binding paradigm for G protein-coupled receptors," Proc. Natl. Acad. Sci. USA, Feb. 1994, vol. 91, pp. 1214-1218.
Sridharan, Vellaisamy et al., "A Very Efficient Cerium(IV) Ammonium Nitrate Catalyzed, Four-Component Synthesis of Tetrahydropyridines and Its Application in the Concise Generation of Functionalized Homoquinolizine Frameworks," *Chem Eur. J.* (published online Mar. 13, 2009; DOI:10.1002/CHEM.200900044); 15;4565-4572.
Strachan A.J. et al., "A New Small Molecule C5a Receptor Antagonist Inhibits the Reverse-Passive Arthus Reaction and Endotoxic Shock in Rats," The Journal of Immunology, 2000, vol. 164, pp. 6560-6565.
Sumichika H. et al., "Identification of a Potent and Orally Active Non-peptide C5a Receptor Antagonist," The Journal of Biological Chemistry, Dec. 20, 2002, vol. 277, No. 51, pp. 49403-49407.
Taylor et al., "Development of response-selective agonists of human C5a anaphylatoxin: conformational, biological, and therapeutic considerations," Current Med. Chem., 2001, vol. 8., pp. 675-684.
"Treatment of Acute Rejection," American Journal of Transplantation, 2009, vol. 9 (Suppl 3), pp. S21-S22.
Unsinger et al., "Sepsis-induced human lymphocyte apoptosis and cytokine production in "humanized" mice," Journal of Leukocyte Biology, vol. 86, 2009, pp. 219-227.
Ward, "The Harmful Role of C5a on Innate Immunity in Sepsis," J. Innate Immun, 2010, vol. 2, pp. 439-445.
Ward, "Role of the complement in experimental sepsis," Journal of Leukocyte Biology, Mar. 2008, vol. 83, pp. 467-470.
Ward et al., "The dark side of C5a in sepsis," Nature Reviews, 2004, vol. 4, pp. 133-142.
Warren, "Mouse models to study sepsis syndrome in humans" J. Leukocyte Biol., 2009 vol. 86, pp. 199-200.
Woodruff T.M. et al., "A Potent Human C5a Receptor Antagonist Protects against Disease Pathology in a Rat Model of Inflammatory Bowel Disease," The Journal of Immunology, 2003, vol. 171, pp. 5514-5520.
Woodruff et al., "Species dependence for binding of small molecule agonist and antagonists to the C5a receptor on polymorphonuclear leukocytes," Inflammation, 2001, vol. 25(3), pp. 171-177.
Wygnaarden et al., Textbook of medicine, 16th Edition, 1983, p. 247.
Xiao et al.,"C5a Receptor (CD88) Blockade Protects against MPO-ANCA GN," *J. Am. Soc. Nephrol.* (2014; accepted for publication Aug. 5, 2013); 25(2):225-231.
Yan et al., "New insights for C5a and C5a receptors in sepsis," Frontiers in Immunology, Dec. 2012, vol. 3, Article 368, pp. 1-15.
Yatime, Laure et al., "Structural basis for the targeting of complement anaphylatoxin C5a using a mixed L-RNA/L-DNA aptamer," *Nature Communications* (Apr. 22, 2015); 13 pages.

FIG. 1A

| # | Structure | C5aR binding | # | Structure | C5aR binding |
|---|---|---|---|---|---|
| 1.001 | 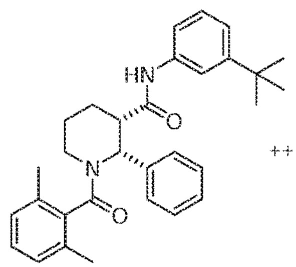 | ++ | 1.002 | 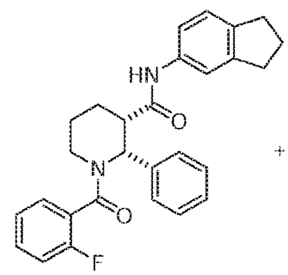 | + |
| 1.003 | 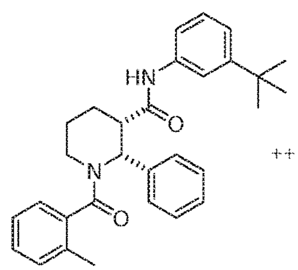 | ++ | 1.004 | 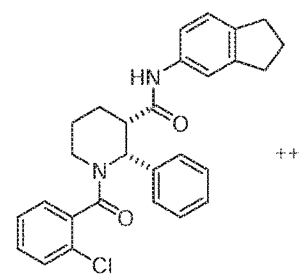 | ++ |
| 1.005 | 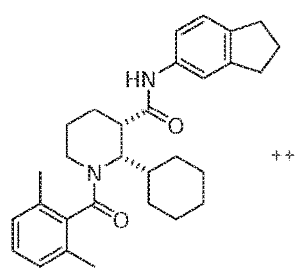 | ++ | 1.006 | 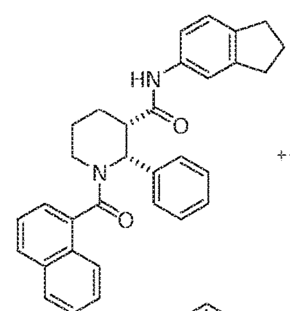 | ++ |
| 1.007 | 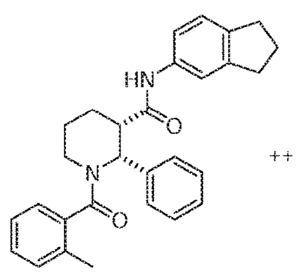 | ++ | 1.008 | 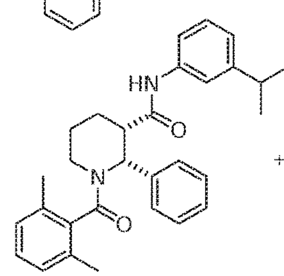 | ++ |

FIG. 1B
| # | Structure | C5aR binding | # | Structure | C5aR binding |
|---|---|---|---|---|---|
| 1.009 | 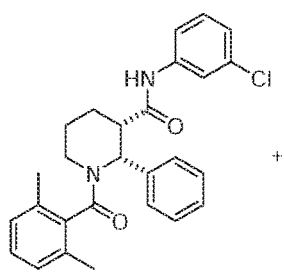 | + | 1.010 | 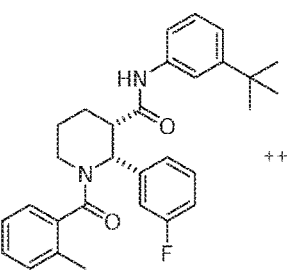 | ++ |
| 1.011 | 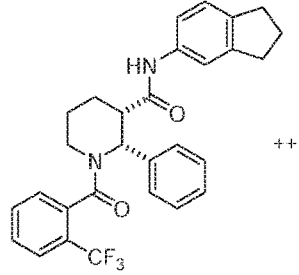 | ++ | 1.012 | 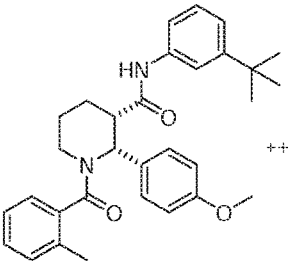 | ++ |
| 1.013 | 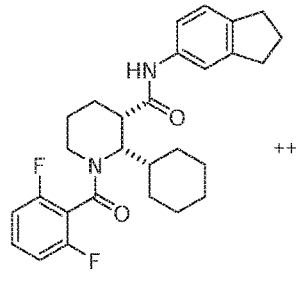 | ++ | 1.014 | 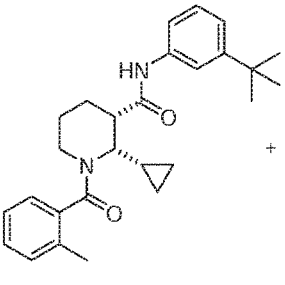 | + |
| 1.015 | 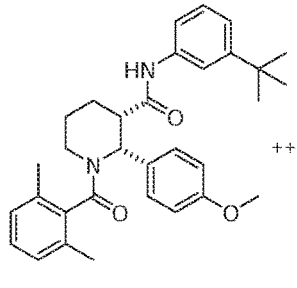 | ++ | 1.016 | 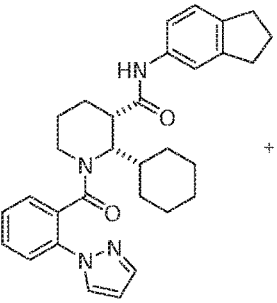 | + |

FIG. 1C

| # | Structure | C5aR binding | # | Structure | C5aR binding |
|---|---|---|---|---|---|
| 1.017 | 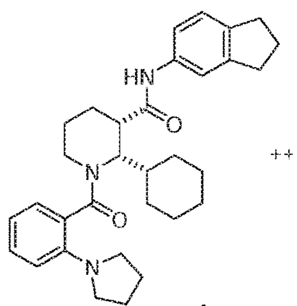 | ++ | 1.018 | 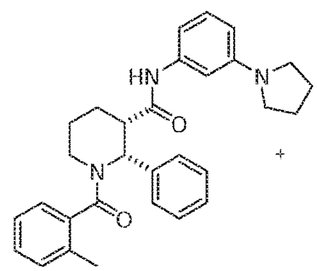 | + |
| 1.019 | 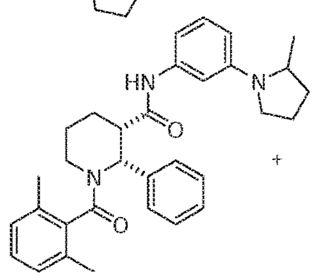 | + | 1.020 | 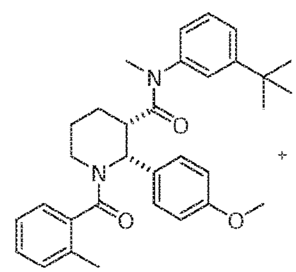 | + |
| 1.021 | 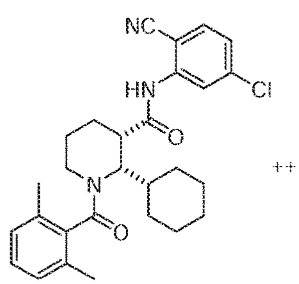 | ++ | 1.022 | 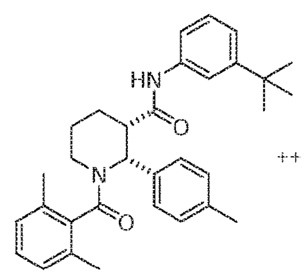 | ++ |
| 1.023 | 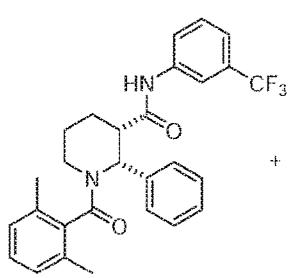 | + | 1.024 | 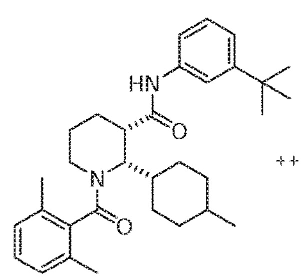 | ++ |

FIG. 1D

| # | Structure | C5aR binding | # | Structure | C5aR binding |
|---|---|---|---|---|---|
| 1.025 | 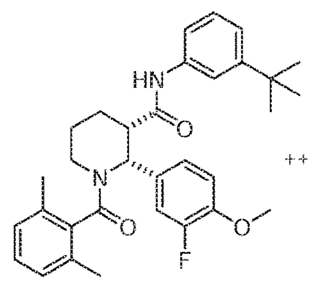 | ++ | 1.026 | 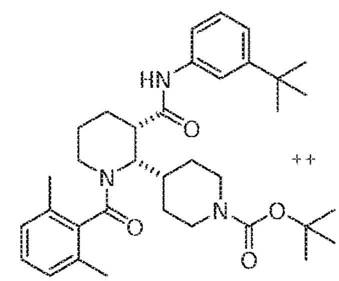 | ++ |
| 1.027 | 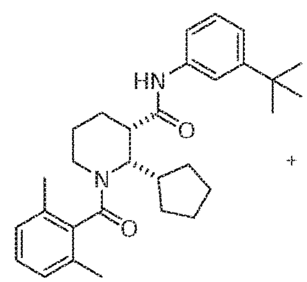 | + | 1.028 | 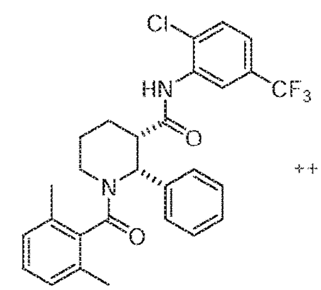 | ++ |
| 1.029 | 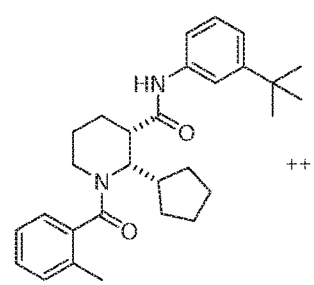 | ++ | 1.030 | 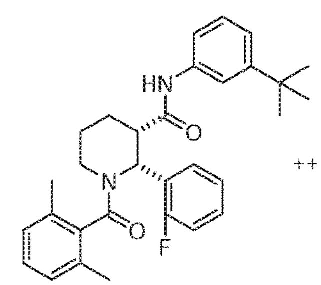 | ++ |
| 1.031 | 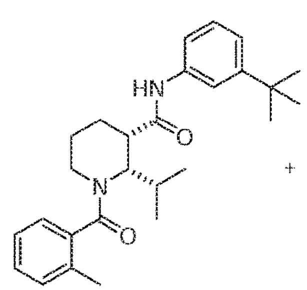 | + | 1.032 | 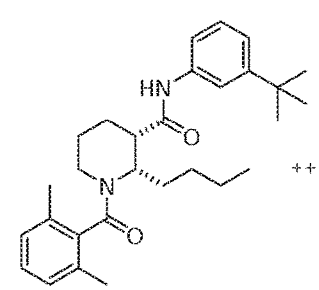 | ++ |

FIG. 1F

| # | Structure | C5aR binding | # | Structure | C5aR binding |
|---|---|---|---|---|---|
| 1.041 | 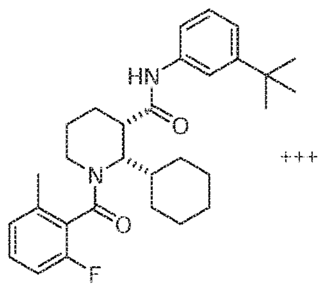 | +++ | 1.042 | 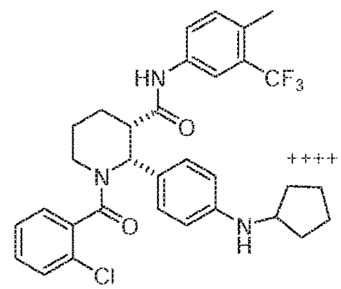 | ++++ |
| 1.043 | 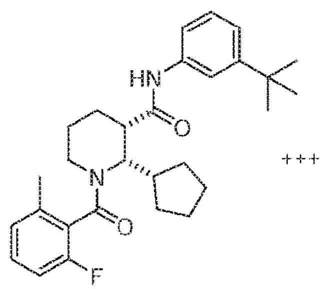 | +++ | 1.044 | 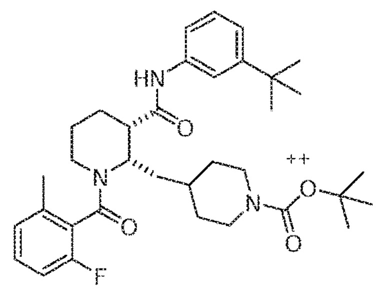 | ++ |
| 1.045 | 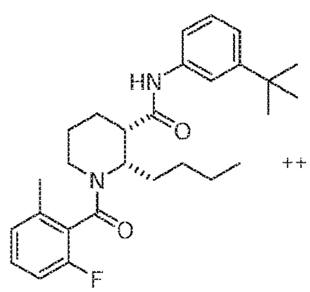 | ++ | 1.046 | 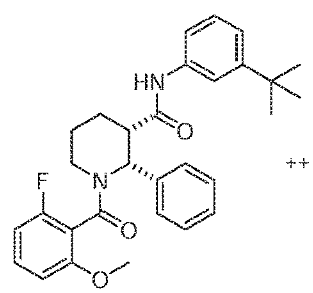 | ++ |
| 1.047 | 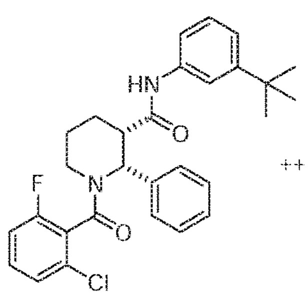 | ++ | 1.048 | 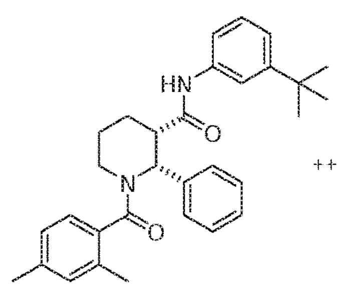 | ++ |

FIG. 1J

| # | Structure | C5aR binding | # | Structure | C5aR binding |
|---|---|---|---|---|---|
| 1.073 | 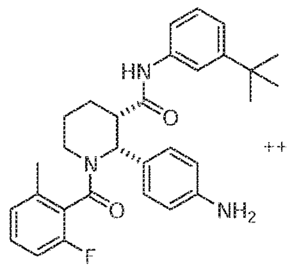 | ++ | 1.074 | 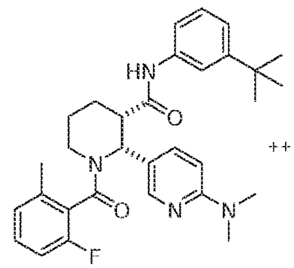 | ++ |
| 1.075 | 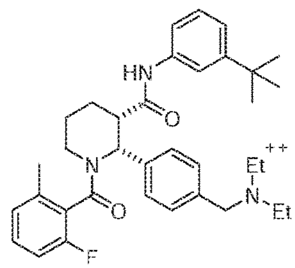 | ++ | 1.076 | 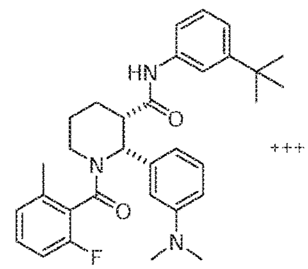 | +++ |
| 1.077 | 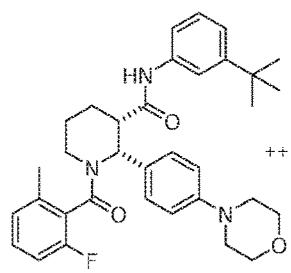 | ++ | 1.078 | 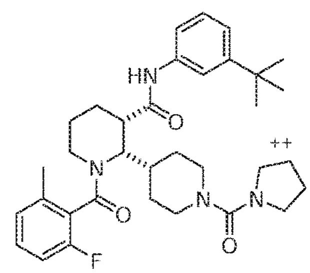 | ++ |
| 1.079 | 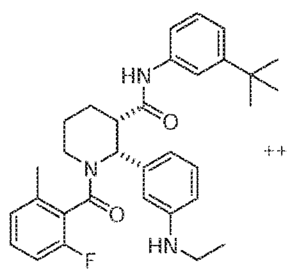 | ++ | 1.080 | 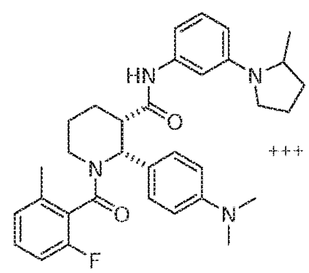 | +++ |

FIG. 1K

| # | Structure | C5aR binding | # | Structure | C5aR binding |
|---|---|---|---|---|---|
| 1.081 | 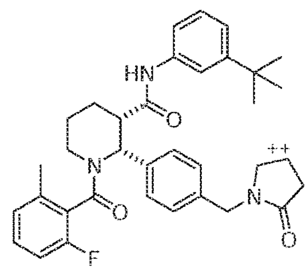 | ++ | 1.082 | 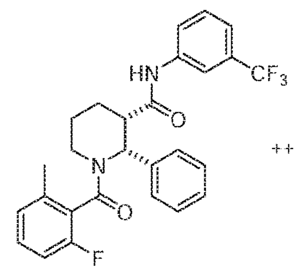 | ++ |
| 1.083 | 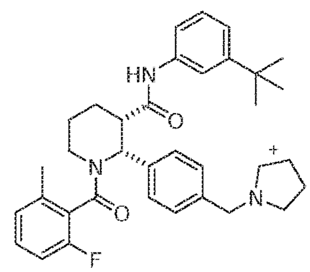 | + | 1.084 | 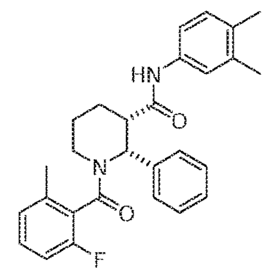 | +++ |
| 1.085 | 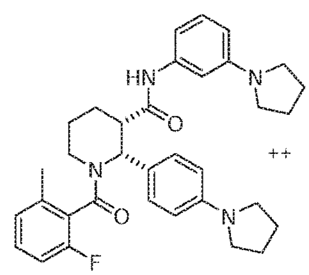 | ++ | 1.086 | 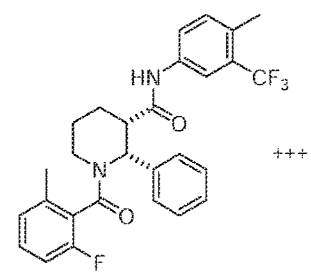 | +++ |
| 1.087 | 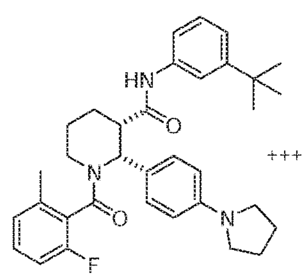 | +++ | 1.088 | 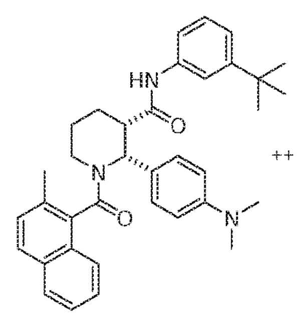 | ++ |

FIG. 1N

| # | Structure | C5aR binding | # | Structure | C5aR binding |
|---|---|---|---|---|---|
| 1.105 | 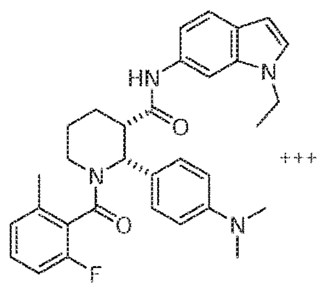 | +++ | 1.106 | 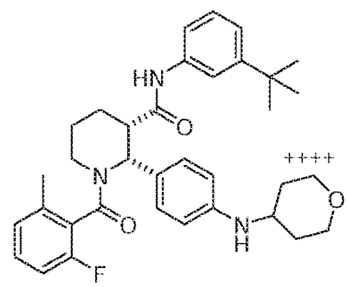 | ++++ |
| 1.107 | 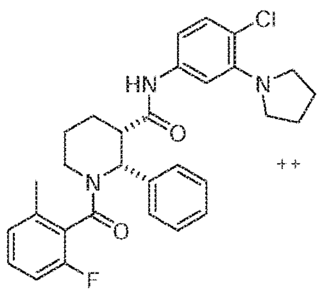 | ++ | 1.108 | 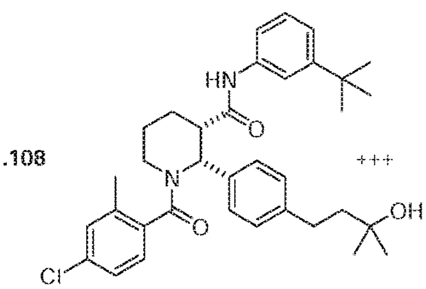 | +++ |
| 1.109 | 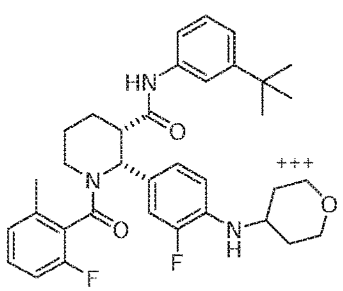 | +++ | 1.110 | 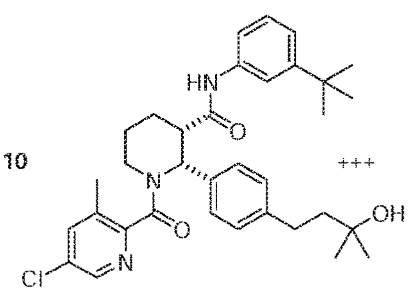 | +++ |
| 1.111 | 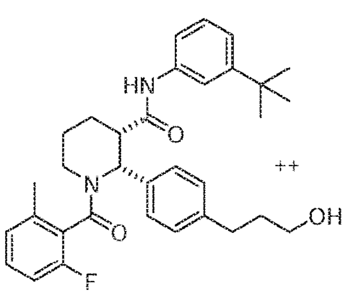 | ++ | 1.112 | 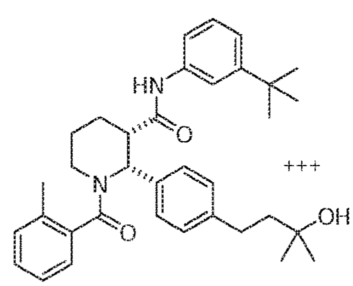 | +++ |

FIG. 10

| # | Structure | C5aR binding | # | Structure | C5aR binding |
|---|---|---|---|---|---|
| 1.113 | 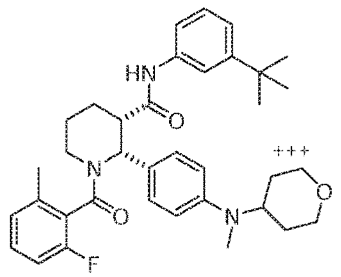 | +++ | 1.114 | 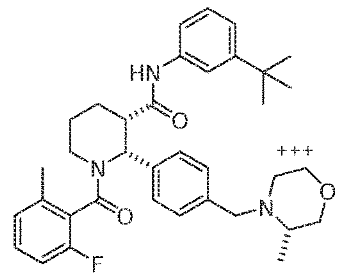 | +++ |
| 1.115 | 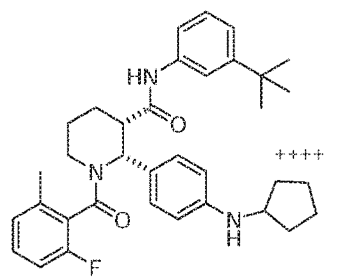 | ++++ | 1.116 | 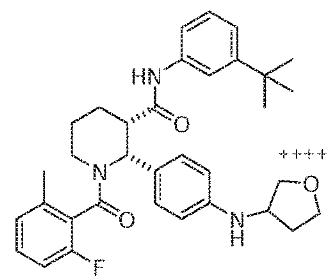 | ++++ |
| 1.117 | 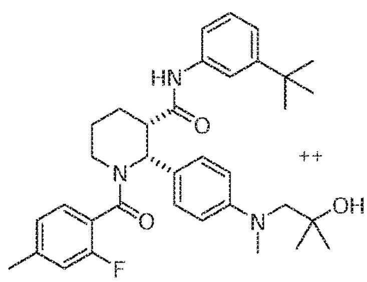 | ++ | 1.118 | 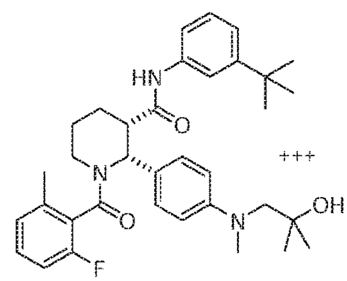 | +++ |
| 1.119 | 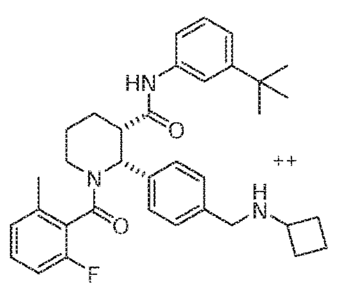 | ++ | 1.120 | 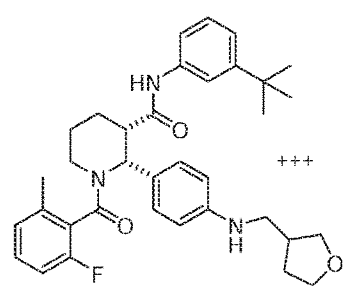 | +++ |

FIG. 1P

| # | Structure | C5aR binding | # | Structure | C5aR binding |
|---|---|---|---|---|---|
| 1.121 | 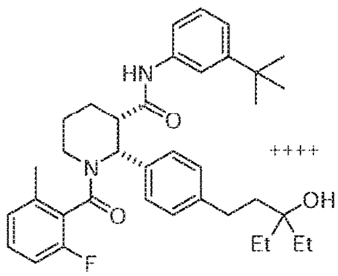 | ++++ | 1.122 | 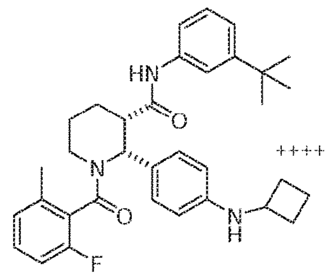 | ++++ |
| 1.123 | 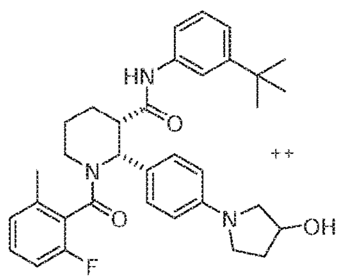 | ++ | 1.124 | 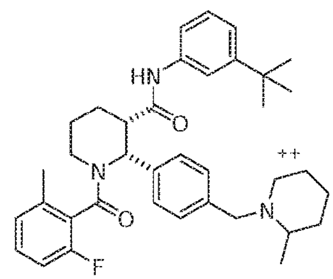 | ++ |
| 1.125 | 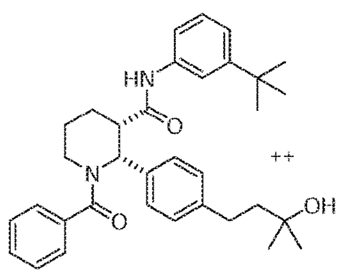 | ++ | 1.126 | 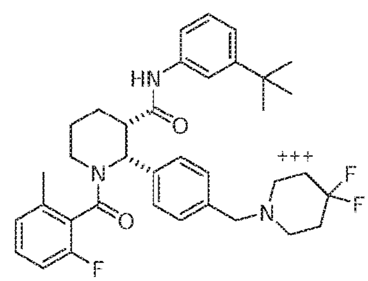 | +++ |
| 1.127 | 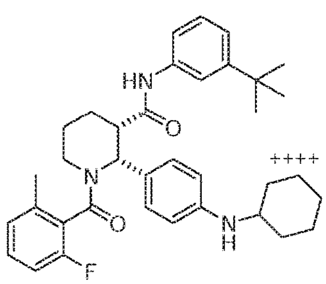 | ++++ | 1.128 | 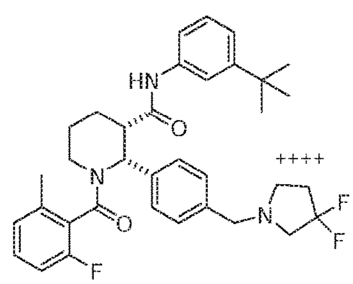 | ++++ |

| # | Structure | C5aR binding | # | Structure | C5aR binding |
|---|---|---|---|---|---|
| 1.145 | | ++++ | 1.146 | | ++++ |
| 1.147 | | +++ | 1.148 | | ++++ |
| 1.149 | | ++++ | 1.150 | | ++++ |
| 1.151 | | ++++ | 1.152 | | ++++ |

FIG. 1T
| # | Structure | C5aR binding | # | Structure | C5aR binding |
|---|---|---|---|---|---|
| 1.153 | 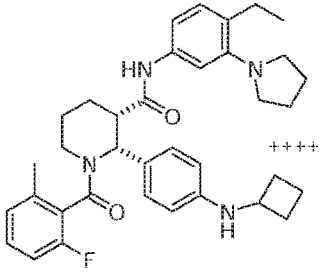 | ++++ | 1.154 | 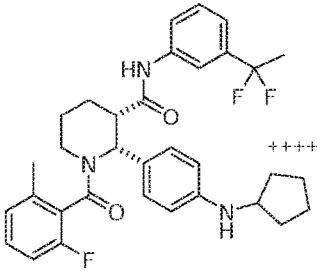 | ++++ |
| 1.155 | 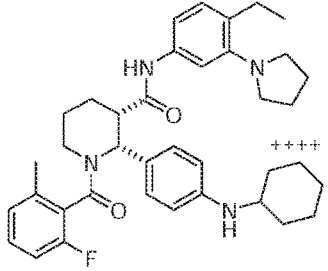 | ++++ | 1.156 | 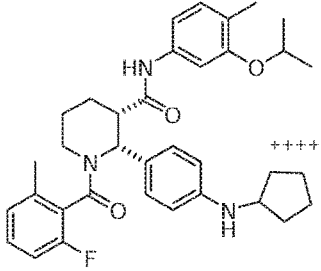 | ++++ |
| 1.157 | 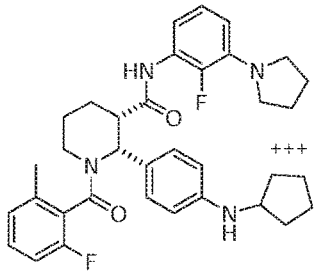 | +++ | 1.158 | 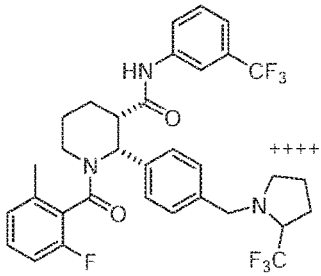 | ++++ |
| 1.159 | 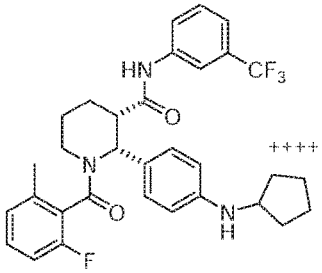 | ++++ | 1.160 | 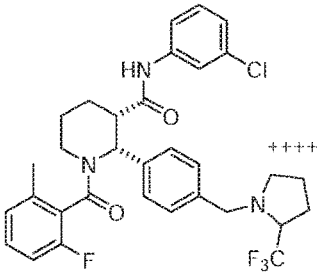 | ++++ |

FIG. 1V

| # | Structure | C5aR binding | # | Structure | C5aR binding |
|---|---|---|---|---|---|
| 1.169 | 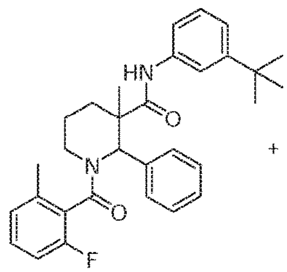 | + | 1.170 | 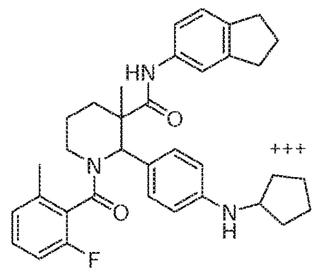 | +++ |
| 1.171 | 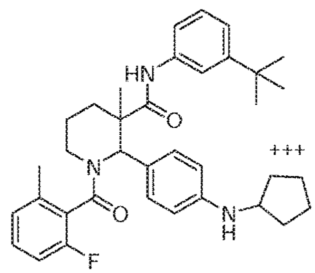 | +++ | 1.172 | 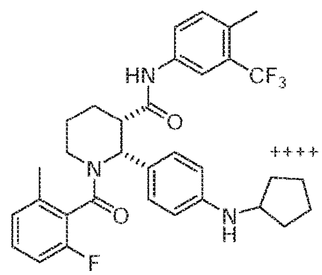 | ++++ |
| 1.173 | 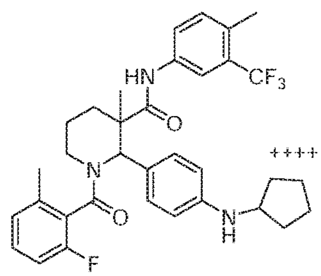 | ++++ | 1.174 | 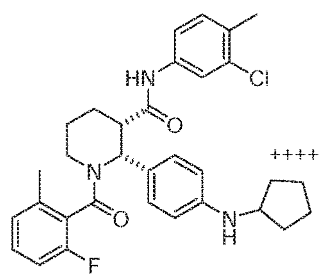 | ++++ |
| 1.175 | 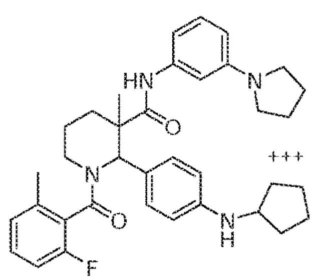 | +++ | 1.176 | 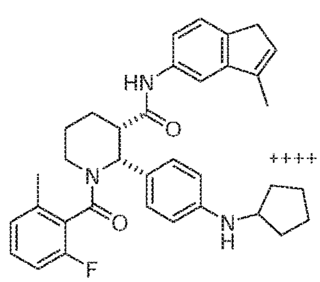 | ++++ |

FIG. 1W
| # | Structure | C5aR binding | # | Structure | C5aR binding |
|---|---|---|---|---|---|
| 1.177 | 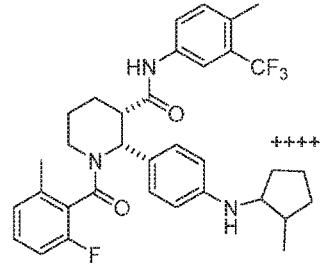 | ++++ | 1.178 | 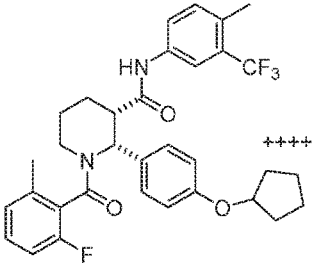 | ++++ |
| 1.179 | 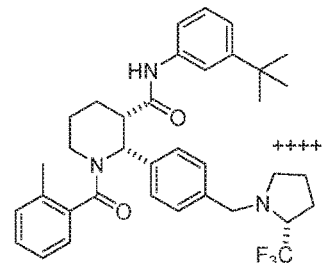 | ++++ | 1.180 | 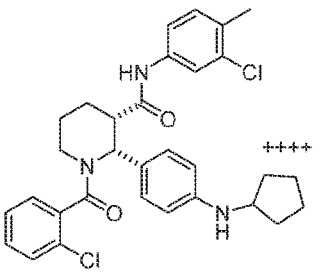 | ++++ |

FIG. 1Z

| # | Structure | C5aR binding | # | Structure | C5aR binding |
|---|---|---|---|---|---|
| 1.197 | 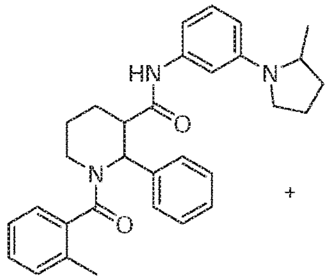 | + | 1.198 | 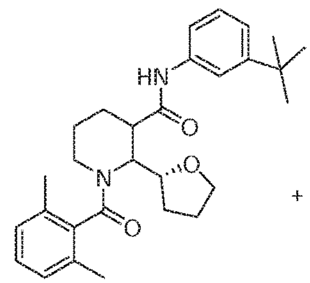 | + |
| 1.199 | 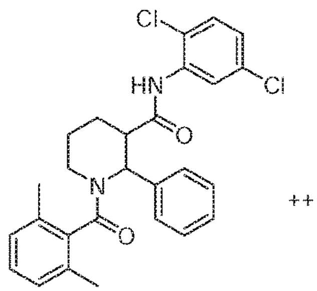 | ++ | 1.200 | 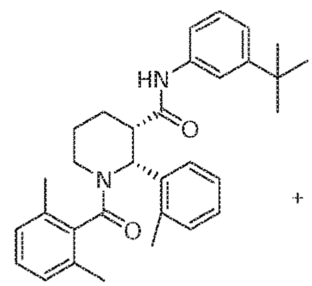 | + |
| 1.201 | 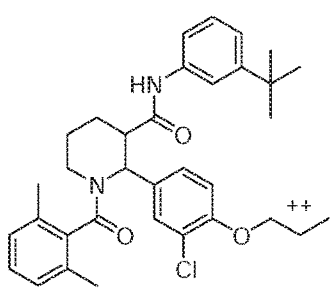 | ++ | 1.202 | 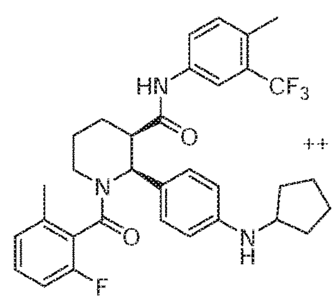 | ++ |
| 1.203 | 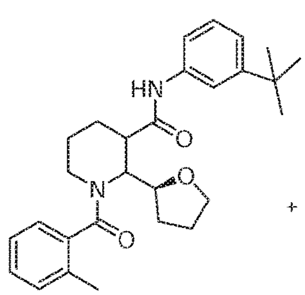 | + | 1.204 | 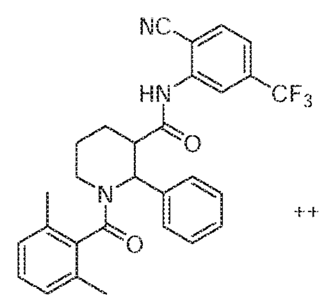 | ++ |

FIG. 1AA

| # | Structure | C5aR binding | # | Structure | C5aR binding |
|---|---|---|---|---|---|
| 1.205 | 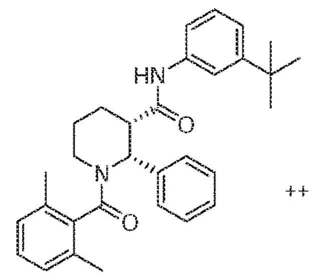 | ++ | 1.206 | 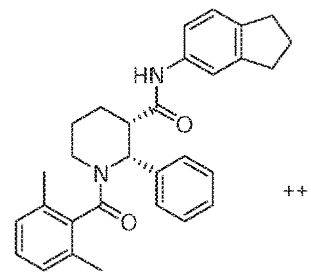 | ++ |
| 1.207 | 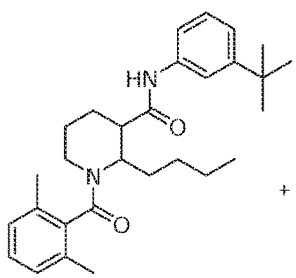 | + | 1.208 | 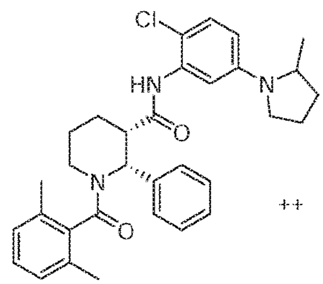 | ++ |
| 1.209 | 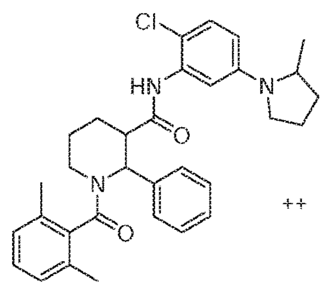 | ++ | 1.210 | 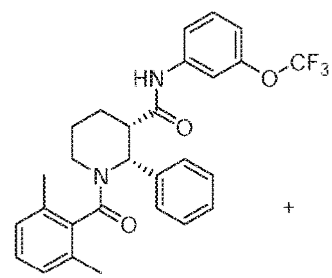 | + |
| 1.211 | 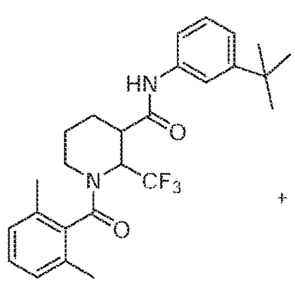 | + | 1.212 | 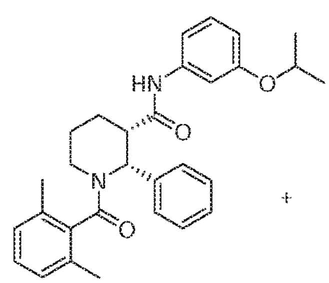 | + |

FIG. 1BB

| # | Structure | C5aR binding | # | Structure | C5aR binding |
|---|---|---|---|---|---|
| 1.213 | 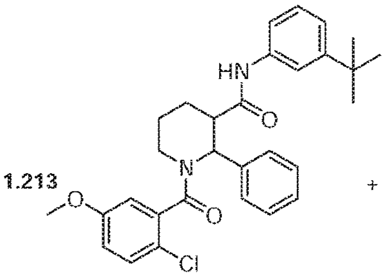 | + | 1.214 | 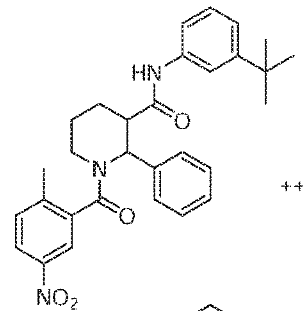 | ++ |
| 1.215 | 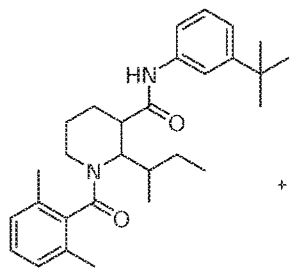 | + | 1.216 | 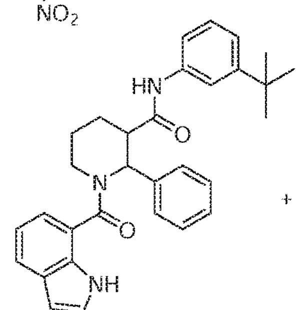 | + |
| 1.217 | 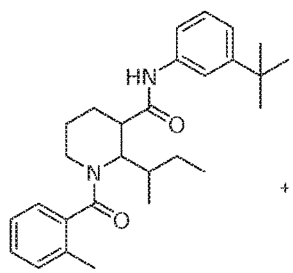 | + | 1.218 | 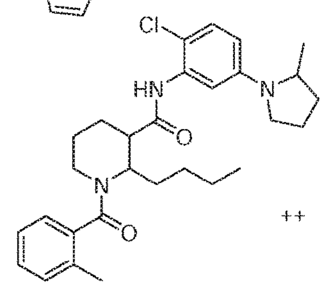 | ++ |
| 1.219 | 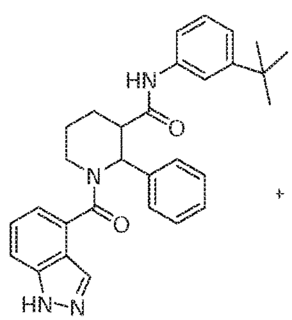 | + | 1.220 | 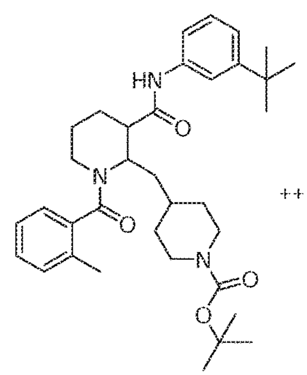 | ++ |

FIG. 1CC

| # | Structure | C5aR binding | # | Structure | C5aR binding |
|---|---|---|---|---|---|
| 1.221 | 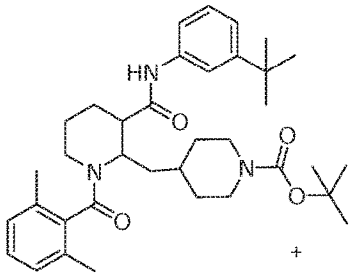 | + | 1.222 | 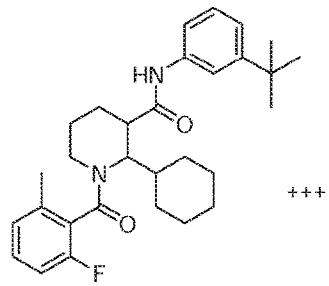 | +++ |
| 1.223 | 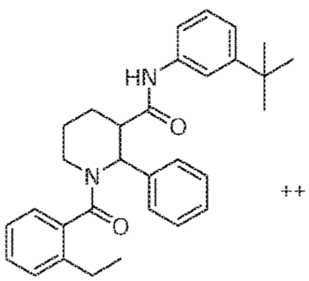 | ++ | 1.224 | 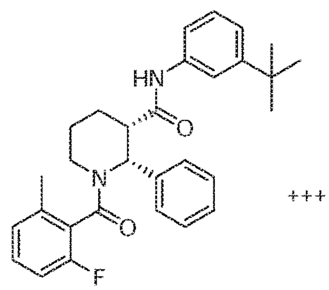 | +++ |
| 1.225 | 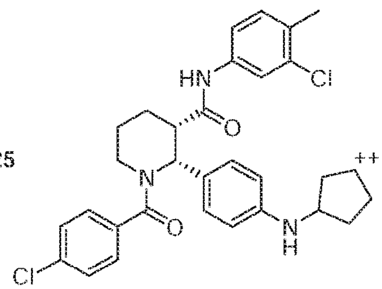 | +++ | 1.226 | 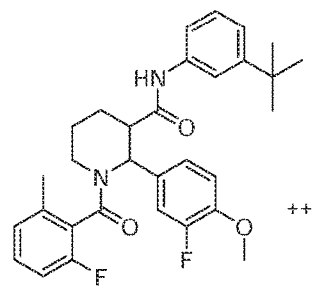 | ++ |
| 1.227 | 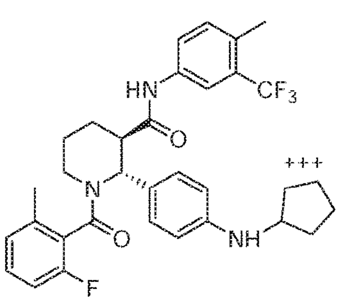 | +++ | 1.228 | 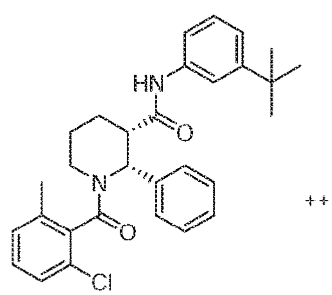 | ++ |

FIG. 1DD

| # | Structure | C5aR binding | # | Structure | C5aR binding |
|---|---|---|---|---|---|
| 1.229 | 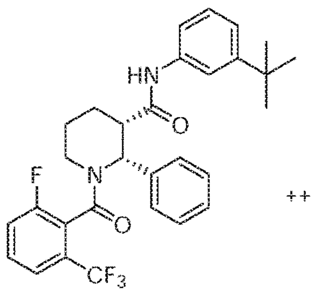 | ++ | 1.230 | 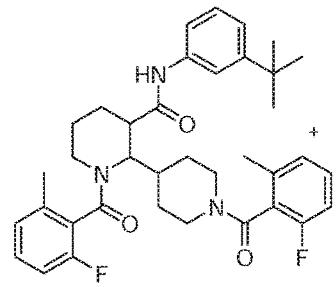 | + |
| 1.231 | 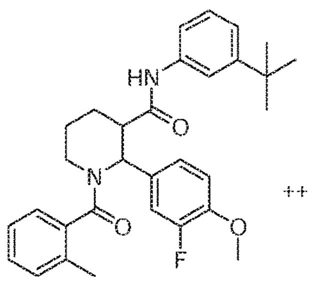 | ++ | 1.232 | 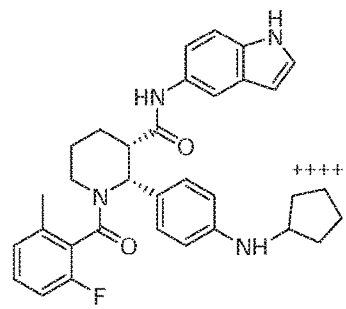 | ++++ |
| 1.233 | 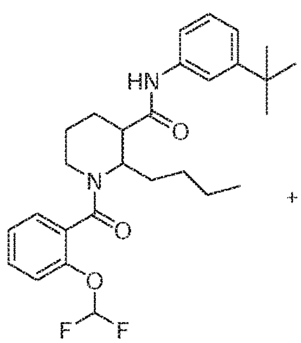 | + | 1.234 | 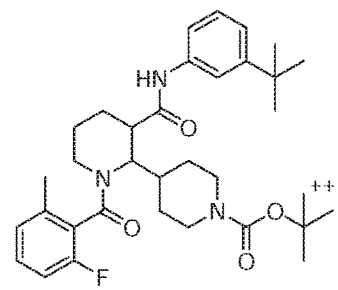 | ++ |
| 1.235 | 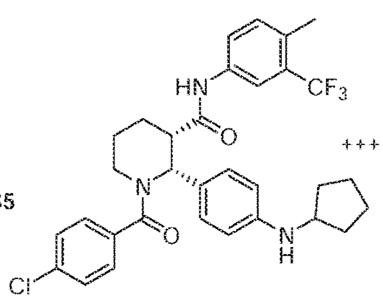 | +++ | 1.236 | 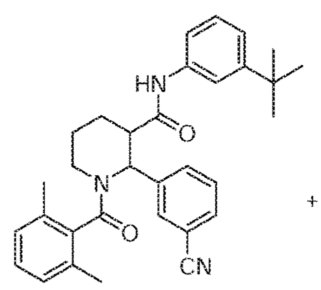 | + |

FIG. 1EE

| # | Structure | C5aR binding | # | Structure | C5aR binding |
|---|---|---|---|---|---|
| 1.237 | 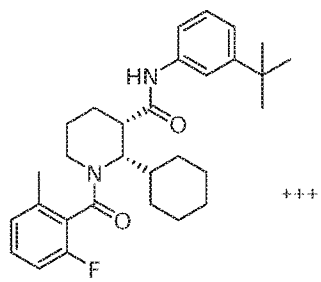 | +++ | 1.238 | 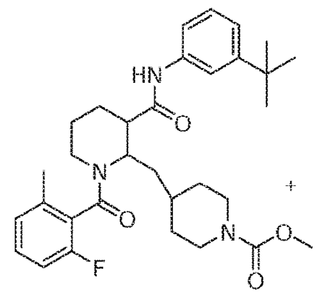 | + |
| 1.239 | 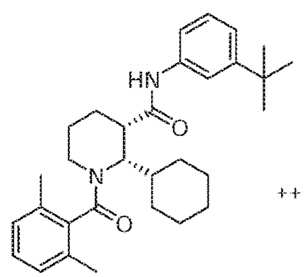 | ++ | 1.240 | 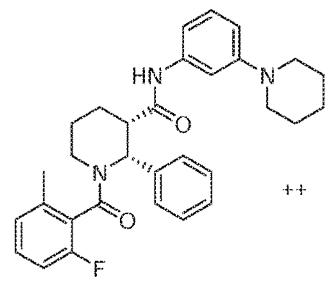 | ++ |
| 1.241 | 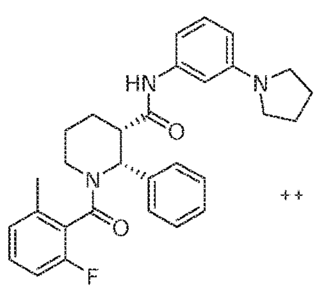 | ++ | 1.242 | 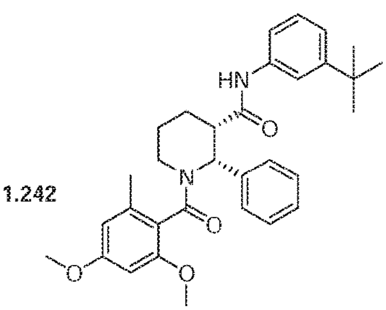 | + |
| 1.243 | 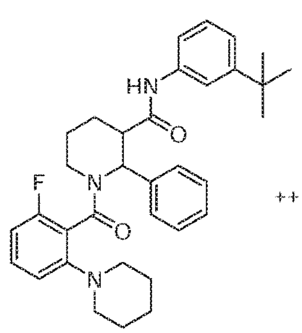 | ++ | 1.244 | 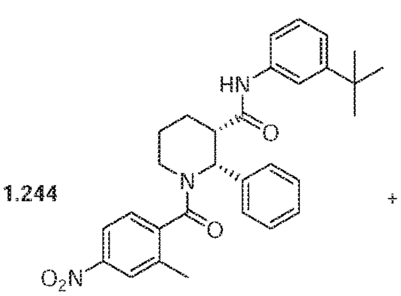 | + |

FIG. 1FF

| # | Structure | C5aR binding | # | Structure | C5aR binding |
|---|---|---|---|---|---|
| 1.245 | 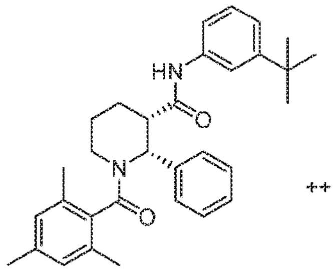 | ++ | 1.246 | 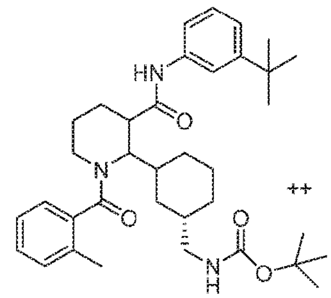 | ++ |
| 1.247 | 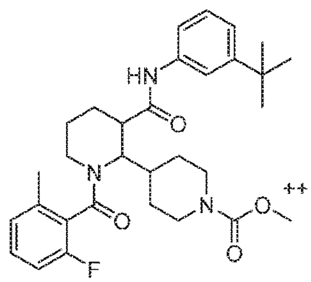 | ++ | 1.248 | 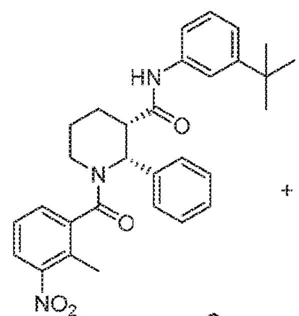 | + |
| 1.249 | 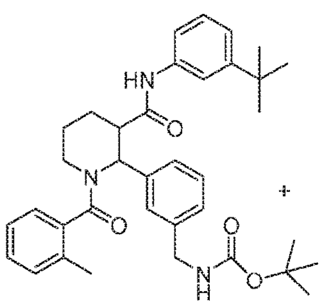 | + | 1.250 | 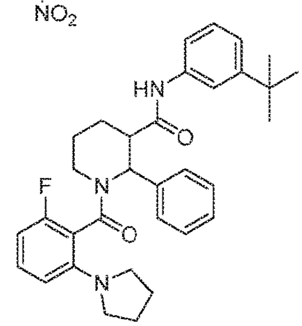 | + |
| 1.251 | 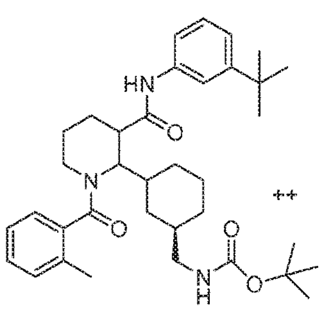 | ++ | 1.252 | 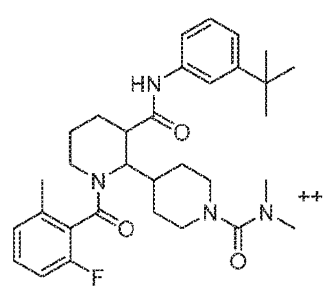 | ++ |

FIG. 1HH

| # | Structure | C5aR binding | # | Structure | C5aR binding |
|---|---|---|---|---|---|
| 1.261 | 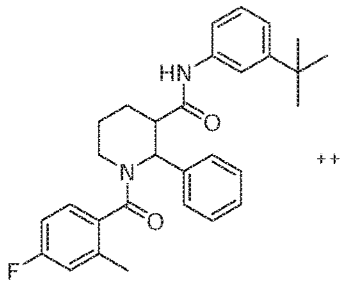 | ++ | 1.262 | 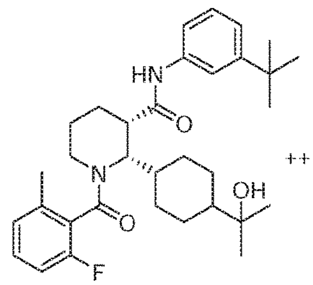 | ++ |
| 1.263 | 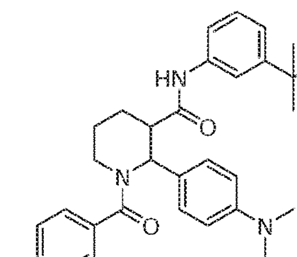 | +++ | 1.264 | 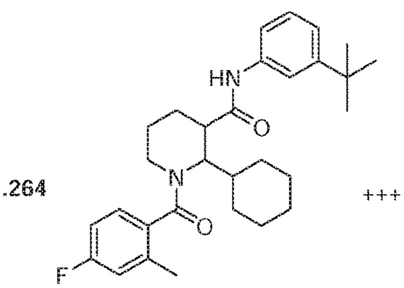 | +++ |
| 1.265 | 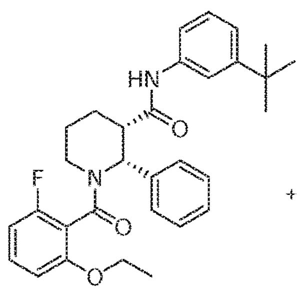 | + | 1.266 | 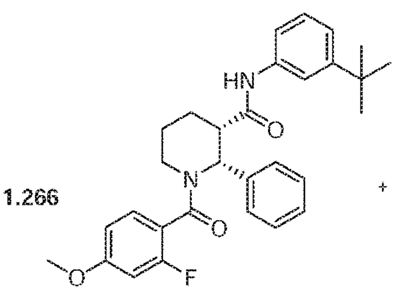 | + |
| 1.267 | 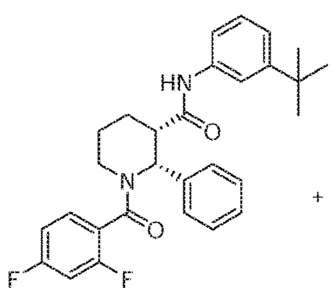 | + | 1.268 | 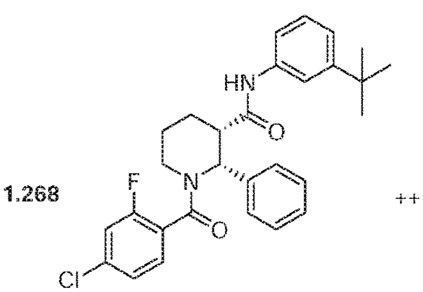 | ++ |

| # | Structure | C5aR binding | # | Structure | C5aR binding |
|---|---|---|---|---|---|
| 1.285 | 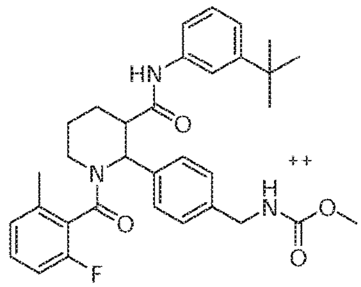 | ++ | 1.286 | 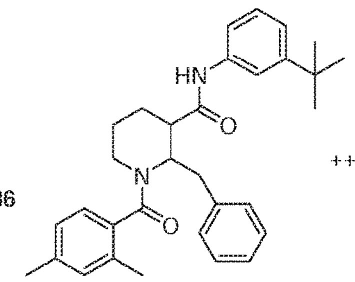 | ++ |
| 1.287 | 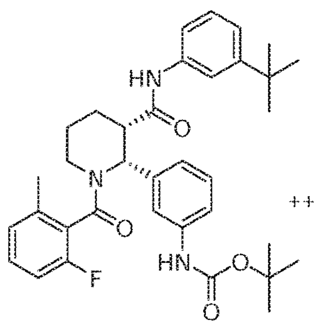 | ++ | 1.288 | 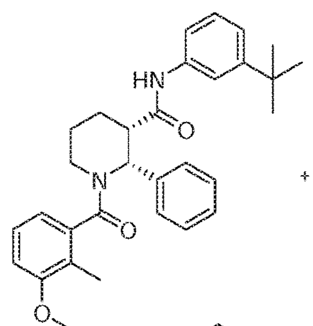 | ++ |
| 1.289 | 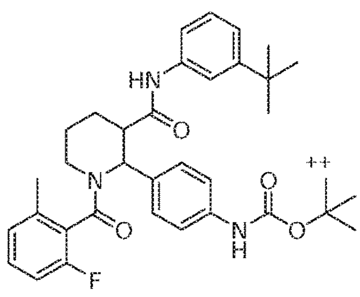 | ++ | 1.290 | 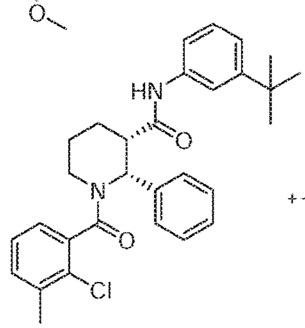 | ++ |
| 1.291 | 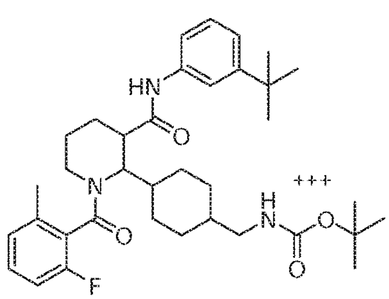 | +++ | 1.292 | 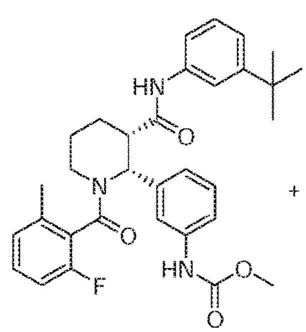 | + |

| # | Structure | C5aR binding | # | Structure | C5aR binding |
|---|---|---|---|---|---|
| 1.309 | 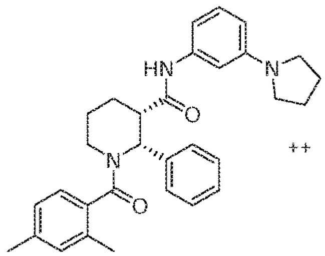 | ++ | 1.310 | 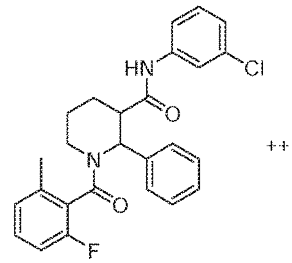 | ++ |
| 1.311 | 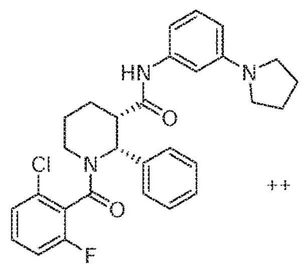 | ++ | 1.312 | 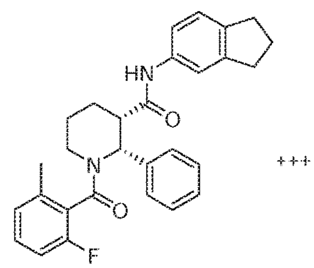 | +++ |
| 1.313 | 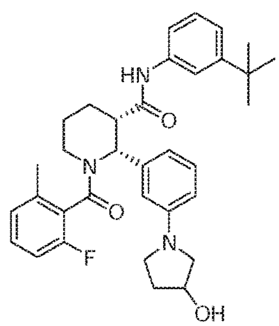 | + | 1.314 | 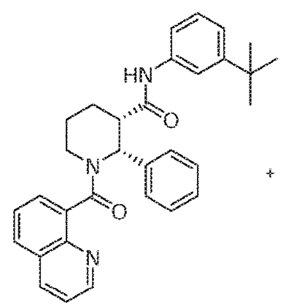 | + |
| 1.315 | 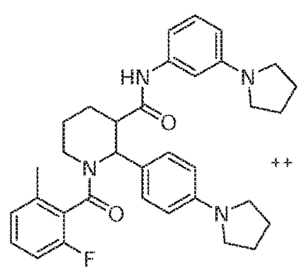 | ++ | 1.316 | 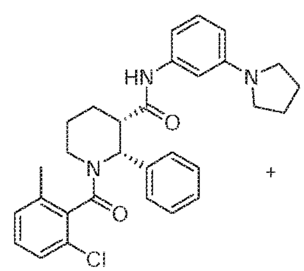 | + |

FIG. 1QQ

| # | Structure | C5aR binding | # | Structure | C5aR binding |
|---|---|---|---|---|---|
| 1.333 | 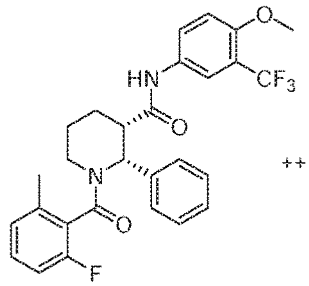 | ++ | 1.334 | 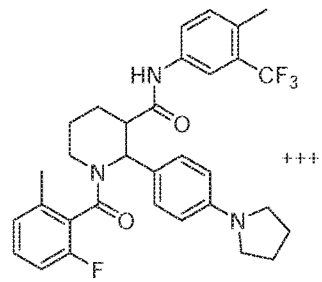 | +++ |
| 1.335 | 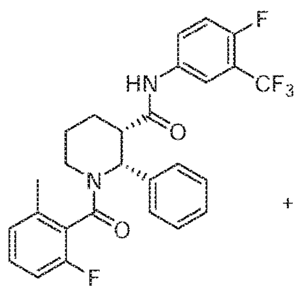 | + | 1.336 | 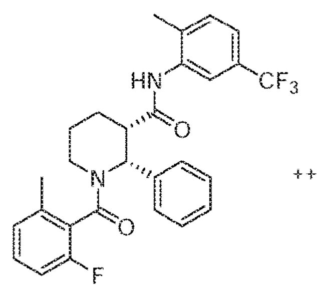 | ++ |
| 1.337 | 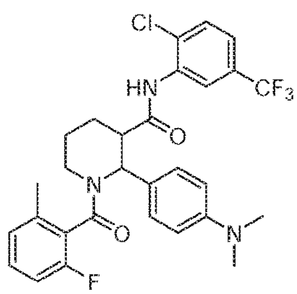 | ++ | 1.338 | 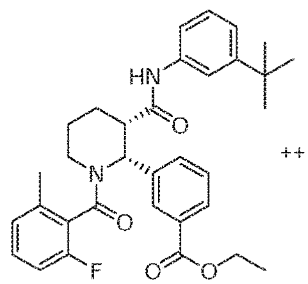 | ++ |
| 1.339 | 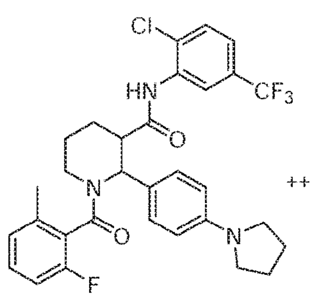 | ++ | 1.340 | 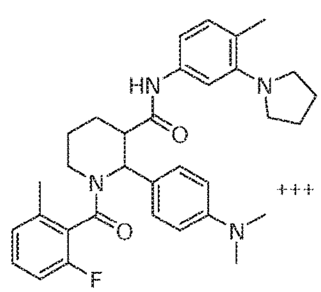 | +++ |

| # | Structure | C5aR binding | # | Structure | C5aR binding |
|---|---|---|---|---|---|
| 1.349 | 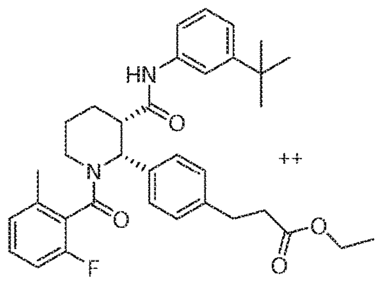 | ++ | 1.350 | 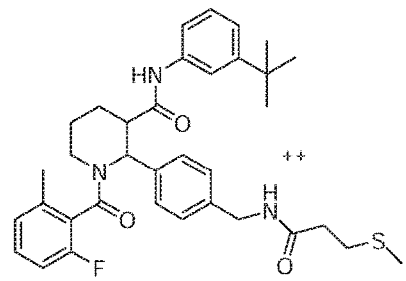 | ++ |
| 1.351 | 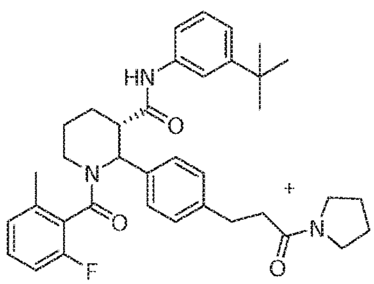 | + | 1.352 | 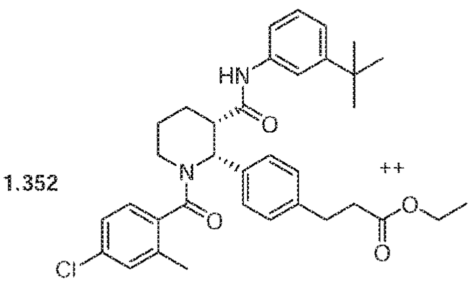 | ++ |
| 1.353 | 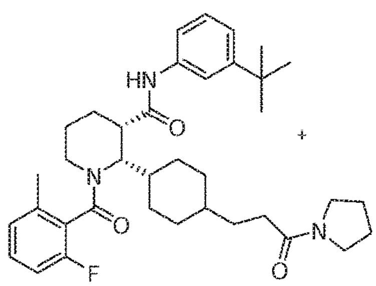 | + | 1.354 | 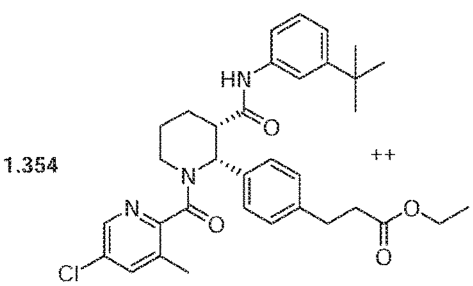 | ++ |
| 1.355 | 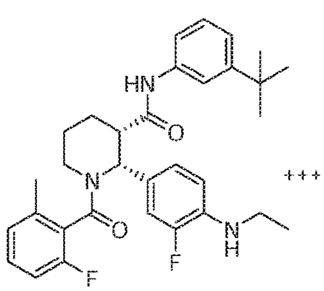 | +++ | 1.356 | 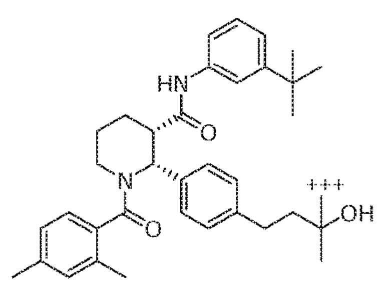 | +++ |

FIG. 1VV
| # | Structure | C5aR binding | # | Structure | C5aR binding |
|---|---|---|---|---|---|
| 1.373 | 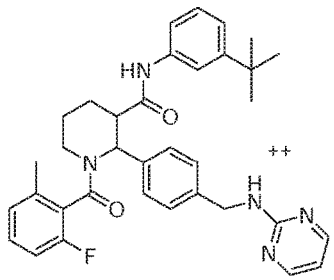 | ++ | 1.374 | 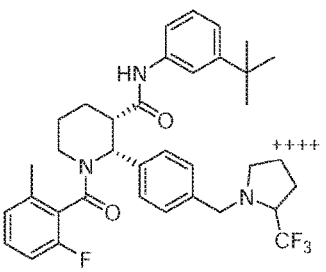 | ++++ |
| 1.375 | 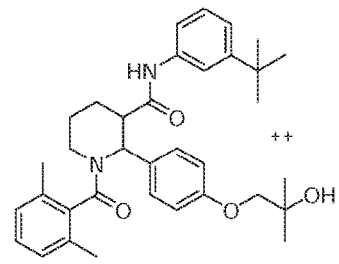 | ++ | 1.376 | 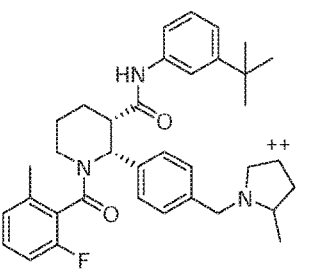 | ++ |
| 1.377 | 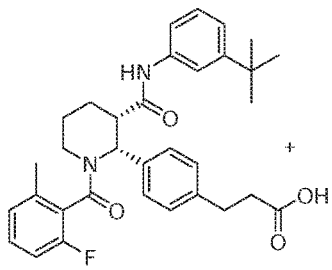 | + | 1.378 | 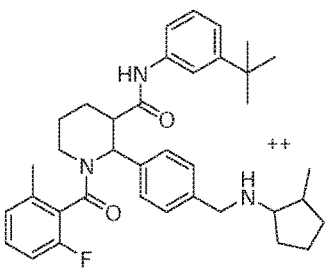 | ++ |
| 1.379 | 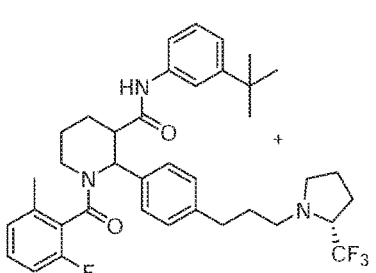 | + | 1.380 | 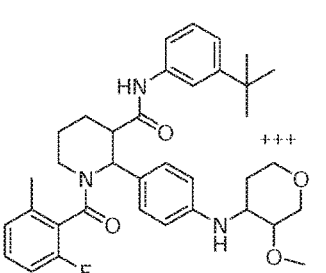 | +++ |

FIG. 1XX
| # | Structure | C5aR binding | # | Structure | C5aR binding |
|---|---|---|---|---|---|
| 1.389 | 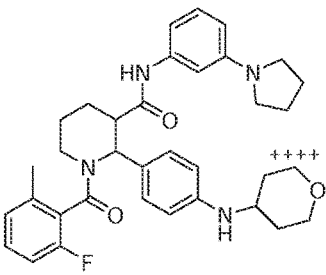 | ++++ | 1.390 | 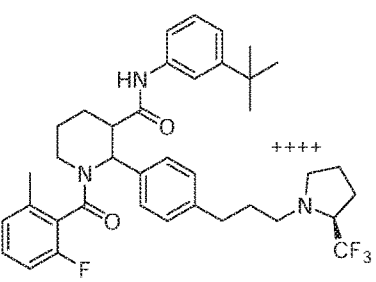 | ++++ |
| 1.391 | 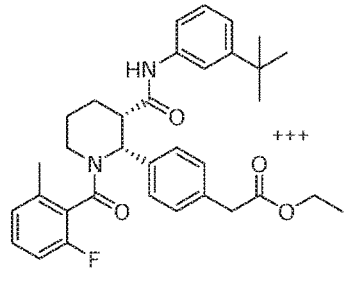 | +++ | 1.392 | 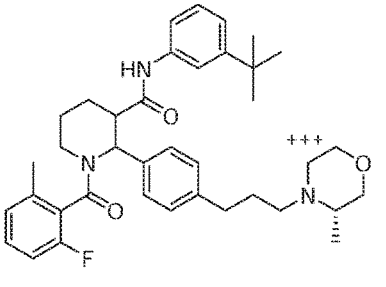 | +++ |
| 1.393 | 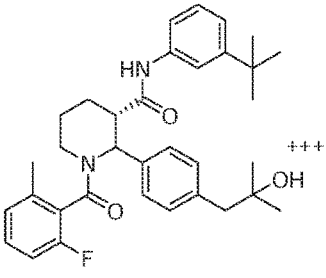 | +++ | 1.394 | 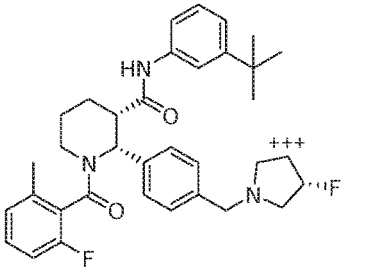 | +++ |
| 1.395 | 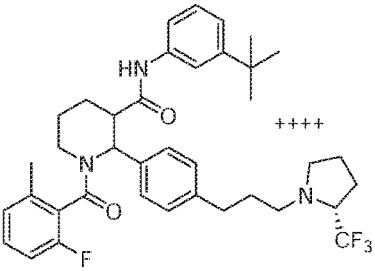 | ++++ | 1.396 | 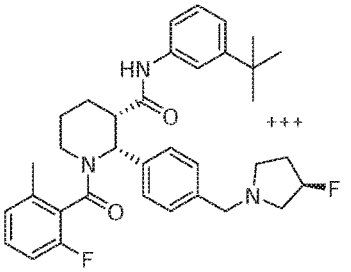 | +++ |

FIG. 1ZZ

FIG. 1AAA
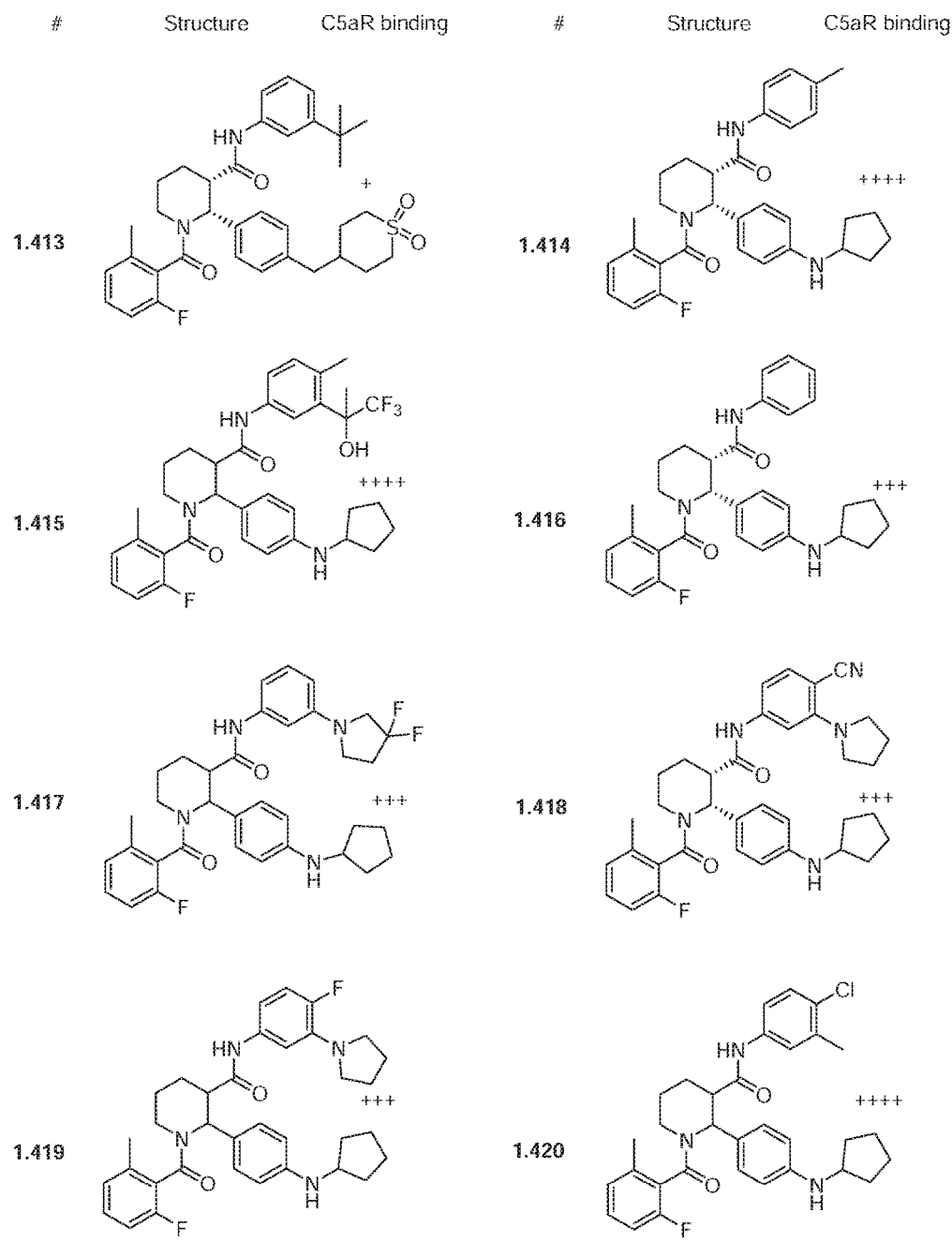

FIG. 1BBB

| # | Structure | C5aR binding | # | Structure | C5aR binding |
|---|---|---|---|---|---|
| 1.421 | 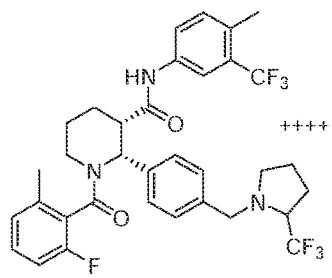 | ++++ | 1.422 | 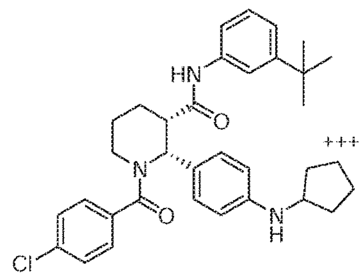 | +++ |
| 1.423 | 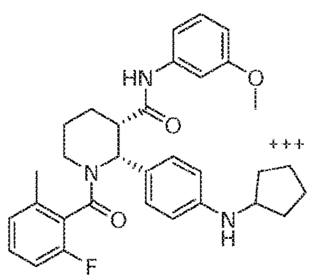 | +++ | 1.424 | 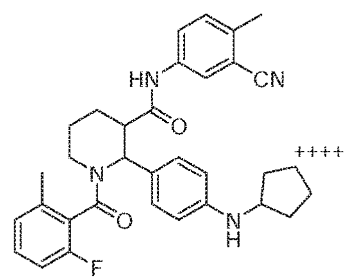 | ++++ |
| 1.425 | 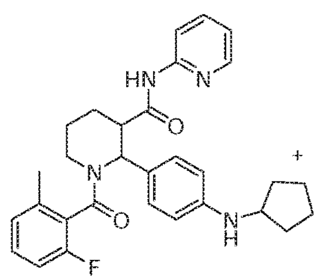 | + | 1.426 | 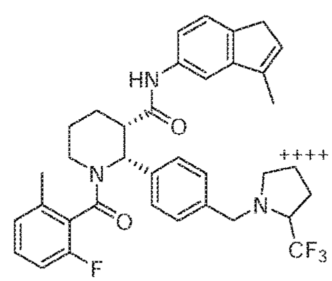 | ++++ |
| 1.427 | 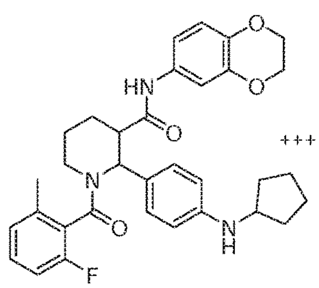 | +++ | 1.428 | 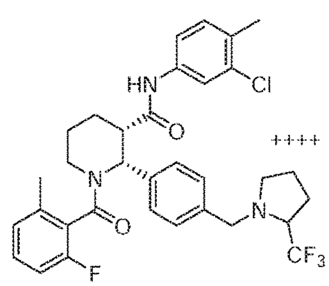 | ++++ |

FIG. 1CCC

| # | Structure | C5aR binding | # | Structure | C5aR binding |
|---|---|---|---|---|---|
| 1.429 | 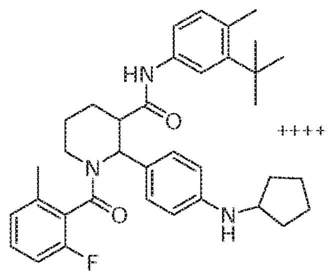 | ++++ | 1.430 | 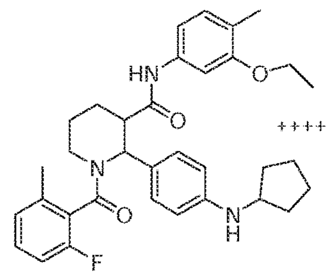 | ++++ |
| 1.431 | 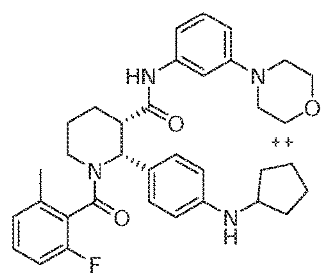 | ++ | 1.432 | 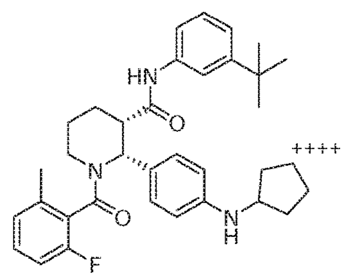 | ++++ |
| 1.433 | 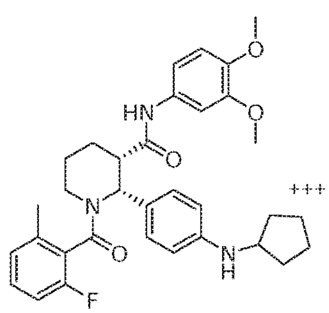 | +++ | 1.434 | 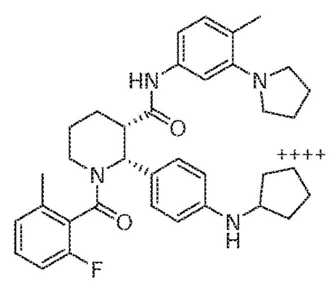 | ++++ |
| 1.435 | 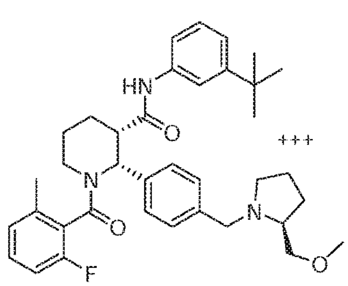 | +++ | 1.436 | 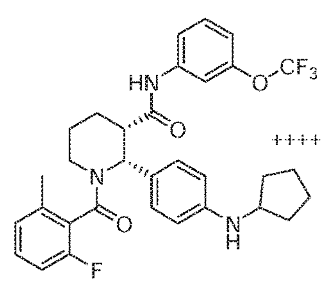 | ++++ |

FIG. 1DDD
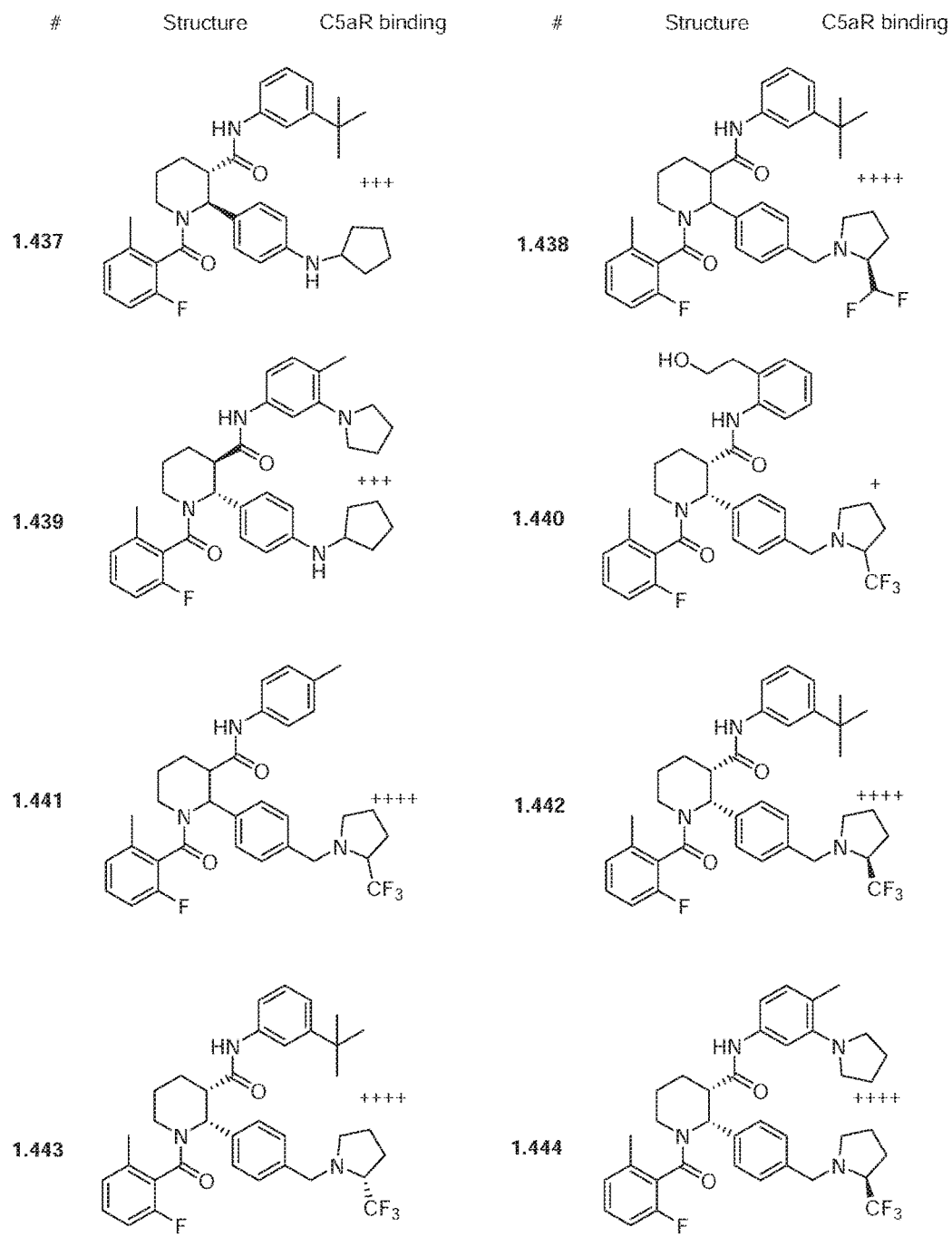

FIG. 1EEE
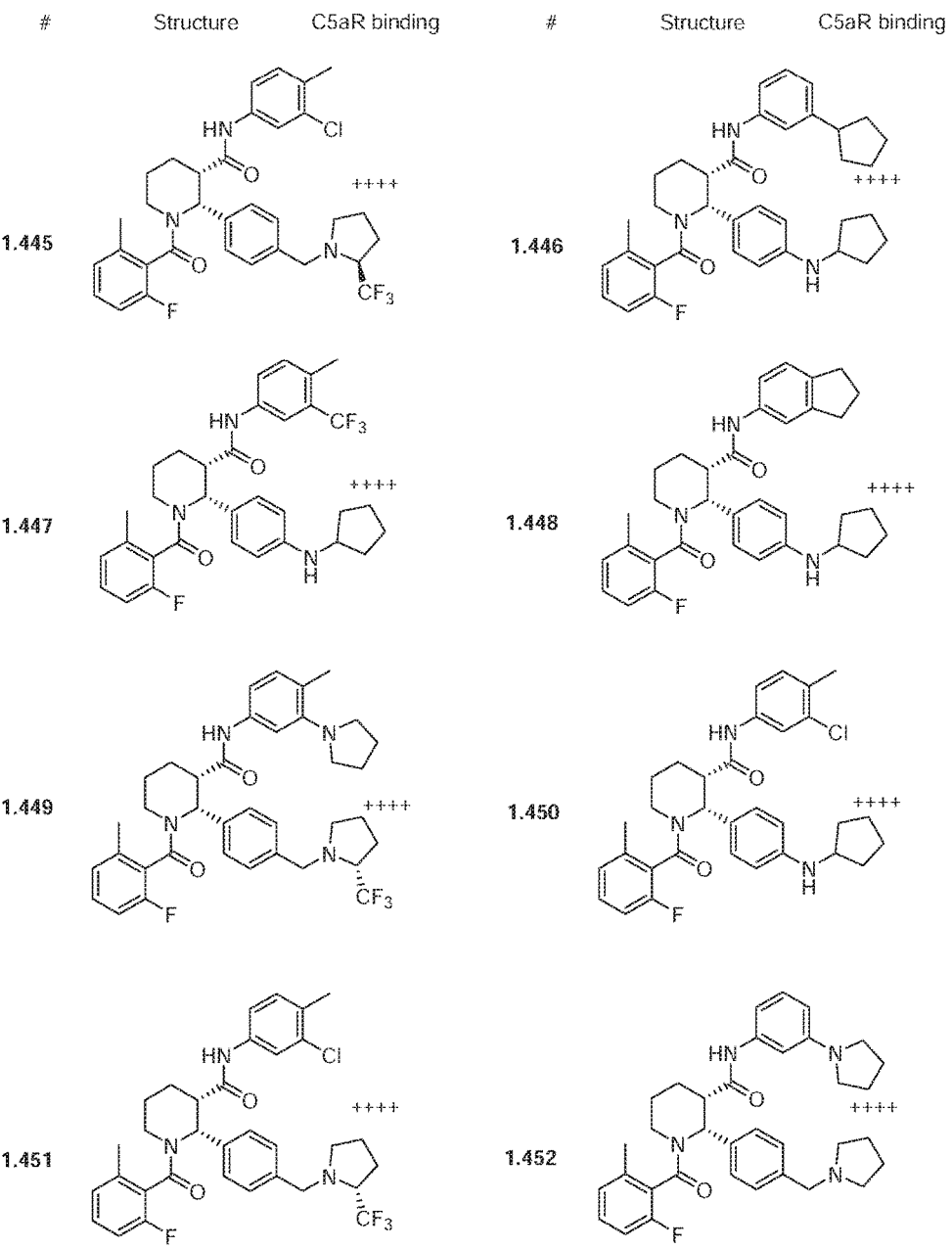

| # | Structure | C5aR binding | # | Structure | C5aR binding |
|---|---|---|---|---|---|
| 1.461 | | ++ | 1.462 | | ++++ |
| 1.463 | | ++ | 1.464 | | +++ |
| 1.465 | | ++++ | 1.466 | | ++++ |
| 1.467 | | ++++ | 1.468 | | +++ |

FIG. 1HHH
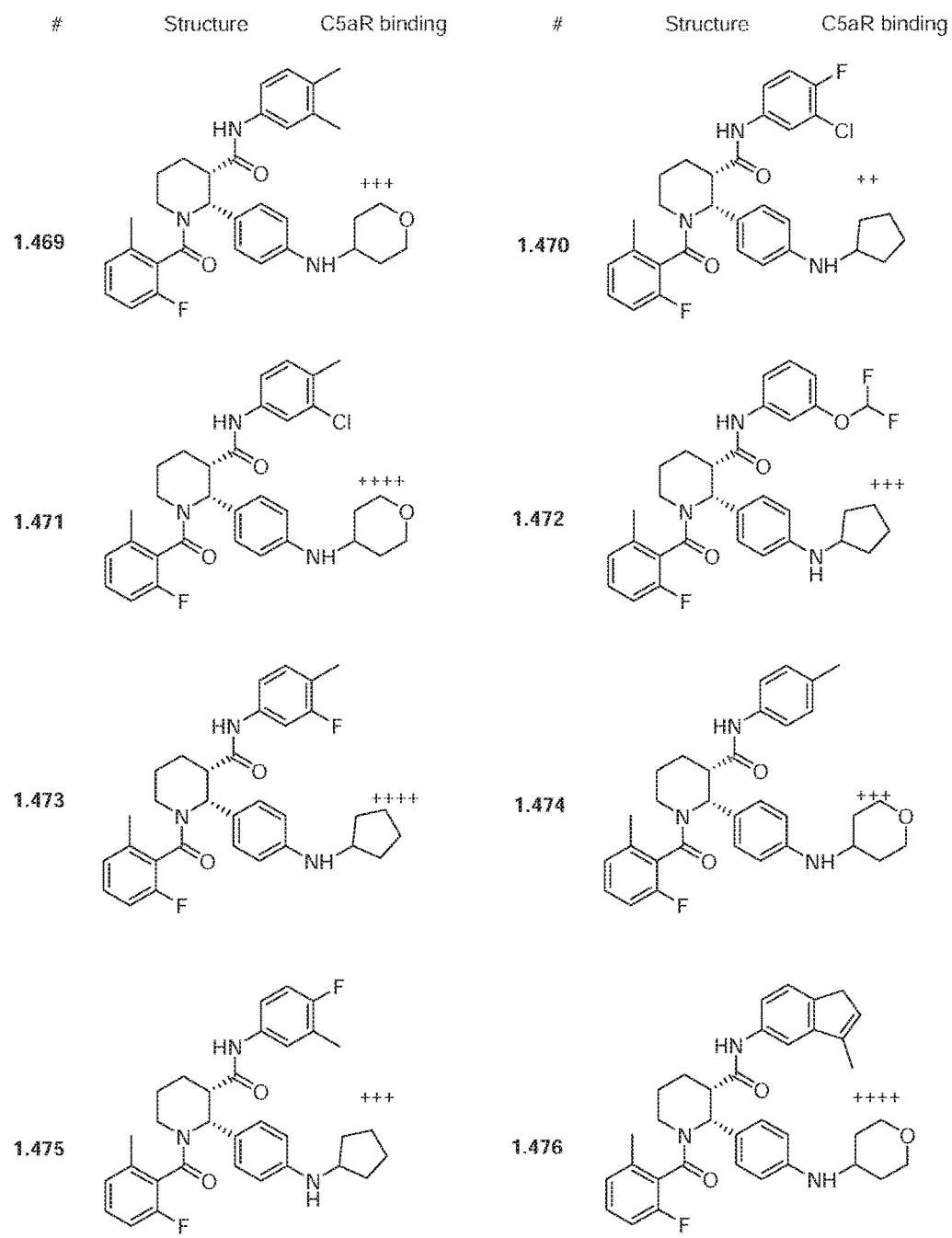

FIG. 1III
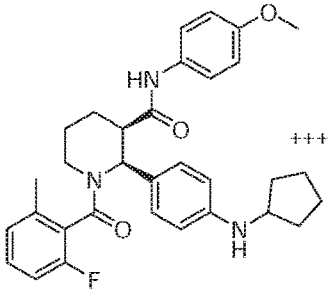

FIG. 1JJJ
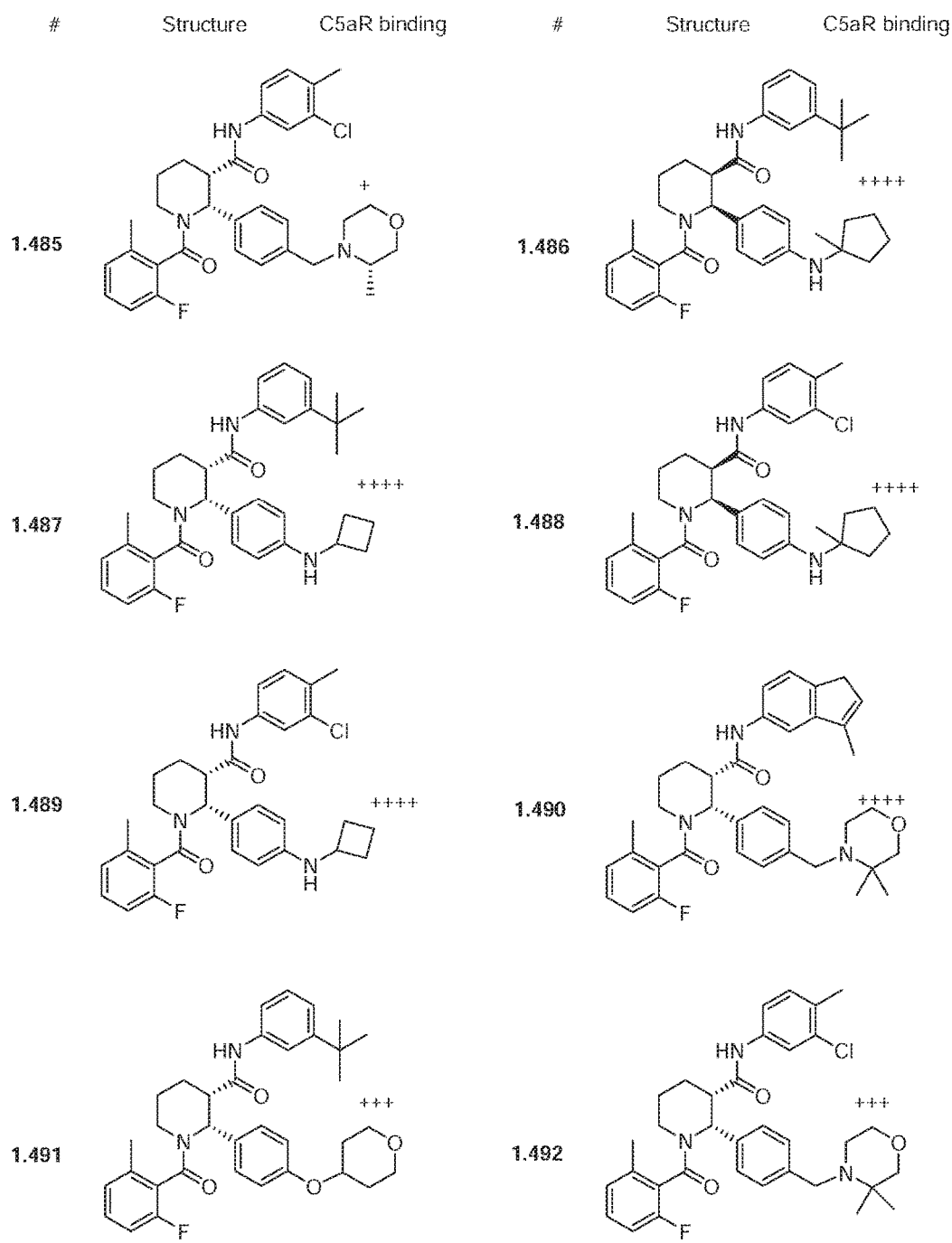

FIG. 1KKK
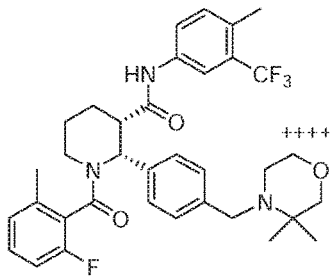

FIG. 1LLL

| # | Structure | C5aR binding | # | Structure | C5aR binding |
|---|---|---|---|---|---|
| 1.501 | 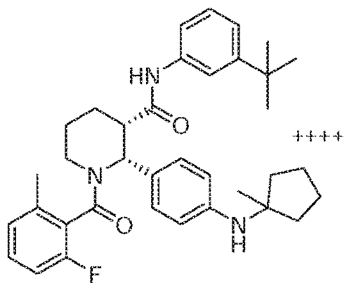 | ++++ | 1.502 | 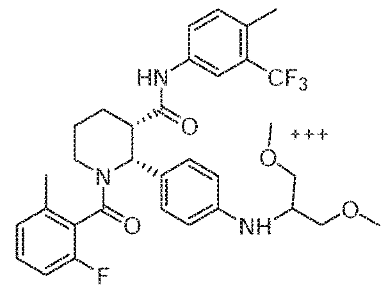 | +++ |
| 1.503 | 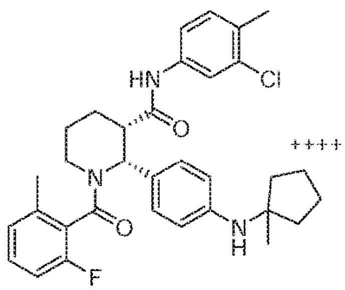 | ++++ | 1.504 | 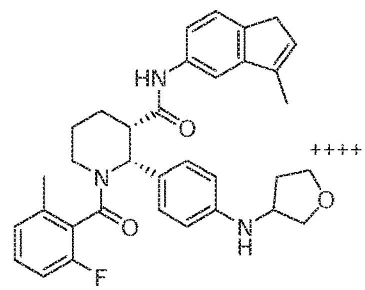 | ++++ |
| 1.505 | 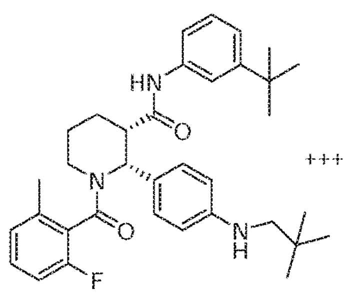 | +++ | 1.506 | 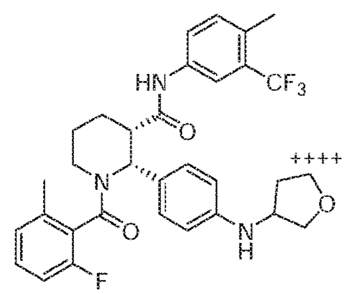 | ++++ |
| 1.507 | 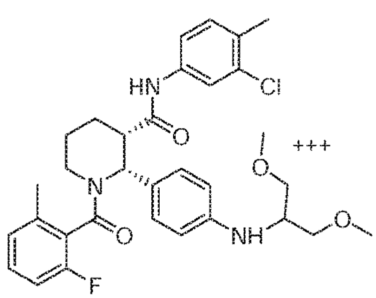 | +++ | 1.508 | 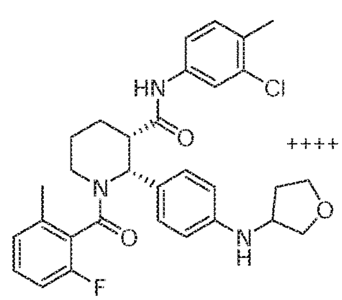 | ++++ |

FIG. 1MMM
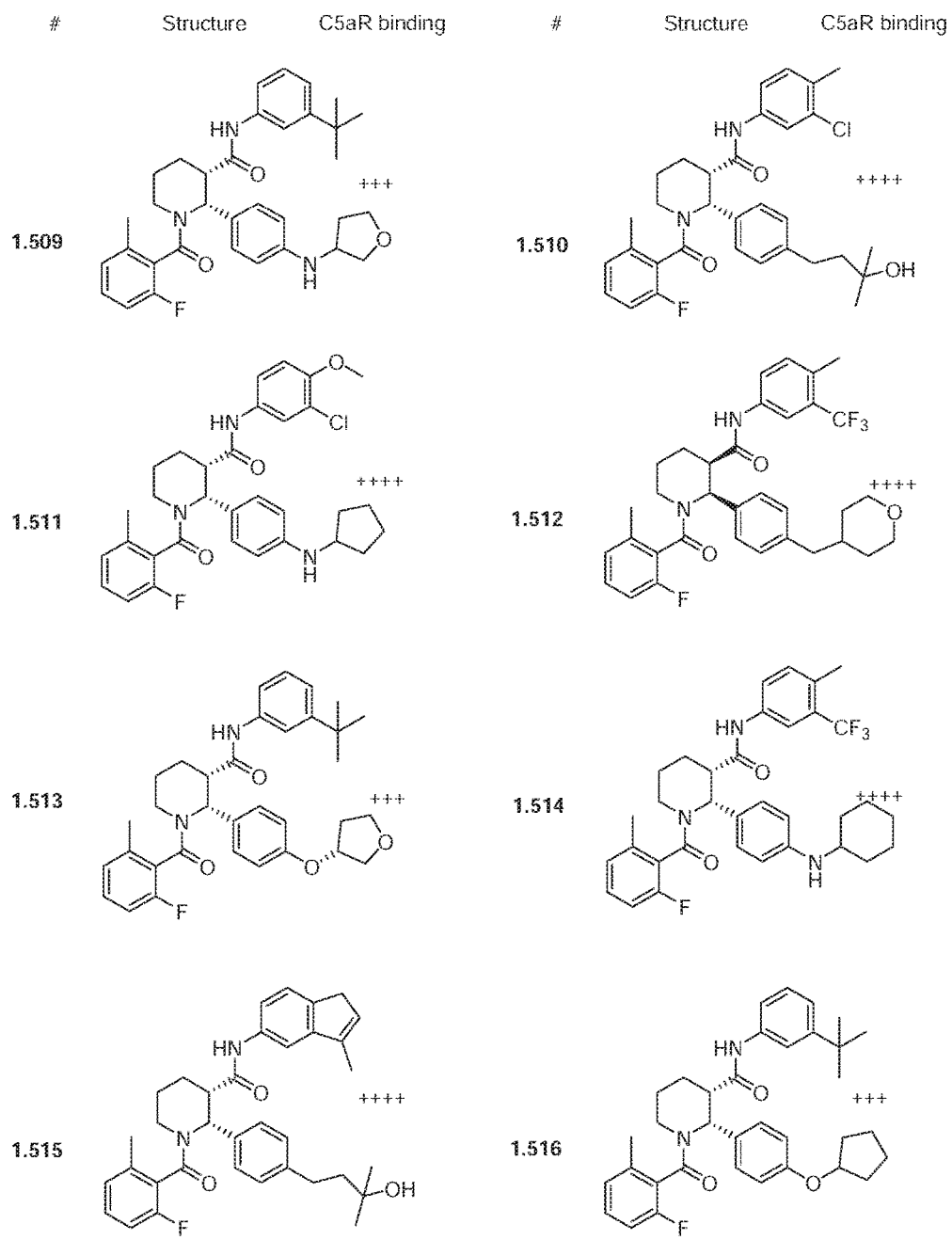

FIG. 1NNN
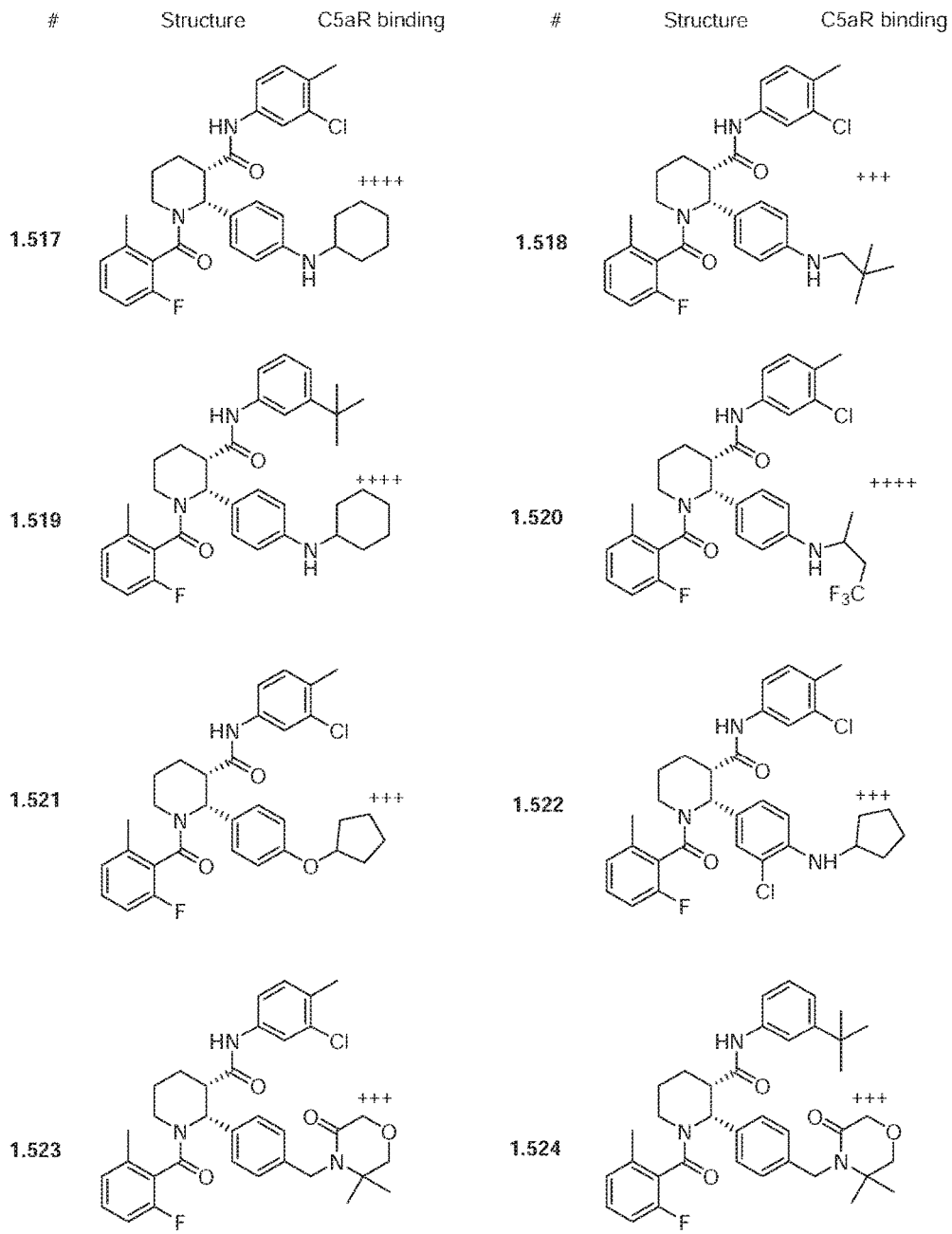

FIG. 1000

| # | Structure | C5aR binding | # | Structure | C5aR binding |
|---|---|---|---|---|---|
| 1.525 | 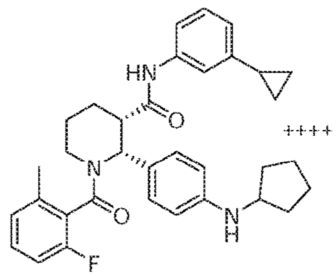 | ++++ | 1.526 | 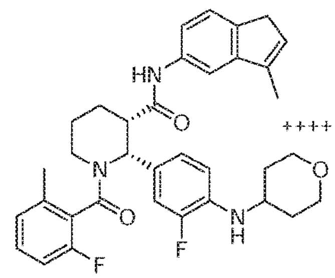 | ++++ |
| 1.527 | 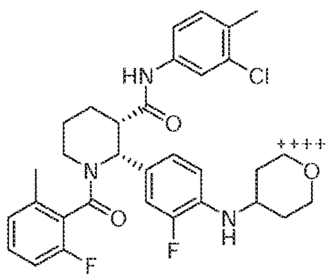 | ++++ | 1.528 | 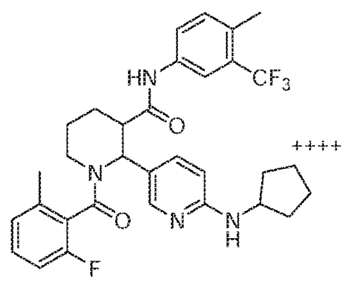 | ++++ |
| 1.529 | 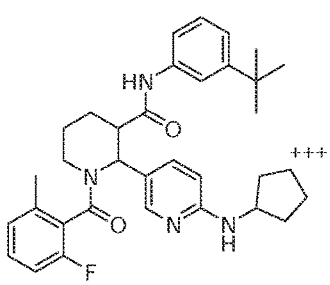 | +++ | 1.530 | 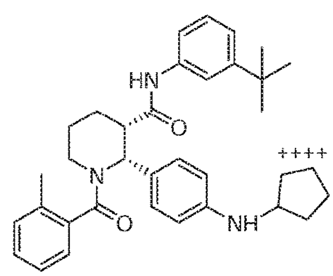 | ++++ |
| 1.531 | 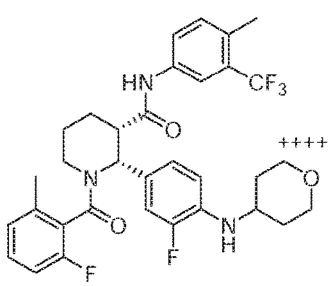 | ++++ | 1.532 | 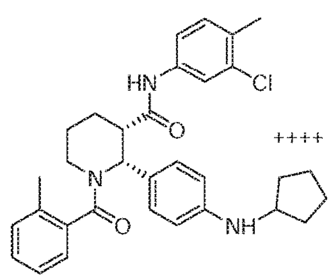 | ++++ |

FIG. 1PPP
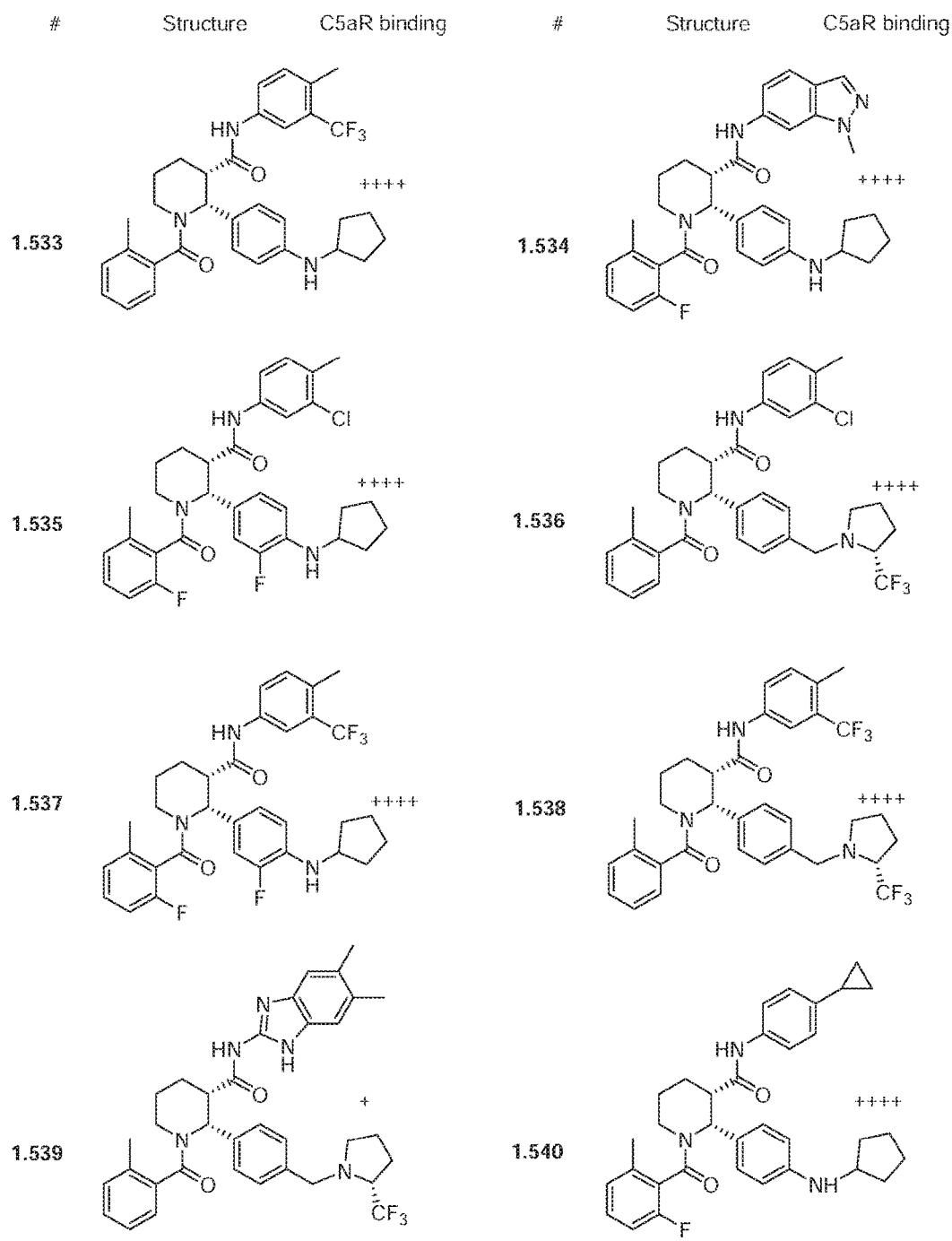

FIG. 1QQQ
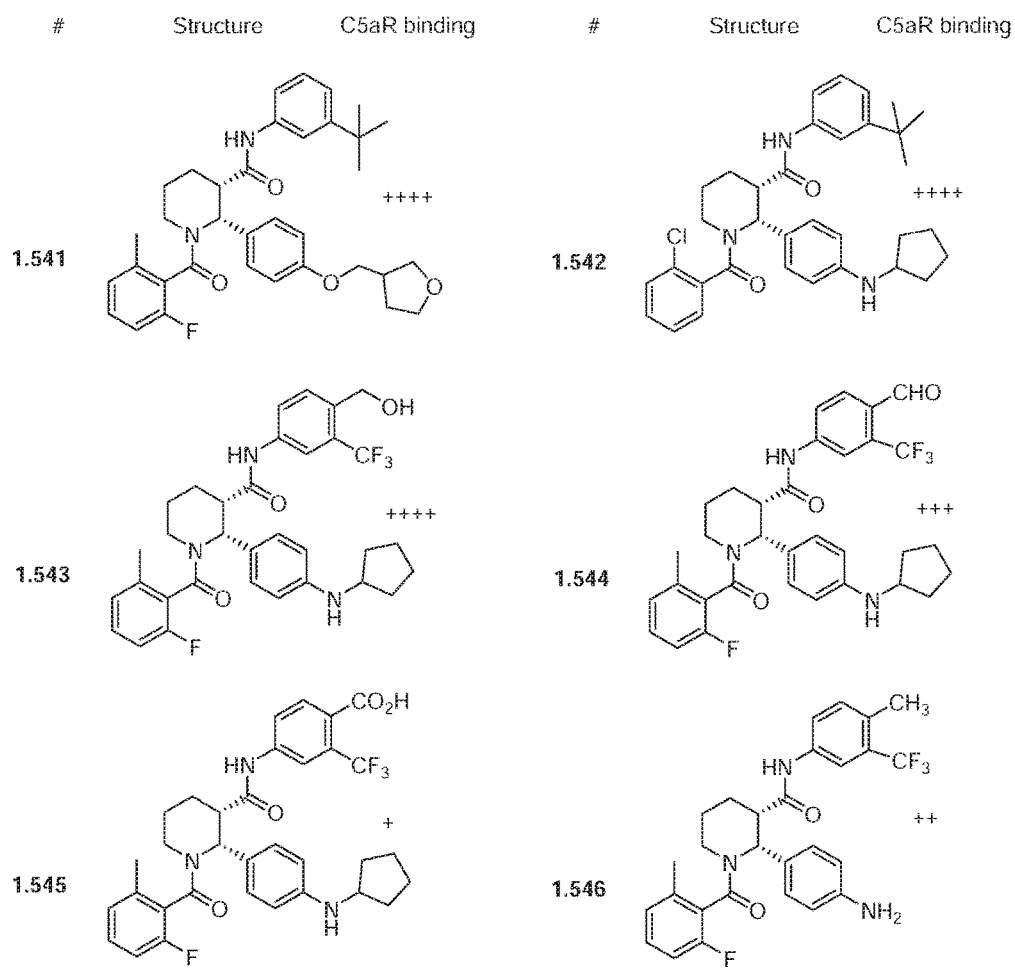

C5AR ANTAGONISTS

CROSS-REFERENCES TO RELATED APPLICATIONS

This application is a continuation of U.S. application Ser. No. 15/400,820 filed Jan. 6, 2017, which is a continuation of Ser. No. 14/846,487 filed Sep. 4, 2015 (now U.S. Pat. No. 9,573,897), which is a continuation of U.S. application Ser. No. 13/806,339 filed Mar. 8, 2013 (now U.S. Pat. No. 9,126,939), which is a U.S. 371 National Phase of International Application No. PCT/US2011/041910 filed Jun. 24, 2011, which claims priority benefit and is a continuation of U.S. application Ser. No. 12/823,039, filed Jun. 24, 2010 (abandoned), and U.S. application Ser. No. 13/072,616, filed Mar. 25, 2011 (abandoned), the contents of which are incorporated herein by reference in their entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers. In *Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a. C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, a and 3, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498 (1980)).

C5 is cleaved into the C5a and C5b fragments during activation of the complement pathways. The convertase enzymes responsible for C5 activation are multi-subunit complexes of C4b, C2a, and C3b for the classical pathway and of $(C3b)_2$, Bb, and P for the alternative pathway (Goldlust, M. B. et al., *J. Immunol.* 113: 998-1007 (1974); Schreiber, R. D. et al, *Proc. Natl. Acad. Sci.* 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. Both C5a and C3a are potent stimulators of neutrophils and monocytes (Schindler, R. et al., *Blood* 76: 1631-1638 (1990); Haeffner-Cavaillon. N. et al., *J. Immunol.* 138: 794-700 (1987); Cavaillon, J. M. et al., *Eur. J. Immunol.* 20: 253-257 (1990)).

In addition to its anaphylatoxic properties, C5a induces chemotactic migration of neutrophils (Ward, P. A. et al., *J. Immunol.* 102: 93-99 (1969)), eosinophils (Kay, A. B. et al., *Immunol.* 24: 969-976 (1973)), basophils (Lett-Brown, M. A. et al., *J. Immunol.* 117: 246-252 1976)), and monocytes (Snyderman, R. et al., *Proc. Soc. Exp. Biol. Med.* 138: 387-390 1971)). Both C5a and C5b-9 activate endothelial cells to express adhesion molecules essential for sequestration of activated leukocytes, which mediate tissue inflammation and injury (Foreman, K. E. et al., *J. Clin. Invest.* 94: 1147-1155 (1994); Foreman, K. E. et al., *Inflammation* 20: 1-9 (1996); Rollins, S. A. et al., *Transplantation* 69: 1959-1967 (2000)). C5a also mediates inflammatory reactions by causing smooth muscle contraction, increasing vascular permeability, inducing basophil and mast cell degranulation and inducing release of lysosomal proteases and oxidative free radicals (Gerard, C. et al., *Ann. Rev. Immunol.* 12: 775-808 (1994)). Furthermore, C5a modulates the hepatic acute-phase gene expression and augments the overall immune response by increasing the production of TNF-α, IL-1-β, IL-6, IL-8, prostaglandins and leukotrienes (Lambris, J. D. et al., In: *The Human Complement System in Health and Disease*, Volanakis, J. E. ed., Marcel Dekker, New York, pp. 83-118).

The anaphylactic and chemotactic effects of C5a are believed to be mediated through its interaction with the C5a receptor. The human C5a receptor (C5aR) is a 52 kD membrane bound G protein-coupled receptor, and is expressed on neutrophils, monocytes, basophils, eosinophils, hepatocytes, lung smooth muscle and endothelial cells, and renal glomerular tissues (Van-Epps, D. E. et al., *J. Immunol.* 132: 2862-2867 (1984); Haviland, D. L. et al., *J. Immunol.* 154:1861-1869 (1995); Wetsel, R. A., *Immunol. Leff.* 44: 183-187 (1995); Buchner, R. R. et al., *J. Immunol.* 155: 308-315 (1995); Chenoweth, D. E. et al., *Proc. Natl. Acad. Sci.* 75: 3943-3947 (1978); Zwimer, J. et al., *Mol. Immunol.* 36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxy-terminal end (amino acids 62-74) (Wetsel, R. A., *Curr. Opin. Immunol.* 7: 48-53 (1995)).

C5a plays important roles in inflammation and tissue injury. In cardiopulmonary bypass and hemodialysis, C5a is formed as a result of activation of the alternative complement pathway when human blood makes contact with the artificial surface of the heart-lung machine or kidney dialysis machine (Howard, R. J. et al., *Arch. Surg.* 123: 1496-1501 (1988); Kirklin, J. K. et al., *J. Cardiovasc. Surg.* 86: 845-857 (1983); Craddock, P. R. et al., *N. Engl. J. Med.* 296: 769-774 (1977)). C5a causes increased capillary permeability and edema, bronchoconstriction, pulmonary vasoconstriction, leukocyte and platelet activation and infiltration to tissues, in particular the lung (Czermak, B. J. et al., *J. Leukoc. Biol.* 64: 40-48 (1998)). Administration of an anti-C5a monoclonal antibody was shown to reduce cardiopulmonary bypass and cardioplegia-induced coronary endothelial dysfunction (Tofukuji, M. et al., *J. Thorac. Cardiovasc. Surg.* 116: 1060-1068 (1998)).

C5a is also involved in acute respiratory distress syndrome (ARDS), Chronic Obstructive Pulmonary Disorder (COPD) and multiple organ failure (MOF) (Hack, C. E. et al., *Am. J. Med.* 1989: 86: 20-26; Hammerschmidt D E et al. *Lancet* 1980; 1: 947-949: Heideman M. et al. *J. Trauma* 1984; 4: 1038-1043; Marc, M M, et al., *Am. J. Respir. Cell and Mol. Biol.,* 2004: 31: 216-219). C5a augments monocyte production of two important pro-inflammatory cytokines. TNF-α and IL-1. C5a has also been shown to play an important role in the development of tissue injury, and particularly pulmonary injury, in animal models of septic shock (Smedegard G et al. *Am. J. Pathol.* 1989; 135: 489-497: Markus, S., et al., *FASEB Journal* (2001), 15: 568-570). In sepsis models using rats, pigs and non-human primates, anti-C5a antibodies administered to the animals before treatment with endotoxin or *E. coli* resulted in decreased tissue injury, as well as decreased production of IL-6 (Smedegard, G. et al., *Am. J. Pathol.* 135: 489-497 (1989): Hopken, U. et al., *Eur. J. Immunol.* 26: 1103-1109 (1996): Stevens, J. H. et al., *J. Clin. Invest.* 77: 1812-1816 (1986)). More importantly, blockade or C5a with anti-C5a polyclonal antibodies has been shown to significantly improve survival rates in a caecal ligation/puncture model of sepsis in rats (Czermak, B. J. et al., Nat. Med. 5: 788-792 (1999)). This model share many aspects of the clinical manifestation of sepsis in humans. (Parker, S. J. et al., *Br. J. Surg.* 88: 22-30 (2001)). In the same sepsis model, anti-C5a antibodies were shown to inhibit apoptosis of thymocytes (Guo, R. F. et al., *J. Clin. Invest.* 106: 1271-1280 (2000)) and prevent MOF (Huber-Lang, M. et al., *J. Immunol.* 166: 1193-1199 (2001)). Anti-C5a antibodies were also protective in a cobra venom factor model of lung injury in rats, and in immune complex-induced lung injury (Mulligan, M. S. et al. *J. Clin. Invest.* 98: 503-512 (1996)). The importance of C5a in immune complex-mediated lung injury was later confirmed in mice (Bozic, C. R. et al., *Science* 26: 1103-1109 (1996)).

C5a is found to be a major mediator in myocardial ischemia-reperfusion injury. Complement depletion reduced myocardial infarct size in mice (Weisman, H. F. et al., *Science* 249: 146-151 (1990)), and treatment with anti-C5a antibodies reduced injury in a rat model of hindlimb ischemia-reperfusion (Bless, N. M. et al., *Am. J. Physiol.* 276: L57-L63 (1999)). Reperfusion injury during myocardial infarction was also markedly reduced in pigs that were retreated with a monoclonal anti-C5a IgG (Amsterdam, E. A. et al., *Am. J. Physiol.* 268:H448-H457 (1995)). A recombinant human C5aR antagonist reduces infarct size in a porcine model of surgical revascularization (Riley, R. D. et al., *J. Thorac. Cardiovasc. Surg.* 120: 350-358 (2000)).

C5a driven neutrophils also contribute to many bullous diseases (e.g., bullous pemphigoid, pemphigus vulgaris and pemphigus foliaceus). These are chronic and recurring inflammatory disorders clinically characterized by sterile blisters that appear in the sub-epidermal space of the skin and mucosa. While autoantibodies to keratinocytes located at the cutaneous basement membranes are believed to underlie the detachment of epidermal basal keratinocytes from the underlying basement membrane, blisters are also characterized by accumulation of neutrophils in both the upper dermal layers and within the blister cavities. In experimental models a reduction of neutrophils or absence of complement (total or C5-selective) can inhibit formation of sub-epidermal blisters, even in the presence of high auto-antibody titers.

Complement levels are elevated in patients with rheumatoid arthritis (Jose, P. J. et al., *Ann. Rheum. Dis.* 49: 747-752 (1990): Grant, E. P., et al., *J. of Exp. Med.,* 196(11): 1461-1471, (2002)), lupus nephritis (Bao, L., et al., *Eur. J. of Immunol.,* 35(8), 2496-2506, (2005)) and systemic lupus erythematosus (SLE) (Porcel, J. M. et al., *Clin. Immunol. Immunopathol.* 74: 283-288 (1995)). C5a levels correlate with the severity of the disease state. Collagen-induced arthritis in mice and rats resembles the rheumatoid arthritic disease in human. Mice deficient in the C5a receptor demonstrated a complete protection from arthritis induced by injection of monoclonal anti-collagen Abs (Banda, N. K., et al., *J. of Immunol.,* 2003, 171: 2109-2115). Therefore, inhibition of C5a and/or C5a receptor (C5aR) could be useful in treating these chronic diseases.

The complement system is believed to be activated in patients with inflammatory bowel disease (IBD) and is thought to play a role in the disease pathogenesis. Activated complement products were found at the luminal face of surface epithelial cells, as well as in the muscularis mucosa and submucosal blood vessels in IBD patients (Woodruff, T. M., et al., *J of Immunol.,* 2003, 171: 5514-5520).

C5aR expression is upregulated on reactive astrocytes, microglia, and endothelial cells in an inflamed human central nervous system (Gasque, P. et al., *Am. J. Pathol.* 150: 31-41 (1997)). C5a might be involved in neurodegenerative diseases, such as Alzheimer disease (Mukherjee, P. et al., *J. Neuroimmunol.* 105: 124-130 (2000); O'Barr, S. et al., *J. Neuroimmunol.* (2000) 105: 87-94; Farkas, I., et al. *J. Immunol.* (2003) 170:5764-5771), Parkinson's disease, Pick disease and transmissible spongiform encephalopathies. Activation of neuronal C5aR may induce apoptosis (Farkas I et al. *J. Physiol.* 1998; 507: 679-687). Therefore, inhibition of C5a and/or C5aR could also be useful in treating neurodegenerative diseases.

There is some evidence that C5a production worsens inflammation associated with atopic dermatitis (Neuber, K., et al., *Immunology* 73:83-87, (1991)), and chronic urticaria (Kaplan, A. P., *J. Allergy Clin. Immunol.* 114; 465-474, (2004).

Psoriasis is now known to be a T cell-mediated disease (Gottlieb, E. L. et al., *Nat. Med.* 1: 442-447 (1995)). However, neutrophils and mast cells may also be involved in the pathogenesis of the disease (Terui, T. et al., *Exp. Dermatol.* 9: 1-10; 2000); Werfel, T. et al., *Arch. Dermatol. Res.* 289: 83-86 (1997)). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. T cells and neutrophils are chemo-attracted by C5a (Nataf, S. et al., *J. Immunol.* 162: 4018-4023 (1999); Tsuji, R. F. et al., *J. Immunol.* 165: 1588-1598 (2000); Cavaillon, J. M. et al., *Eur. J. Immunol.* 20: 253-257 (1990)). Additionally expression of C5aR has been demonstrated in plasmacytoid dendritic cells (pDC) isolated from lesions of cutaneous lupus erythematous and these cells were shown to display chemotactic behavior towards C5a, suggesting that blockade of C5aR on pDC might be efficacious in reducing pDC infiltration into inflamed skin in both SLE and psoriasis. Therefore C5a could be an important therapeutic target for treatment of psoriasis.

Immunoglobulin G-containing immune complexes (IC) contribute to the pathophysiology in a number of autoimmune diseases, such as systemic lupus erthyematosus, rheumatoid arthritis, Sjogren's disease, Goodpasture's syndrome, and hypersensitivity pneumonitis (Madaio, M. P., *Semin. Nephrol.* 19: 48-56 (1999); Korganow, A. S. et al., *Immunity* 10: 451-459 (1999); Bolten, W. K., *Kidney Int.* 50: 1754-1760 (1996); Ando, M. et al., *Curr. Opin. Pulm. Med.* 3: 391-399 (1997)). These diseases are highly heterogeneous and generally affect one or more of the following organs: skin, blood vessels, joints, kidneys, heart, lungs, nervous system and liver (including cirrhosis and liver fibrosis). The classical animal model for the inflammatory response in these IC diseases is the Arthus reaction, which features the infiltration of polymorphonuclear cells, hemorrhage, and plasma exudation (Arthus, M., *C. R. Soc. Biol.* 55: 817-824 (1903)). Recent studies show that C5aR deficient mice are protected from tissue injury induced by IC (Kohl, J. et al., *Mol. Immunol.* 36: 893-903 (1999): Baumann, U. et al., *J. Immunol.* 164: 1065-1070 (2000)). The results are consistent with the observation that a small peptidic anti-C5aR antagonist inhibits the inflammatory response caused by IC deposition (Strachan, A. J. et al., *J. Immunol.* 164: 6560-6565 (2000)). Together with its receptor, C5a plays an important role in the pathogenesis of IC diseases. Inhibitors of C5a and C5aR could be useful to treat these diseases.

DESCRIPTION OF RELATED ART

Only recently have non-peptide based C5a receptor antagonists been described in the literature (e.g., Sumichika, H., et al., *J. Biol. Chem.* (2002), 277, 49403-49407). Non-peptide based C5a receptor antagonist have been reported as being effective for treating endotoxic shock in rats (Strachan, A. J., et al., *J. of Immunol.* (2000), 164(12): 6560-6565); and for treating IBD in a rat model (Woodruff, T. M., et al., *J of Immunol.*, 2003, 171: 5514-5520). Non-peptide based C5a receptor modulators also have been described in the patent literature by Neurogen Corporation, (e.g., WO2004/043925. WO2004/018460, WO2005/007087, WO03/082826, WO03/08828, WO02/49993, WO03/084524); Dompe S.P.A. (WO02/029187); and The University of Queenland (WO2004/100975).

There is considerable experimental evidence in the literature that implicates increased levels of C5a with a number of diseases and disorders, in particular in autoimmune and inflammatory diseases and disorders. Thus, there remains a need in the art for new small organic molecule modulators, e.g., agonists, preferably antagonists, partial agonists, of the C5a receptor (C5aR) that are useful for inhibiting pathogenic events, e.g., chemotaxis, associated with increased levels anaphylatoxin activity. The present invention fulfills this and other needs.

BRIEF SUMMARY OF THE INVENTION

In one aspect, the present invention provides compounds having the formula:

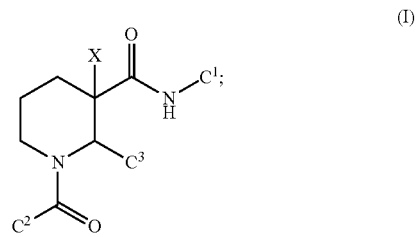

(I)

and pharmaceutically acceptable salts, hydrates and rotomers thereof: wherein $C^1$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^1$ substituents;

$C^2$ is selected from the group consisting of aryl and heteroaryl, wherein the heteroaryl group has from 1-3 heteroatoms as ring members selected from N, O and S: and wherein said aryl and heteroaryl groups are optionally substituted with from 1 to 3 $R^2$ substituents;

$C^3$ is selected from the group consisting of $C_{1-8}$ alkyl or heteroalkyl, $C_{3-8}$ cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-C14 alkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^3$ substituents;

each $R^1$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aC(O)NR^aR^b$, —$NR^aR^b$, —$OR^a$—, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^c$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;

each $R^2$ is independently selected from the group consisting of halogen, —CN, —NO$_2$, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$C(O)NR$^d$R$^e$, —NR$^d$R$^e$, —OR$^d$, and —S(O)$_2$NR$^d$R$^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S. and is optionally substituted with one or two oxo; each $R^f$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;

each $R^3$ is independently selected from the group consisting of halogen, —CN, —R$^i$, —CO$_2$R$^g$, —CONR$^g$R$^h$, —C(O)R$^g$, —C(O)R$^i$, —OC(O)NR$^g$R$^h$, —NR$^h$C(O)R$^g$, —NR$^h$CO$_2$R$^i$, —NR$^g$C(O)NR$^g$R$^h$, —NR$^g$R$^h$, —OR$^g$, —OR$^j$, —S(O)$_2$NR$^g$R$^h$, —X$^4$—R$^j$, —NH—X$^4$—R$^j$, —O—X$^4$—R$^j$, —X$^4$—NR$^g$R$^h$, —X$^4$—NHR$^j$, —X$^4$—CONR$^g$R$^h$, —X$^4$—NR$^h$C(O)R$^g$, —X$^4$—CO$_2$R$^g$, —O—X$^4$—CO$_2$R$^g$, —NH—X$^4$—CO$_2$R$^g$, —X$^4$—NR$^h$CO$_2$R$^i$, —O—X$^4$—NR$^h$CO$_2$R$^i$, —NHR$^j$ and —NHCH$_2$R$^j$, wherein X$^4$ is a $C_{1-4}$ alkylene: each R$^g$ and R$^h$ is independently selected from hydrogen, $C_{1-8}$ alkyl or heteroalkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each R$^i$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl; and each R$^j$ is selected from the group consisting of $C_{3-6}$ cycloalkyl, imidazolyl, pyrimidinyl, pyrrolinyl, piperidinyl, morpholinyl, tetrahydrofuranyl, tetrahydropyranyl, and S,S-dioxo-tetrahydrothiopyranyl, and wherein the aliphatic and cyclic portions of R$^g$, R$^h$, R$^i$ and R$^j$ are optionally further substituted with from one to three halogen, methyl, CF$_3$, hydroxy, $C_{1-4}$ alkoxy, $C_{1-4}$ alkoxy-$C_{1-8}$ alkyl, —C(O)O—$C_{1-8}$ alkyl, amino, alkylamino and dialkylamino groups, and optionally when two R$^3$ groups are on adjacent atoms, they are combined to form a five- or six-membered ring; and X is hydrogen or CH$_3$.

In addition to the compounds provided herein, the present invention further provides pharmaceutical compositions containing one or more of these compounds, as well as methods for the use of these compounds in therapeutic methods, primarily to treat diseases associated with C5a signalling activity.

In yet another aspect, the present invention provides methods of diagnosing disease in an individual. In these methods, the compounds provided herein are administered in labeled form to a subject, followed by diagnostic imaging to determine the presence or absence of C5aR. In a related aspect, a method of diagnosing disease is carried out by contacting a tissue or blood sample with a labeled compound as provided herein and determining the presence, absence, or amount of C5aR in the sample.

DETAILED DESCRIPTION OF THE INVENTION

I. Abbreviation and Definitions

Figure 1E:
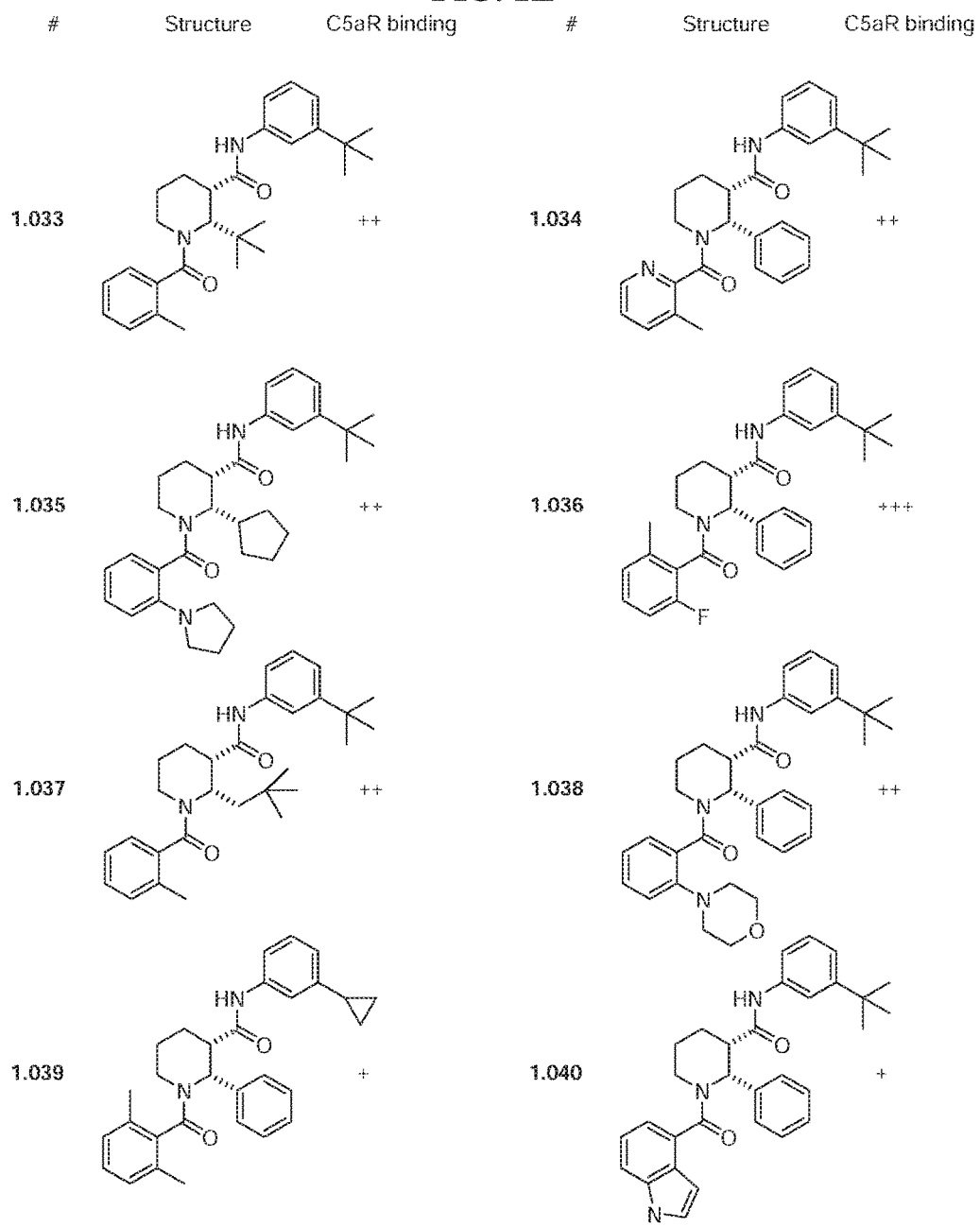
FIGS. 1A-1QQQ provide structures and activity for representative compounds of the present invention. The compounds were prepared using methods as described generally below, as well as methods provided in the Examples.
Figure 1G:
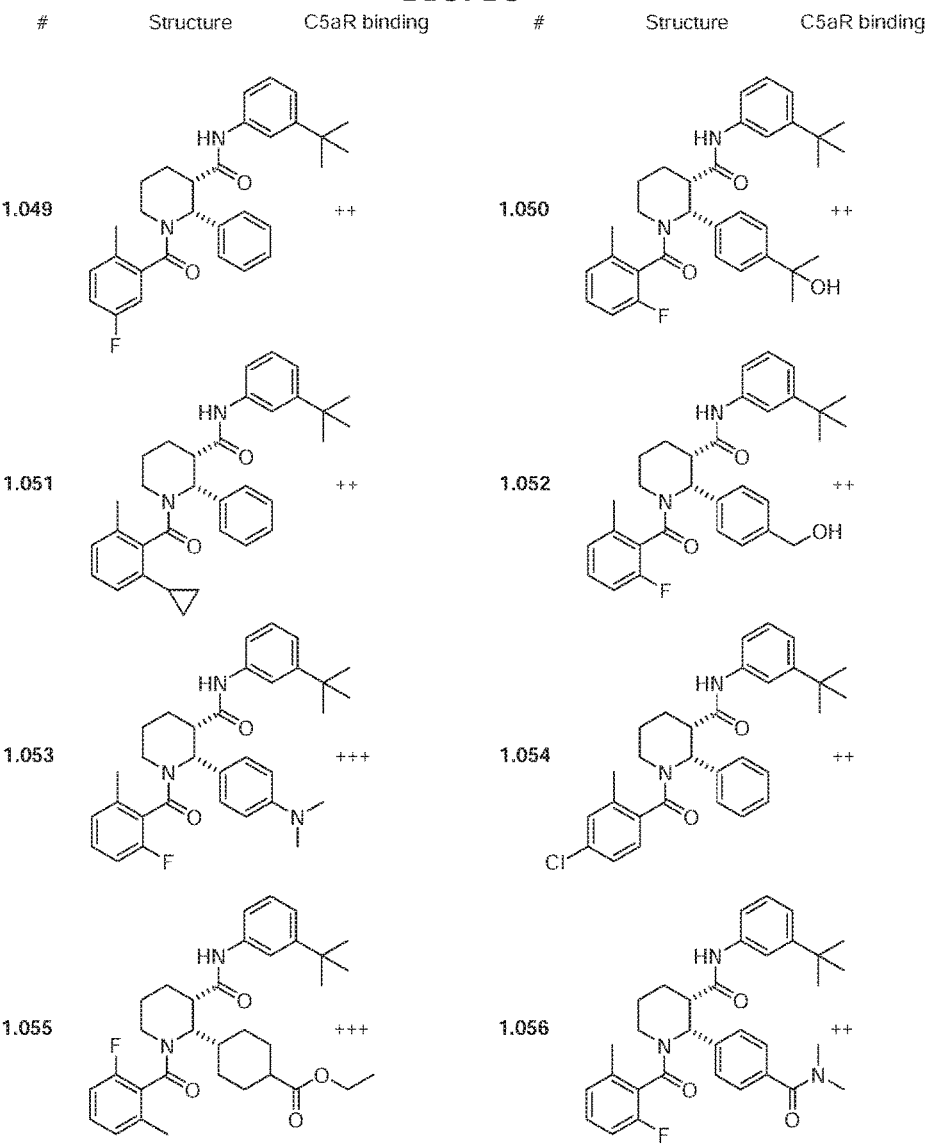
Figure 1H:
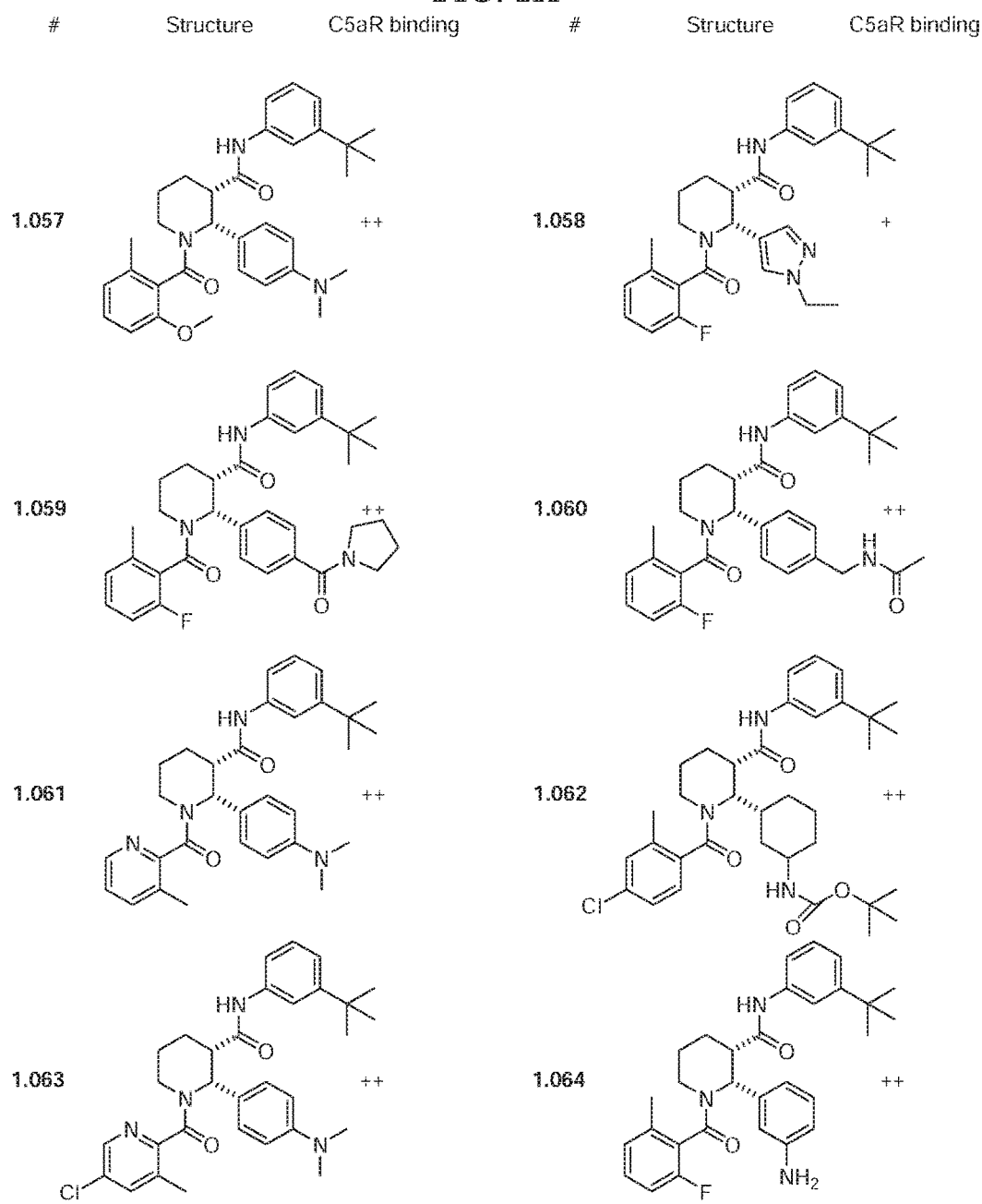
Figure 1I:
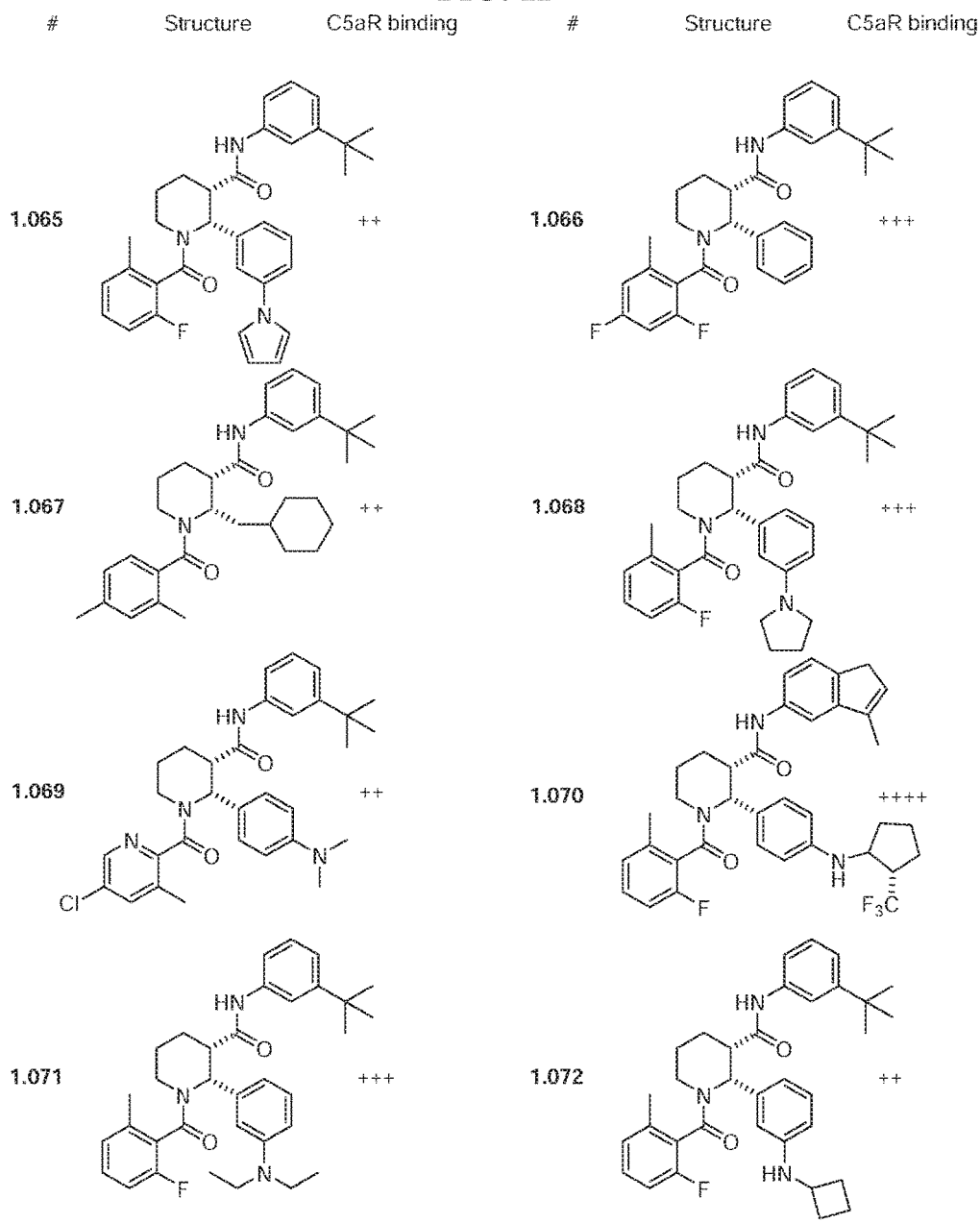
Figure 1L:
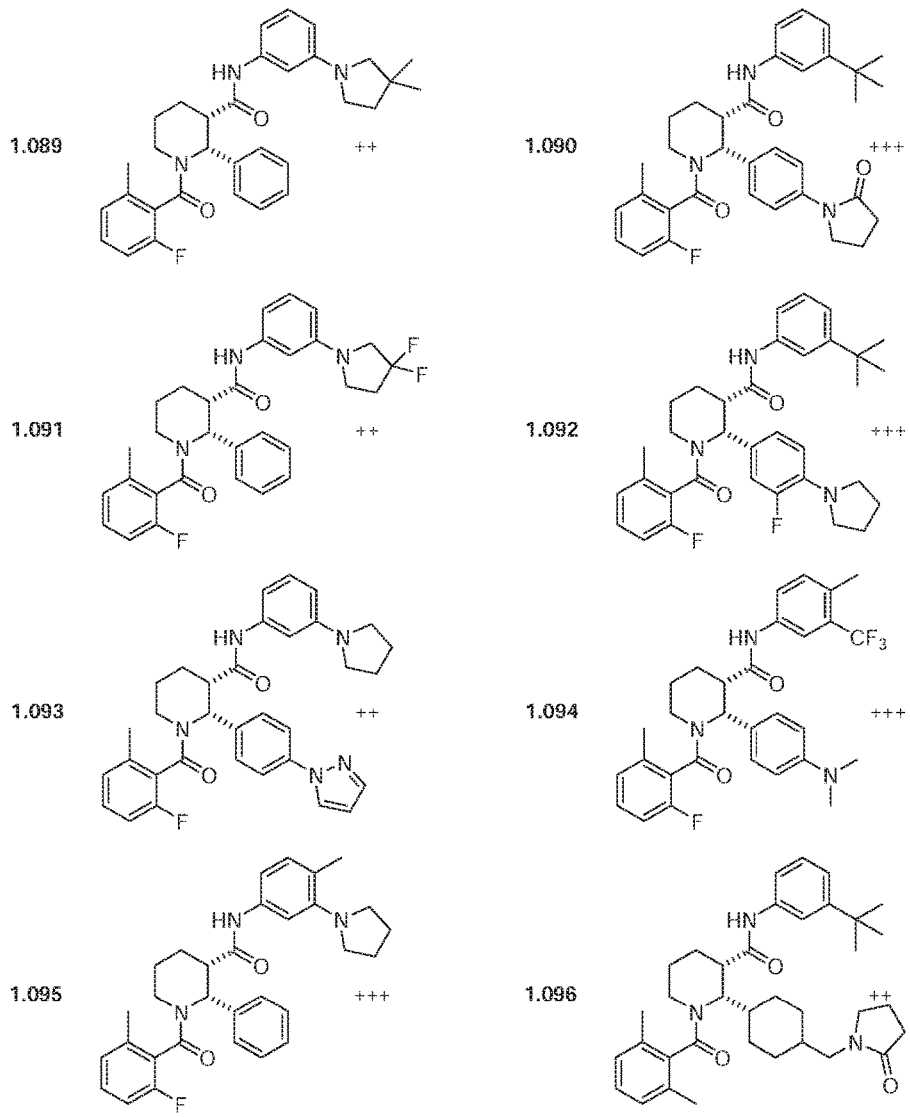
Figure 1M:
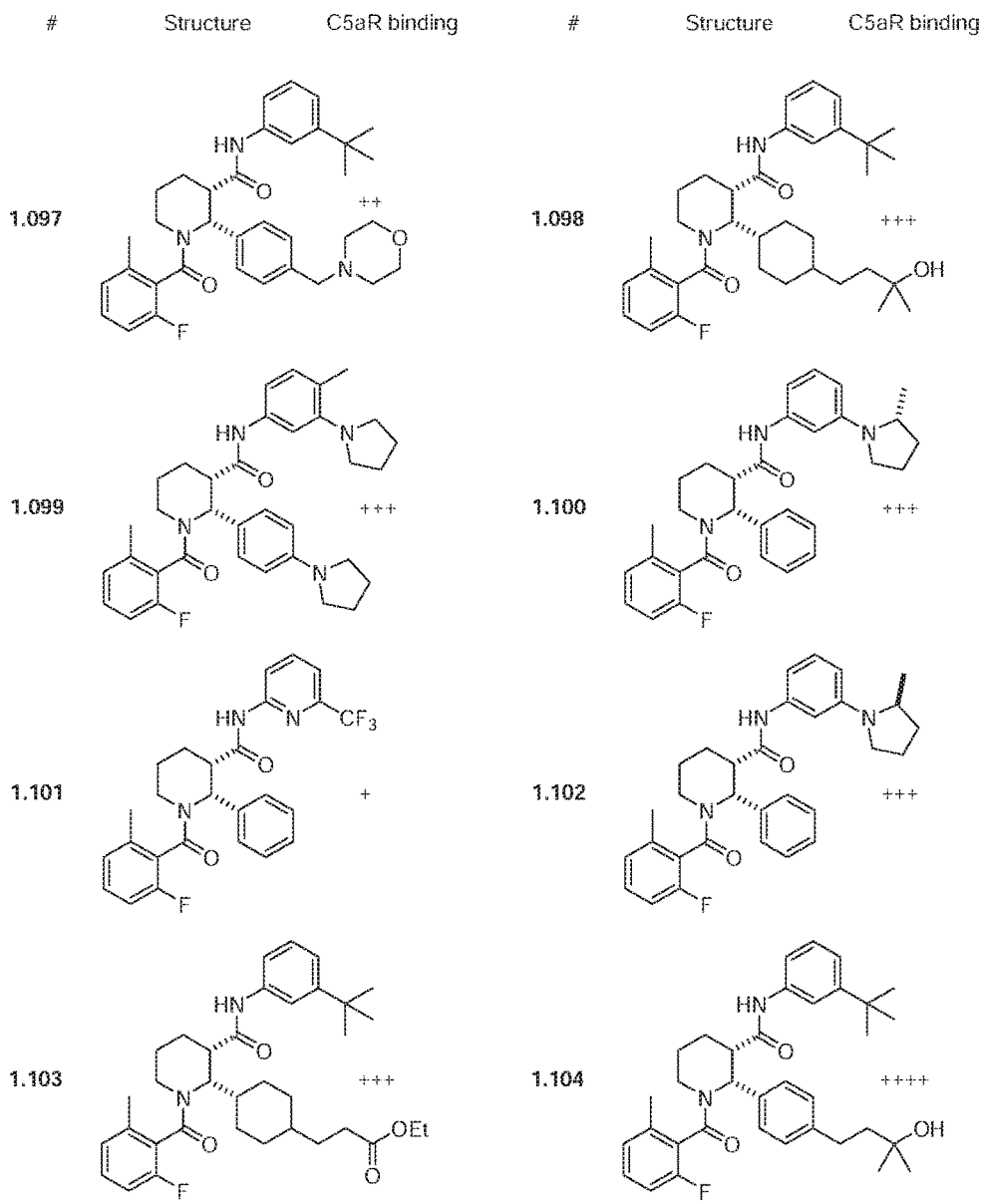
Figure 1U:
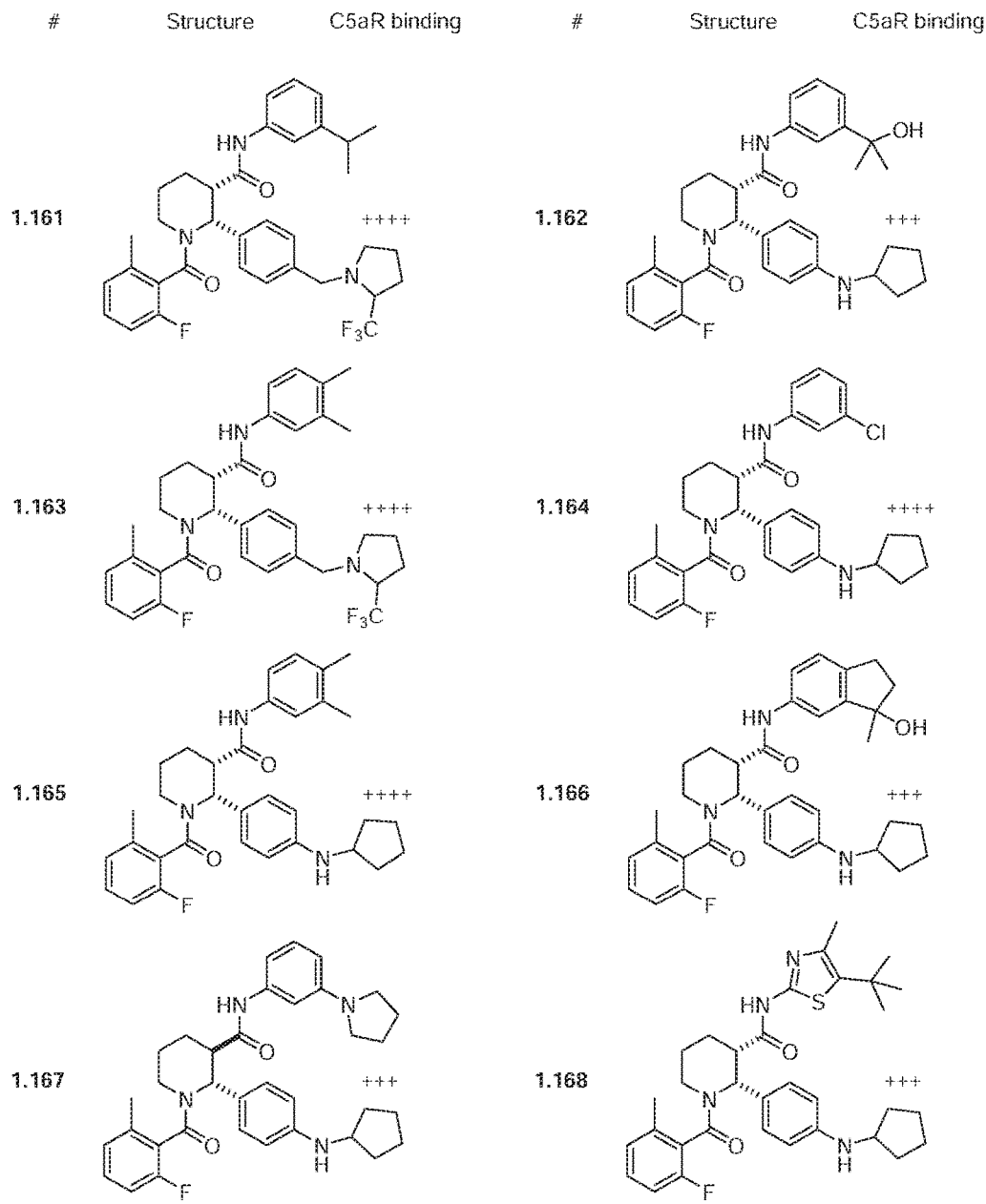
Figure 1X:
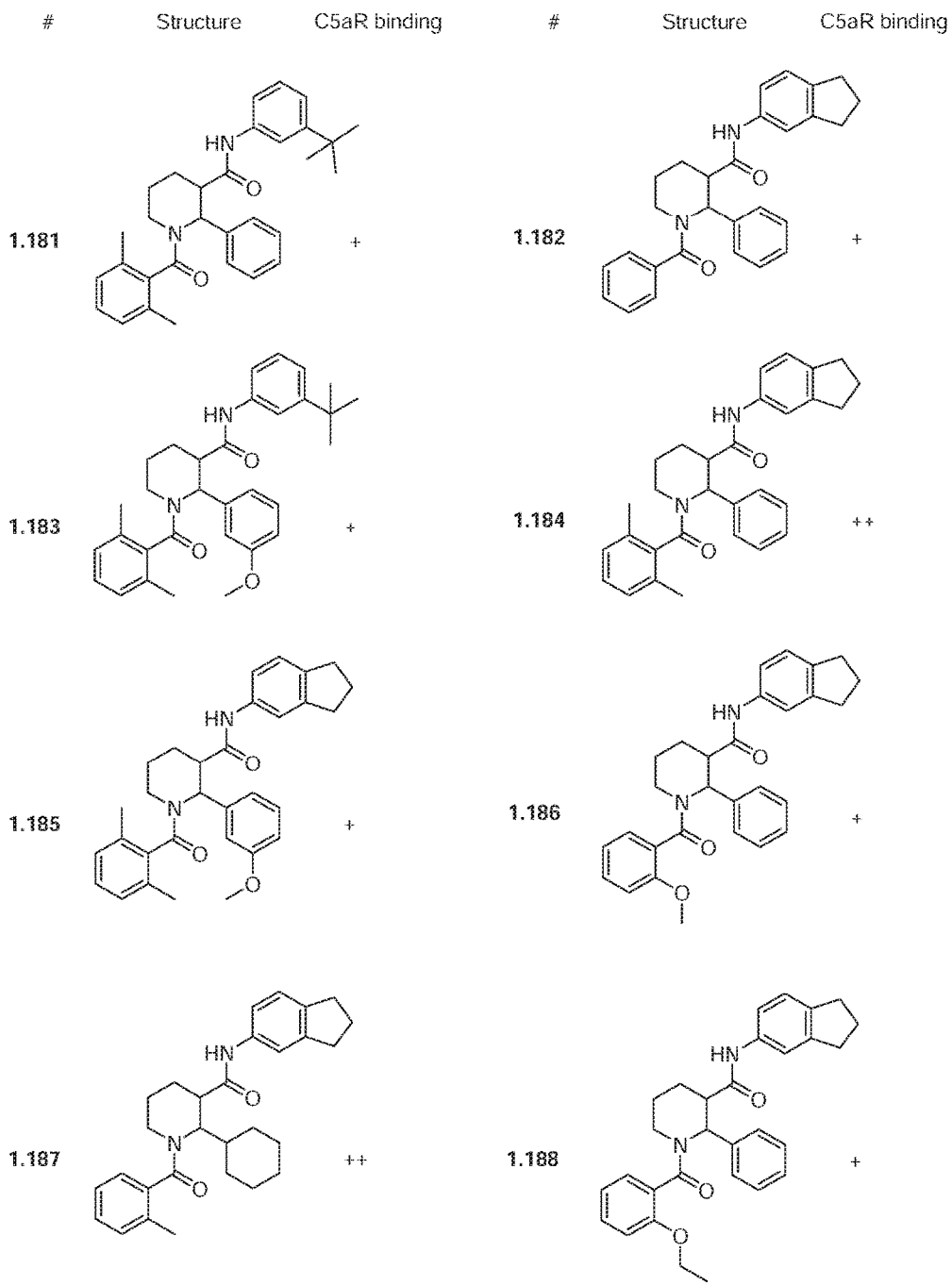
Figure 1Y:
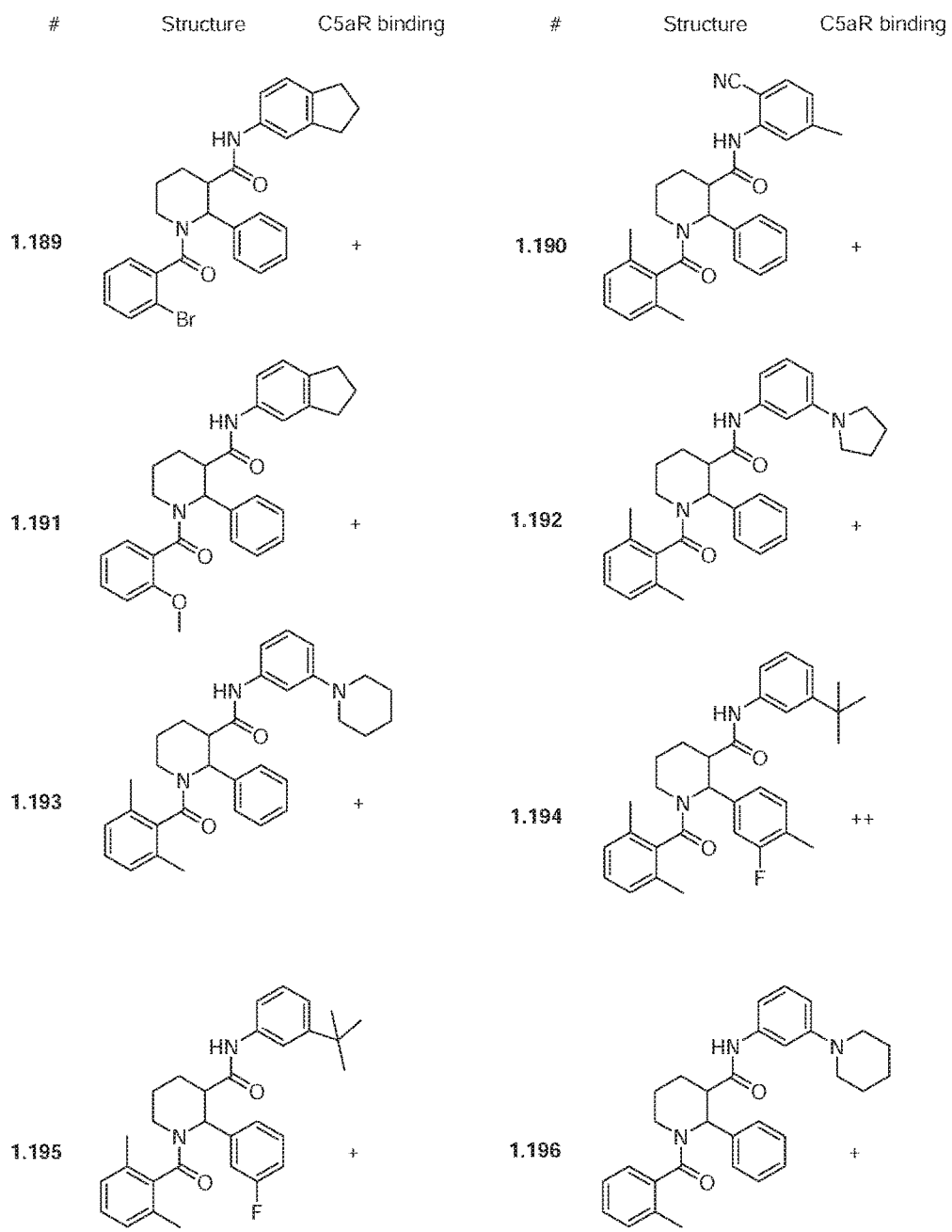
Figure 1G:
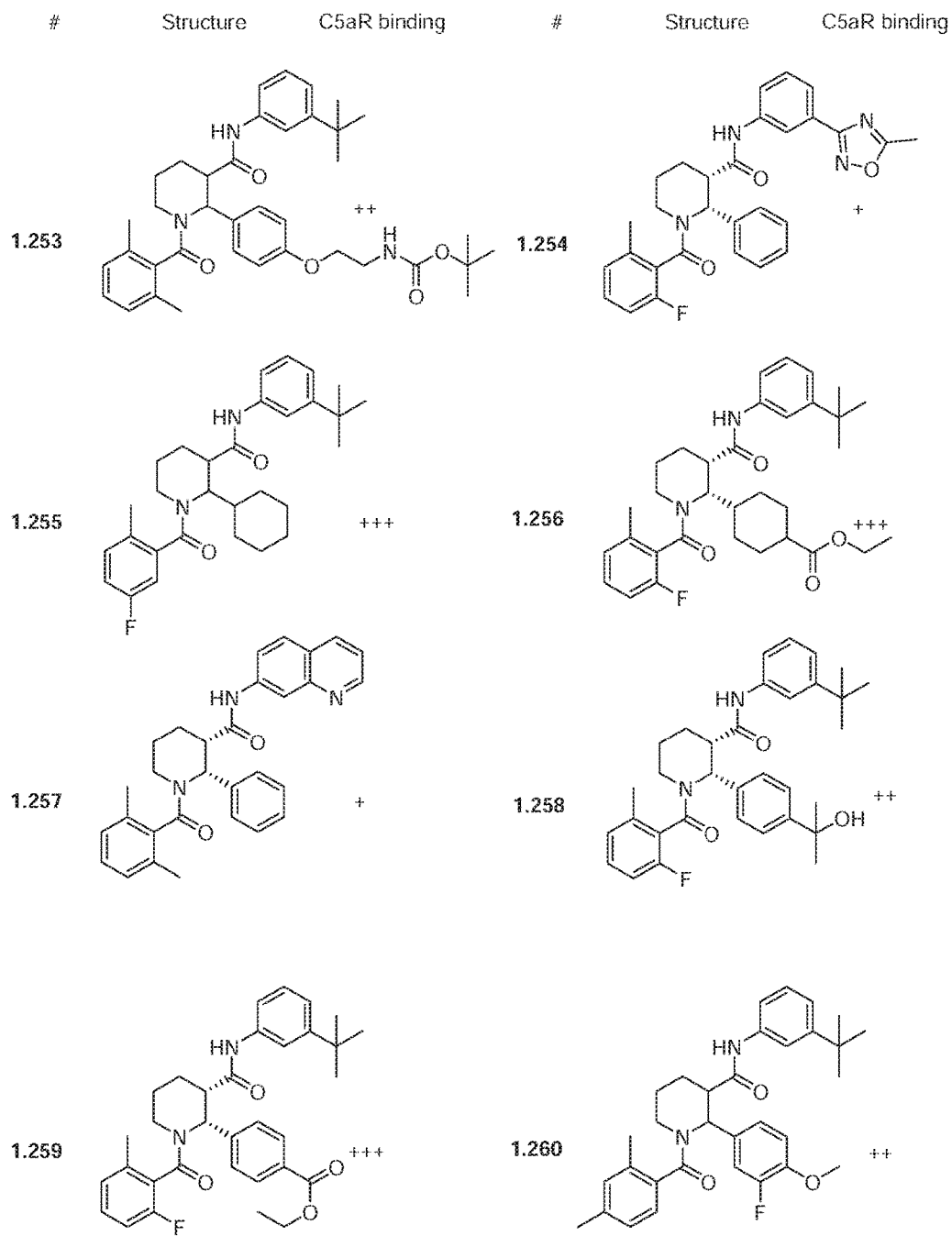
Figure 1M:
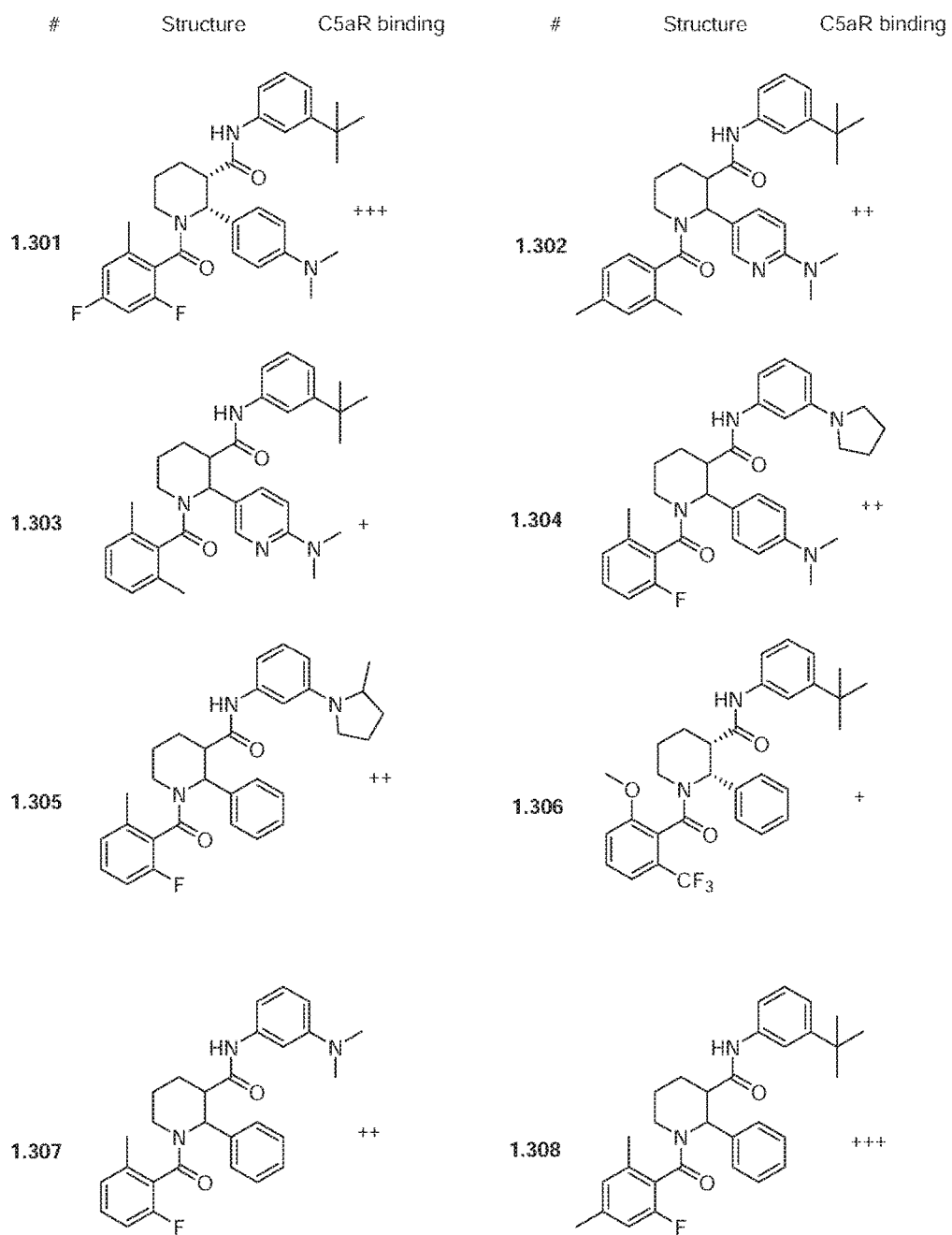
Figure 100:
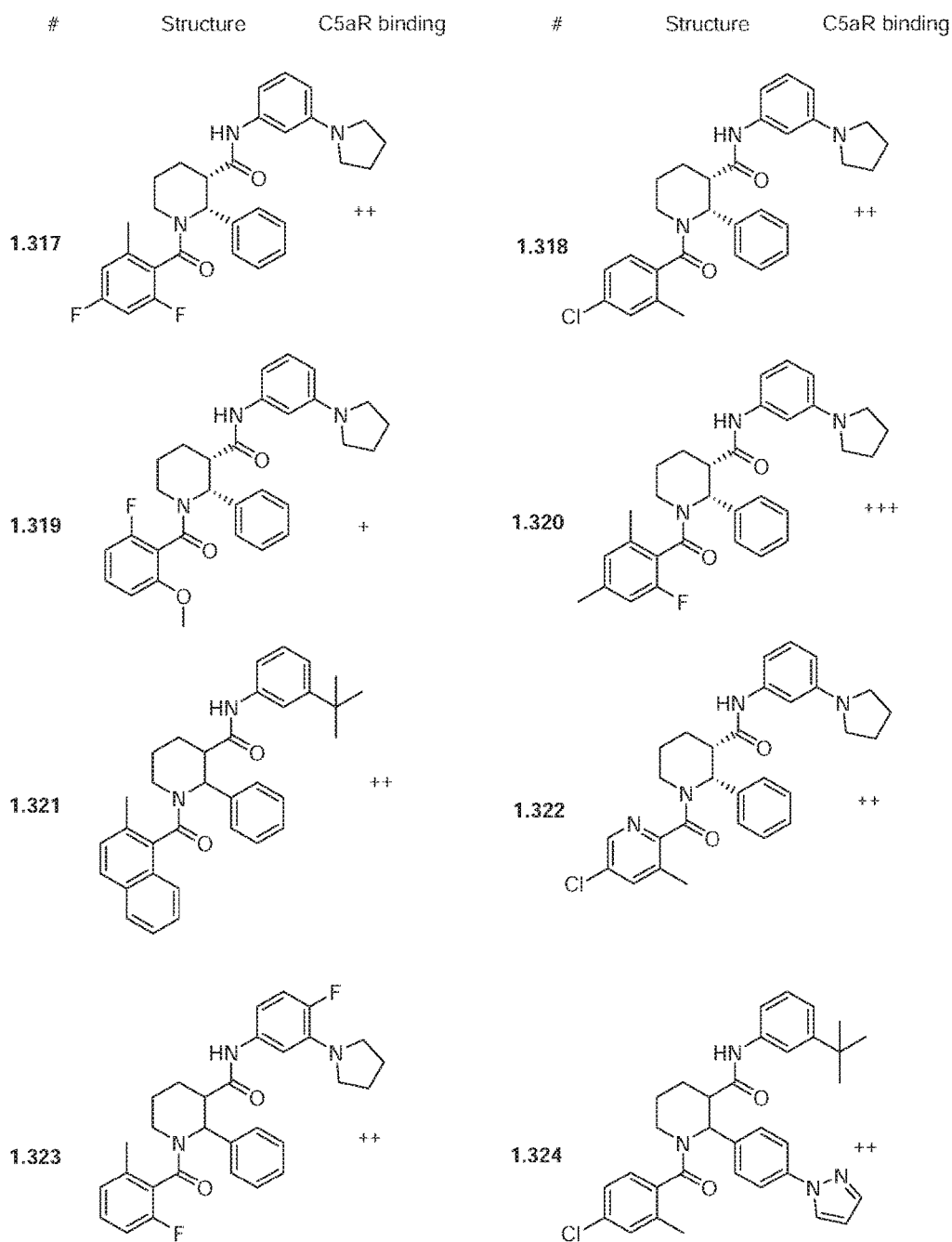
Figure 1P:
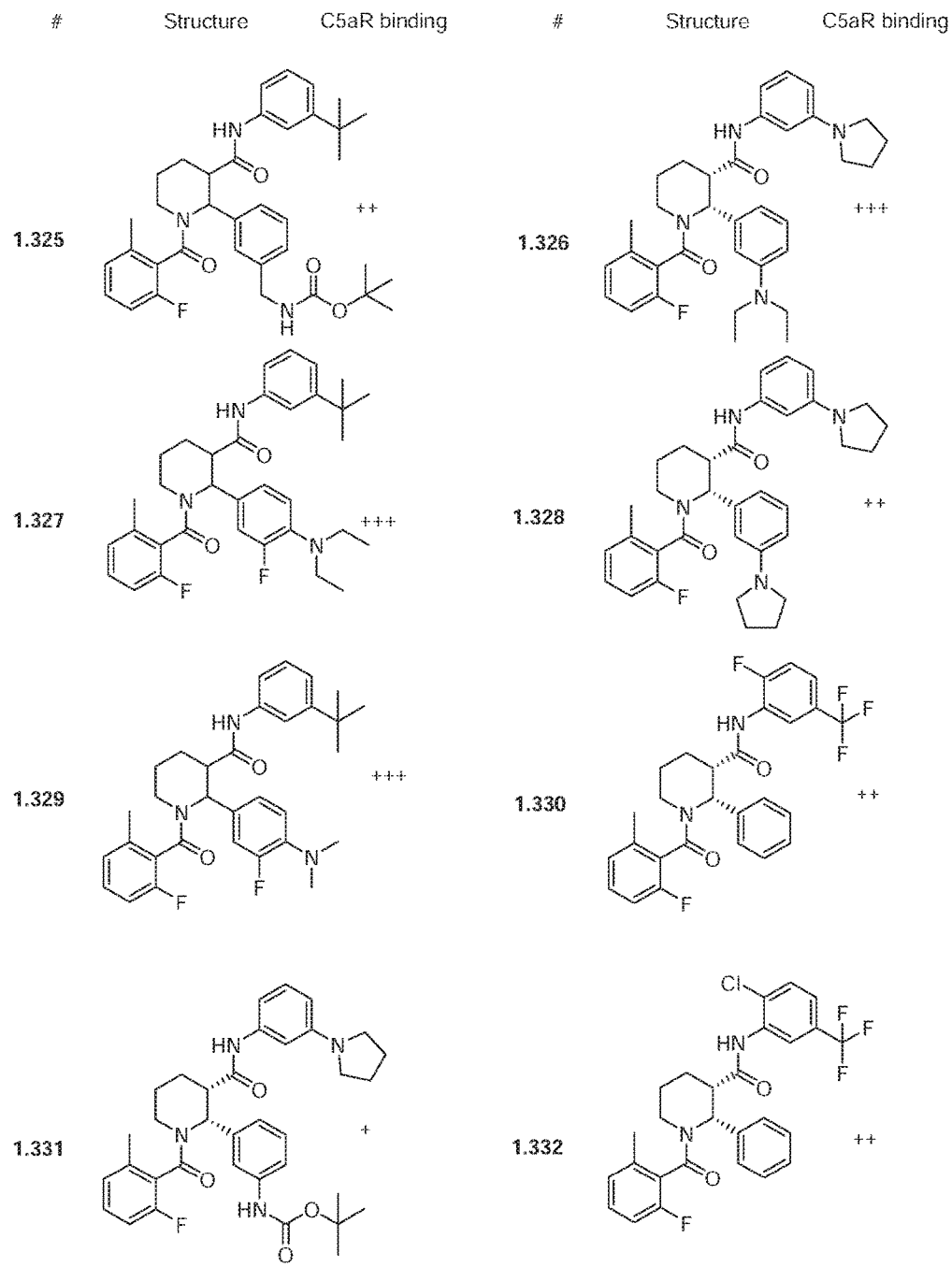
Figure 1T:
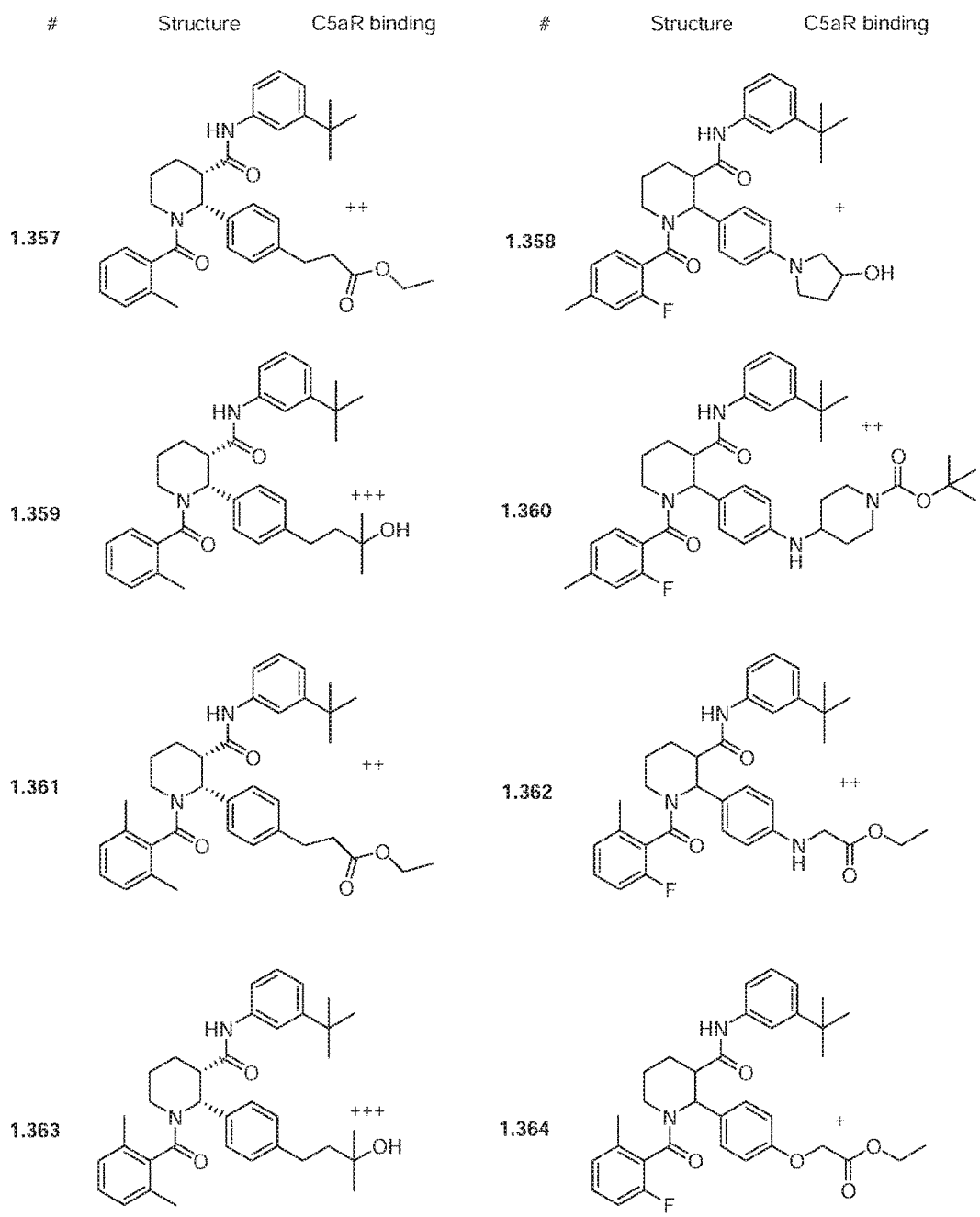
Figure 1U:
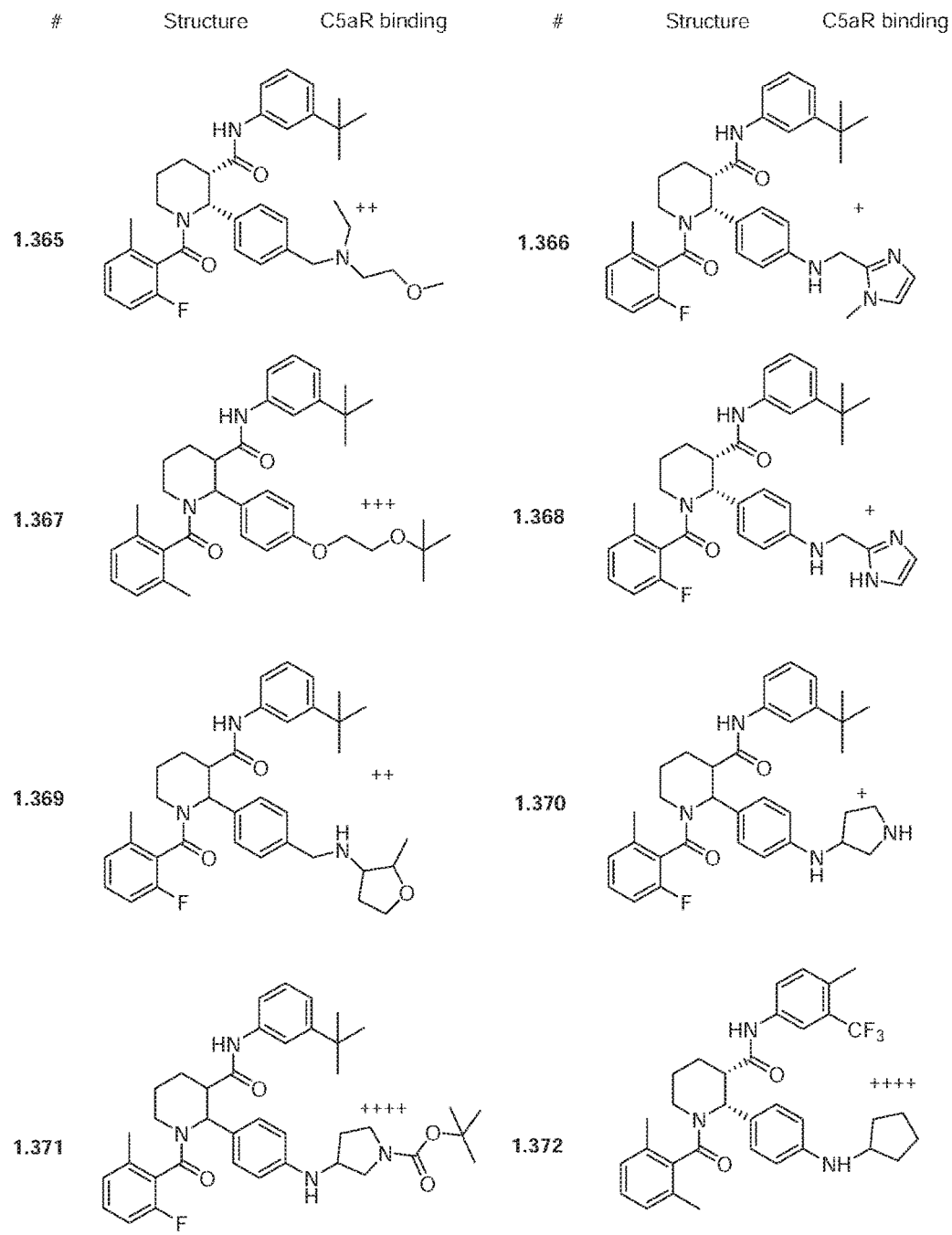
Figure 1W:
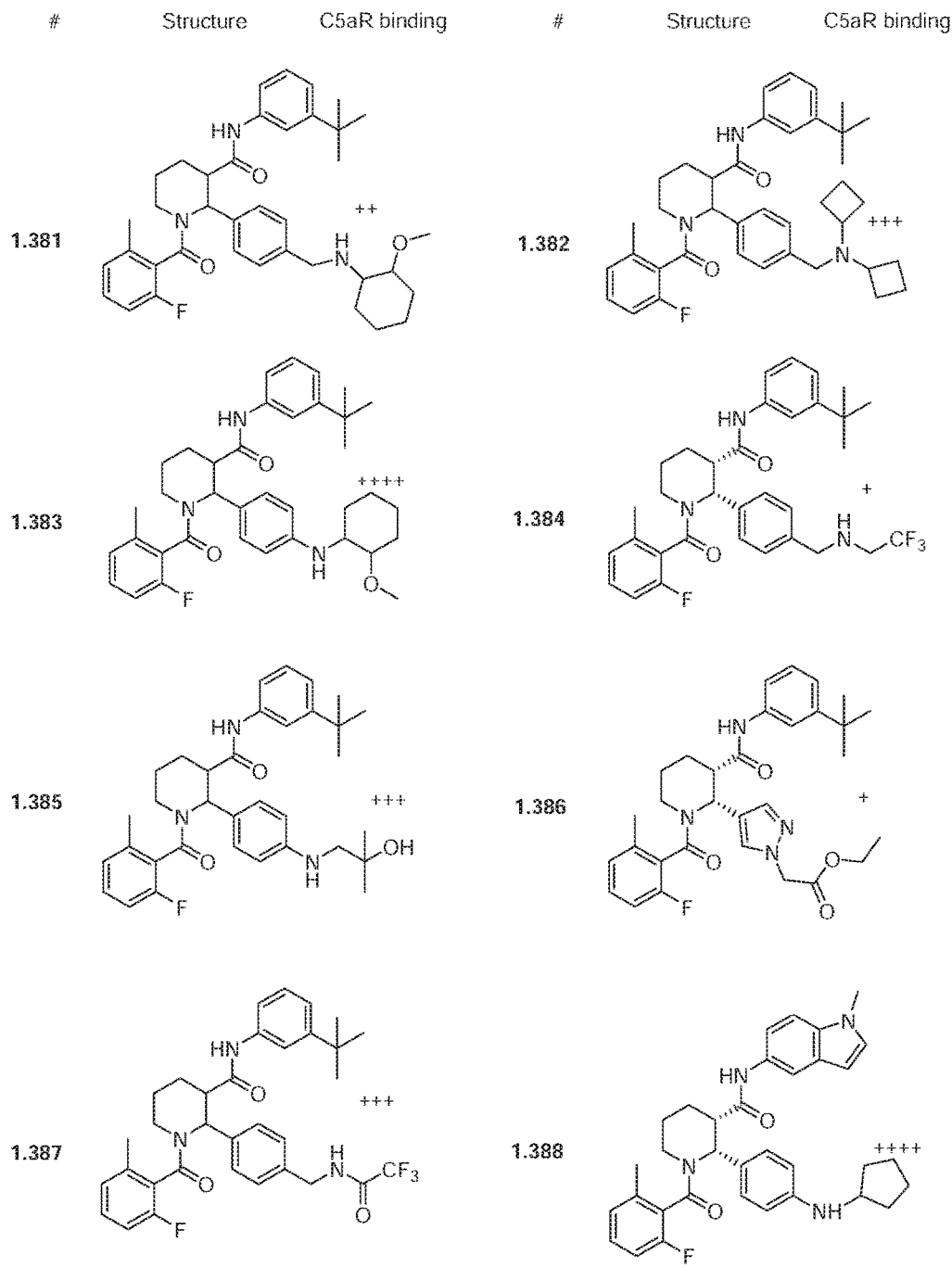
Figure 1Y:
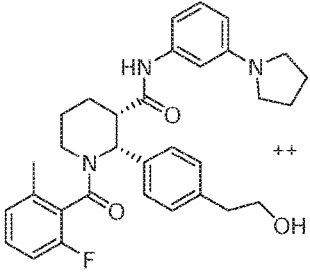

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkyl" in its broadest sense is also meant to include those unsaturated groups such as alkenyl and alkynyl groups. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)CH$_3$, —C(O)CH$_2$CH$_2$OR$^1$ and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system;

and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $C_1$-6 alkyl.

As used herein, the term "heteroatom" is meant to include oxygen (O), nitrogen (N), sulfur (S) and silicon (Si).

The term "ionic liquid" refers to any liquid that contains mostly ions. Preferably, in the present invention. "ionic liquid" refers to the salts whose melting point is relatively low (e.g., below 250° C.). Examples of ionic liquids include but are not limited to 1-butyl-3-methylimidazolium tetrafluoroborate, 1-hexyl-3-methylimidazolium tetrafluoroborate, 1-octyl-3-methylimidazolium tetrafluoroborate, 1-nonyl-3-methylimidazolium tetrafluoroborate, 1-decyl-3-methylimidazolium tetrafluoroborate, 1-hexyl-3-methylimidazolium hexafluorophosphate and 1-hexyl-3-methylimidazolium bromide, and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention. For example, the compounds may be prepared such that any number of hydrogen atoms are replaced with a deuterium ($^2H$) isotope.

II. Compounds

In one aspect, the present invention provides compounds having the formula I:

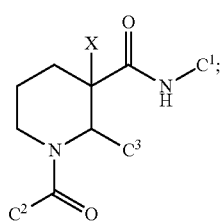

(I)

and pharmaceutically acceptable salts, hydrates and rotomers thereof; wherein $C^1$ is selected from the group consisting of aryl and heteroaryl, wherein the heteroaryl group has from 1-3 heteroatoms as ring members selected from N, O and S: and wherein said aryl and heteroaryl groups are optionally substituted with from 1 to 3 $R^1$ substituents;

$C^2$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^2$ substituents;

$C^3$ is selected from the group consisting of $C_{1-8}$ alkyl or heteroalkyl, $C_{3-8}$cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-$C_{1-4}$ alkyl, wherein the heterocycloalkyl group or portion has from 1-3 heteroatoms selected from N, O and S, and wherein the heteroaryl group has from 1-3 heteroatoms as ring members selected from N, O and S, and each $C^1$ is optionally substituted with from 1-3 $R^3$ substituents;

each $R^1$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)NR'$R^b$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each $R^c$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;

each $R^2$ is independently selected from the group consisting of halogen, —CN, —$NO_2$, —$R^e$, —$CO_2R^d$, —$CONR^dR^e$, —C(O)$R^d$, —OC(O)$NR^dR^e$, —$NR^eC(O)R^d$, —$NR^eC(O)_2R^f$, —$NR^dC(O)NR'R^e$, —$NR^dC(O)NR^dR^e$, —$NR^dR^e$, —$OR^d$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S. and is optionally substituted with one or two oxo; each $R^f$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;

each $R^3$ is independently selected from the group consisting of halogen, —CN, —$R^i$, —$CO_2R^g$, —$CONR^gR^h$, —C(O)$R^g$, —C(O)$R^i$, —OC(O)$NR^gR^h$, —$NR^hC(O)R^g$, —$NR^hCO_2R^i$, —$NR^5C(O)NR^gR^h$, —$NR^gR^h$, —$OR^g$, —$OR^j$, —$S(O)_2NR^gR^h$, —$X^4$—$R^j$, —NH—$X^4$—$R^j$, —O—$X^4$—$R^j$, —$X$—$NR^gR^h$, —$X^4$—$NHR^j$, —$X^4$—$CONR^gR^h$, —$X^4$—$NR^hC(O)R^g$, —$X^4$—$CO_2R^g$, —O—$X^4$—$CO_2R^g$, —NH—$X^4$—$CO_2R^g$, —$X^4$—$NR^hCO_2R^i$, —O—$X^4$—$NR^hCO_2R^i$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl or heteroalkyl, $C_{3-8}$cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each $R^i$ is independently selected from the group consisting of $C_{1-8}$ alkyl or heteroalkyl. $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, imidazolyl, pyrimidinyl, pyrrolinyl, piperidinyl, morpholinyl, tetrahydrofuranyl, tetrahydropyranyl, and S,S-dioxo-tetrahydrothiopyranyl, and wherein the aliphatic and cyclic portions of $R^g$, $R^h$, $R^i$ and $R^j$ are optionally further substituted with from one to three halogen, methyl, $CF_3$, hydroxy, $C_{1-4}$ alkoxy, $C_{1-4}$ alkoxy-$C_{1-4}$ alkyl, —C(O)O—$C_{1-8}$ alkyl, amino, alkylamino and dialkylamino groups, and optionally when two $R^3$ groups are on adjacent atoms, they are combined to form a five- or six-membered ring; and X is hydrogen or $CH_3$.

In formula I, the substituent $C^1$ is, in one embodiment, selected from the group consisting of phenyl, pyridyl, indolyl and thiazolyl, each of which is optionally substituted with from 1 to 3 $R^1$ substituents. Preferably, each $R^1$ is independently selected from the group consisting of halogen, —CN, —$R^c$, —$NR^aR^b$ and —$OR^a$, and wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a pyrrolidine ring; each R is independently selected from the group consisting of $C_{1-8}$ alkyl, $C_{1-8}$ haloalkyl and $C_{3-6}$ cycloalkyl, and wherein the aliphatic and cyclic portions of $R^a$, $R^b$ and $R^c$ are optionally further substituted with from one to three hydroxy, methyl, amino, alkylamino and dialkylamino groups; and optionally when two $R^1$ substituents are on adjacent atoms, are combined to form a fused five or six-membered carbocyclic ring. In selected embodiments of the invention, $C^1$ is selected from:

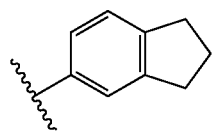 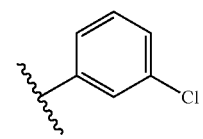

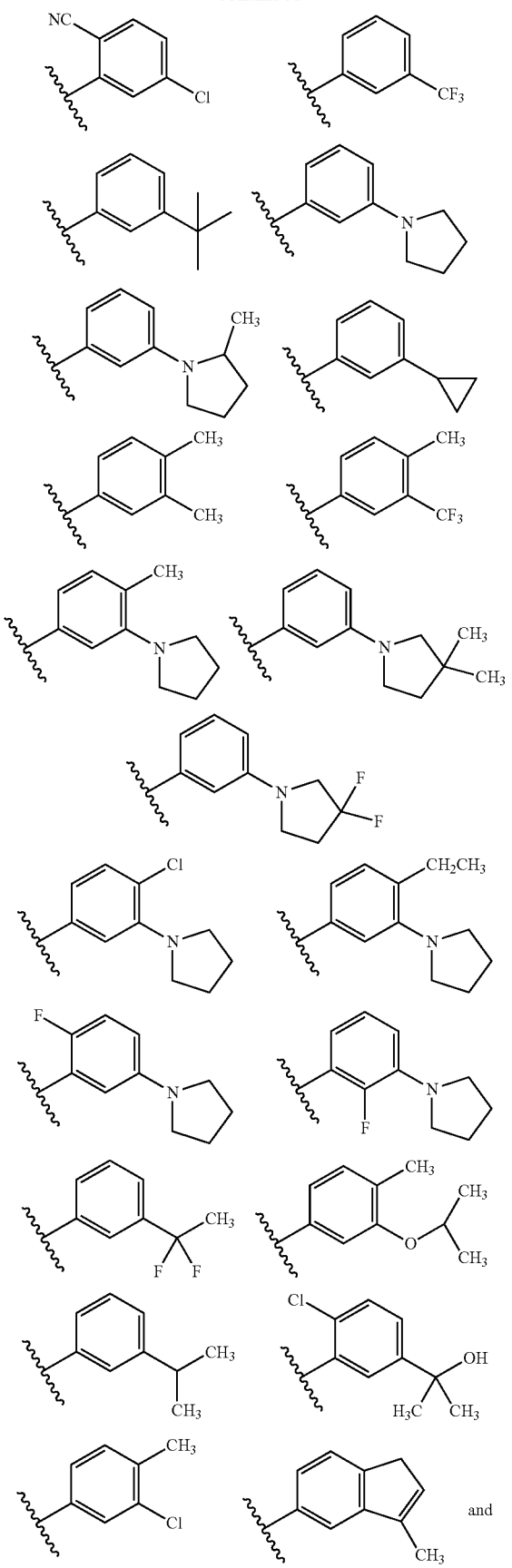
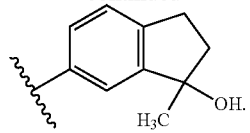

Returning to formula I, the substituents $C^2$ is, in one embodiment, selected from the group consisting of phenyl, naphthyl, pyridyl and indolyl, each of which is optionally substituted with from 1 to 3 $R^2$ substituents. Preferably, each $R^2$ is independently selected from the group consisting of halogen, —$R^f$ and —$OR^d$; wherein each $R^d$ is independently selected from hydrogen, $C_{1-8}$ alkyl, and $C_{1-8}$ haloalkyl; each $R^f$ is independently selected from the group consisting of $C_{1-8}$ alkyl, $C_{1-8}$ haloalkyl, $C_{3-6}$ cycloalkyl, heterocycloalkyl and heteroaryl, and wherein the aliphatic and cyclic portions of $R^d$ and $R^f$ are optionally further substituted with from one to three halogen, hydroxy, methyl, amino, alkylamino and dialkylamino groups. In selected embodiments of the invention, $C^2$ is selected from the group consisting of:

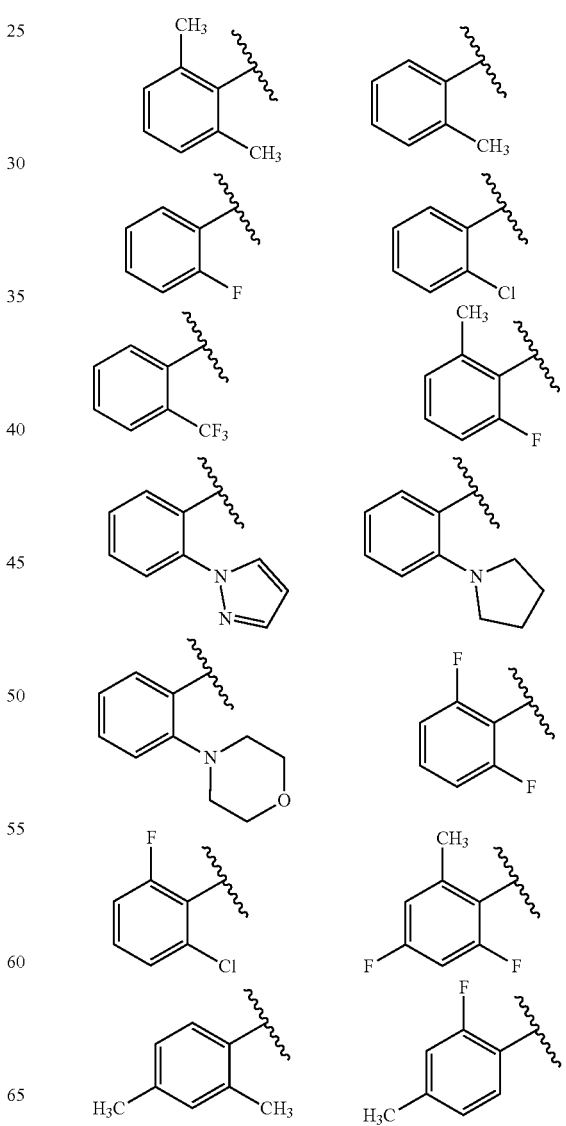

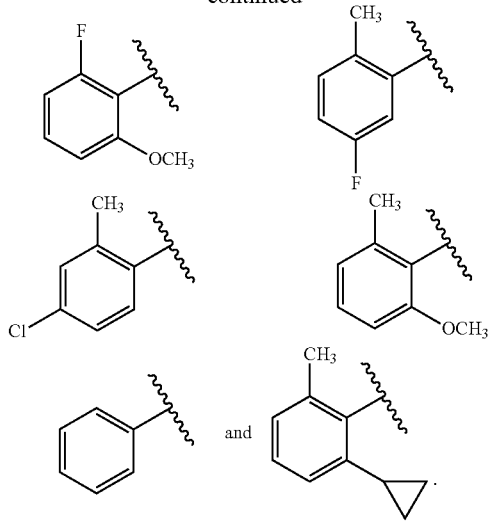

The substituent $C^3$ is, in some embodiments, selected from the group consisting of $C_{3-6}$ alkyl, $C_{3-6}$ cycloalkyl, $C_{3-6}$ cycloalkyl$C_{1-2}$alkyl, phenyl, pyridinyl, pyrazolyl, piperidinyl, pyrrolidinyl, piperidinylmethyl and pyrrolidinylmethyl, each of which is optionally substituted with from 1 to 3 $R^3$ substituents. Preferably, each $R^3$ is independently selected from the group consisting of halogen, —$R^i$, —$CO_2R^g$, —$CONR^gR^h$, —$NR^hC(O)R^g$, —$NR^hC(O)_2R^i$, —$NR^gR^h$, —$OR^g$, —$X^4$—$R^j$, —$X^4$—$NR^gR^h$, —$X^4$—$CONR^gR^h$, —$X^4$—$NR^hC(O)RR$, —$NHR^j$ and —$NHCH_2R^j$, wherein $X^4$ is a $C_{1-3}$ alkylene; each $R^g$ and $R^h$ is independently selected from hydrogen, $C_{1-8}$ alkyl, $C_{3-6}$ cycloalkyl and $C_{1-8}$ haloalkyl, or when attached to the same nitrogen atom can be combined with the nitrogen atom to form a five or six-membered ring having from 0 to 1 additional heteroatoms as ring members selected from N, O or S and is optionally substituted with one or two oxo; each $R^i$ is independently selected from the group consisting of $C_{1-8}$ alkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, pyrrolinyl, piperidinyl, morpholinyl, tetrahydrofuranyl, and tetrahydropyranyl, and wherein the aliphatic and cyclic portions of $R^g$, $R^h$, $R^i$ and $R^j$ are optionally further substituted with from one to three halogen, methyl, $CF_3$, hydroxy, amino, alkylamino and dialkylamino groups. In selected embodiments of the invention, $C^3$ is selected from the group consisting of:

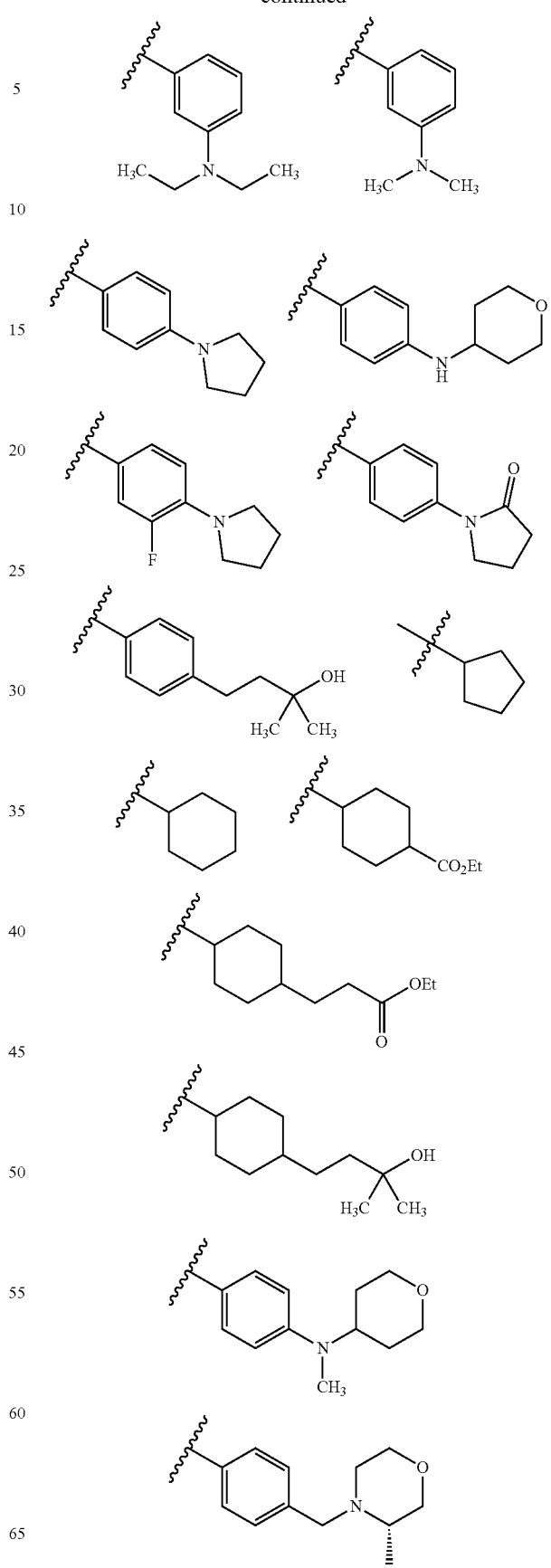

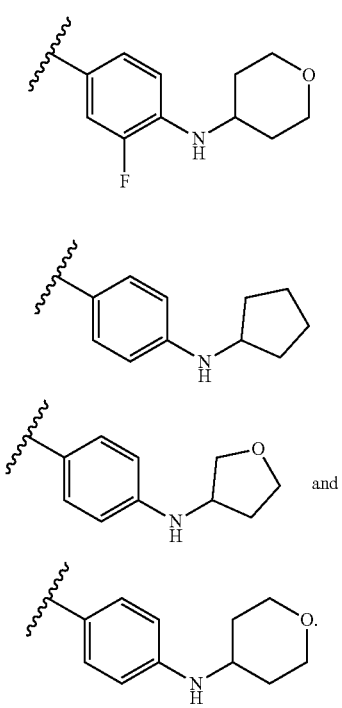
In other embodiments, $C^3$ is selected from the group consisting of:
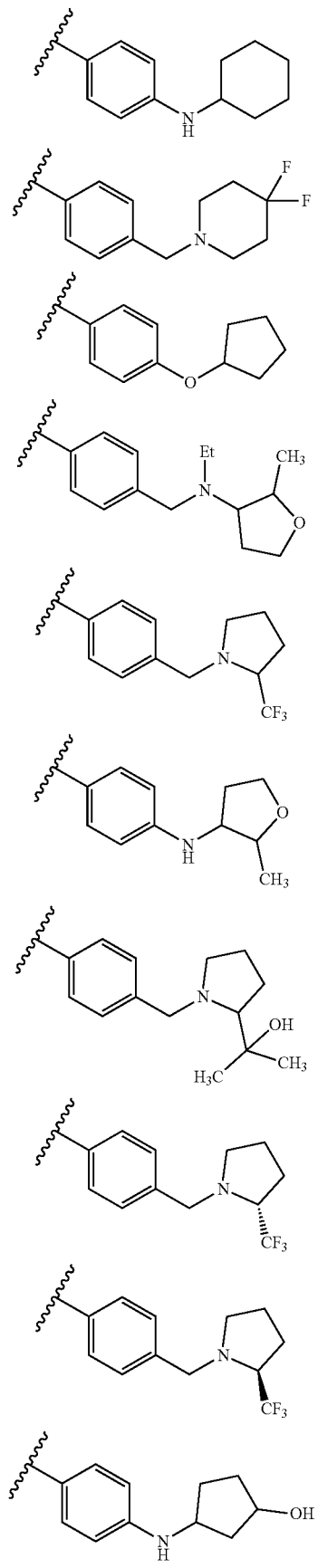

-continued

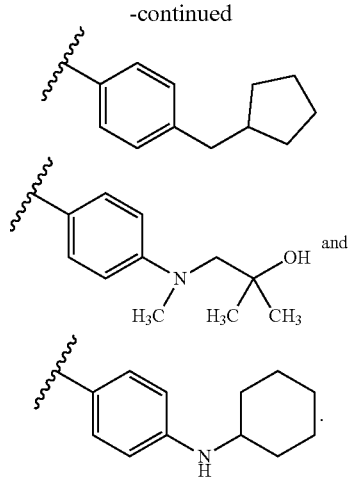

Returning to formula I, X is preferably H.

Subformulae of Formula I:

In one embodiment of the invention, compounds of formula I have subformula Ia:

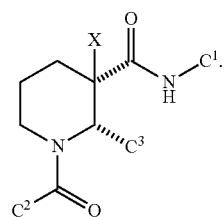
(Ia)

In a second embodiment of the invention, compounds of formula I have subformula

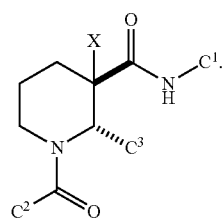
(Ib)

In a third embodiment of the invention, compounds of formula I have subformula Ic.

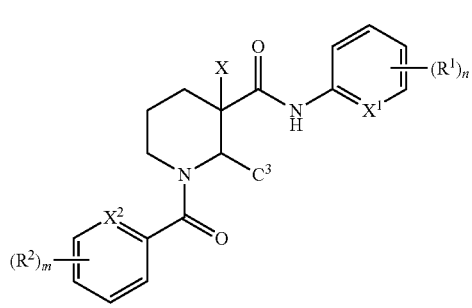
(Ic)

wherein $X^1$ is selected from the group consisting of N, CH and $CR^1$; the subscript n is an integer of from 0 to 2; $X^2$ is selected from the group consisting of N, CH and $CR^2$; and the subscript m is an integer of from 0 to 2.

In a fourth embodiment of the invention, compounds of formula I have subformula Id:

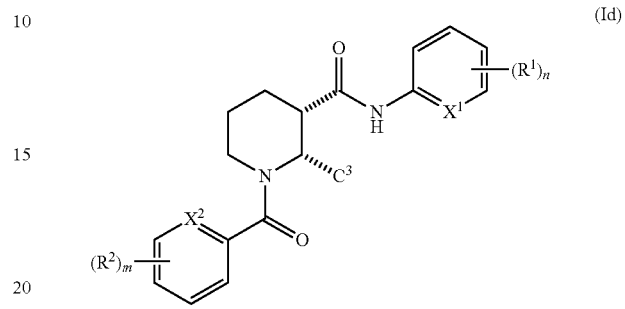
(Id)

wherein $X^1$ is selected from the group consisting of N, CH and $CR^1$; the subscript n is an integer of from 0 to 2; $X^2$ is selected from the group consisting of N, CH and $CR^2$; and the subscript m is an integer of from 0 to 2.

In a fifth embodiment of the invention, compounds of formula I have subformula Ie:

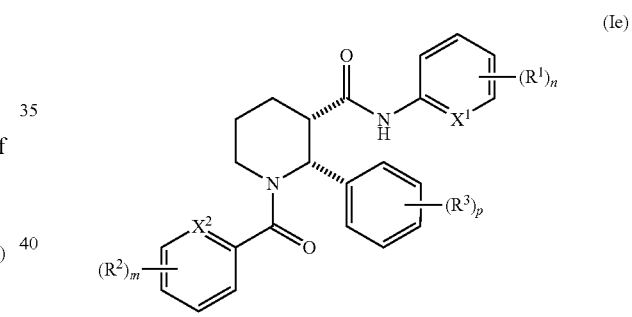
(Ie)

wherein the subscript p is an integer of from 0 to 3; $X^1$ is selected from the group consisting of N, CH and $CR^1$; the subscript n is an integer of from 0 to 2; $X^2$ is selected from the group consisting of N, CH and $CR^2$; and the subscript m is an integer of from 0 to 2.

In other selected embodiments, the compounds of the invention are represented by:

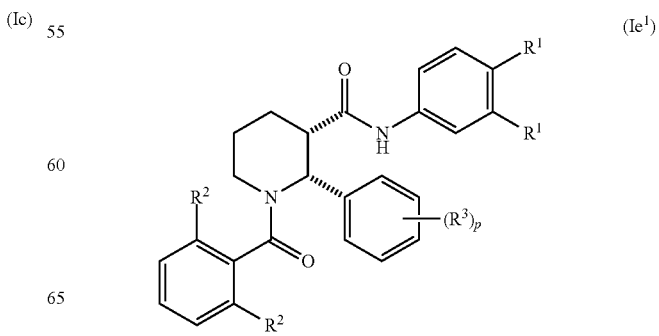
(Ie¹)

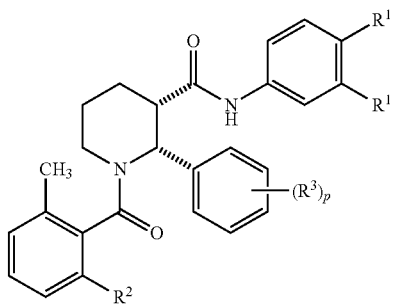
(Ie²)

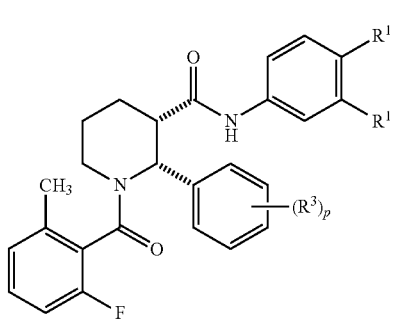
(Ie³)

wherein the substituents R¹, R² and R³, and the subscript p all have the meanings provided with reference to formula I.

In still other selected embodiments, the compounds of the invention are represented by:

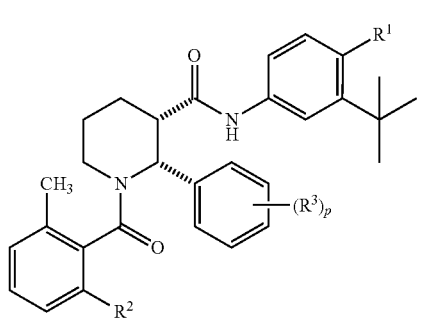
(Ie⁴)

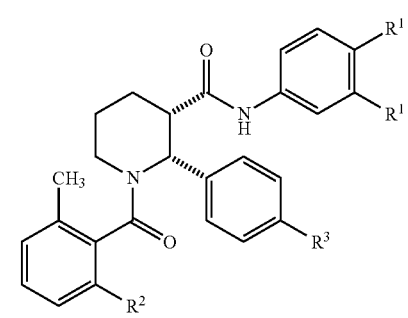
(Ie⁵)

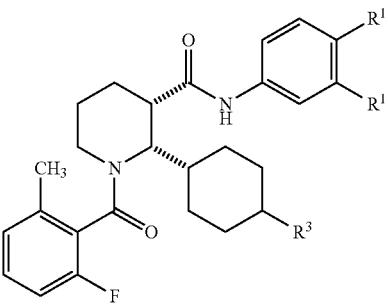
(If)

wherein the substituents R¹ and R³, and the subscript p all have the meanings provided with reference to formula I.

In a particularly preferred group of embodiments, the compounds of the invention are represented by formula (Ie⁵) wherein R³ is a member selected from the group consisting of —NR$^g$R$^h$, —NHR$^j$ and —NHCH$_2$R$^j$, and each R$^g$, R$^h$ and R$^j$ have the meanings provided with reference to formula I.

In another particularly preferred group of embodiments, the compounds of the invention are represented by formula (Ie⁵) wherein R³ is a member selected from the group consisting of —X⁴—NR$^g$R$^h$, —X⁴—R$^j$ and —X⁴—NR$^h$-COR$^g$, and each of X⁴, R$^g$, R$^h$ and R$^j$ have the meanings provided with reference to formula I.

Compounds of the invention having formula I can exist in different diastereomeric forms, e.g., the substituents C¹ and C² in subformulae Ia and Ic can be cis to each other or trans to each other. As used herein, the terms cis or trans are used in their conventional sense in the chemical arts, i.e., referring to the position of the substituents to one another relative to a reference plane, e.g., a double bond, or a ring system such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more σ bonds. Rotamers are conformers that differ by rotation about only a single a bond.

Preparation of Compounds

Those skilled in the art will recognize that there are a variety of methods available to synthesize molecules represented in the claims. In general, useful methods for synthesizing compounds represented in the claims consist of four parts, which may be done in any order: Formation of the piperidine ring, installation of two amide bonds, and installation and/or modification of functional groups on C¹, C², and C³.

Several methods for the preparation of claimed compounds are illustrated below (eq. 1-6).

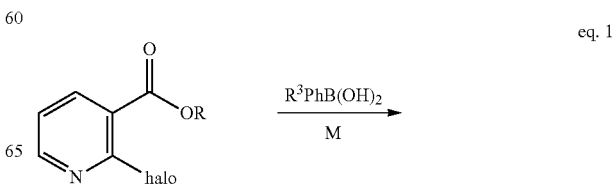
eq. 1

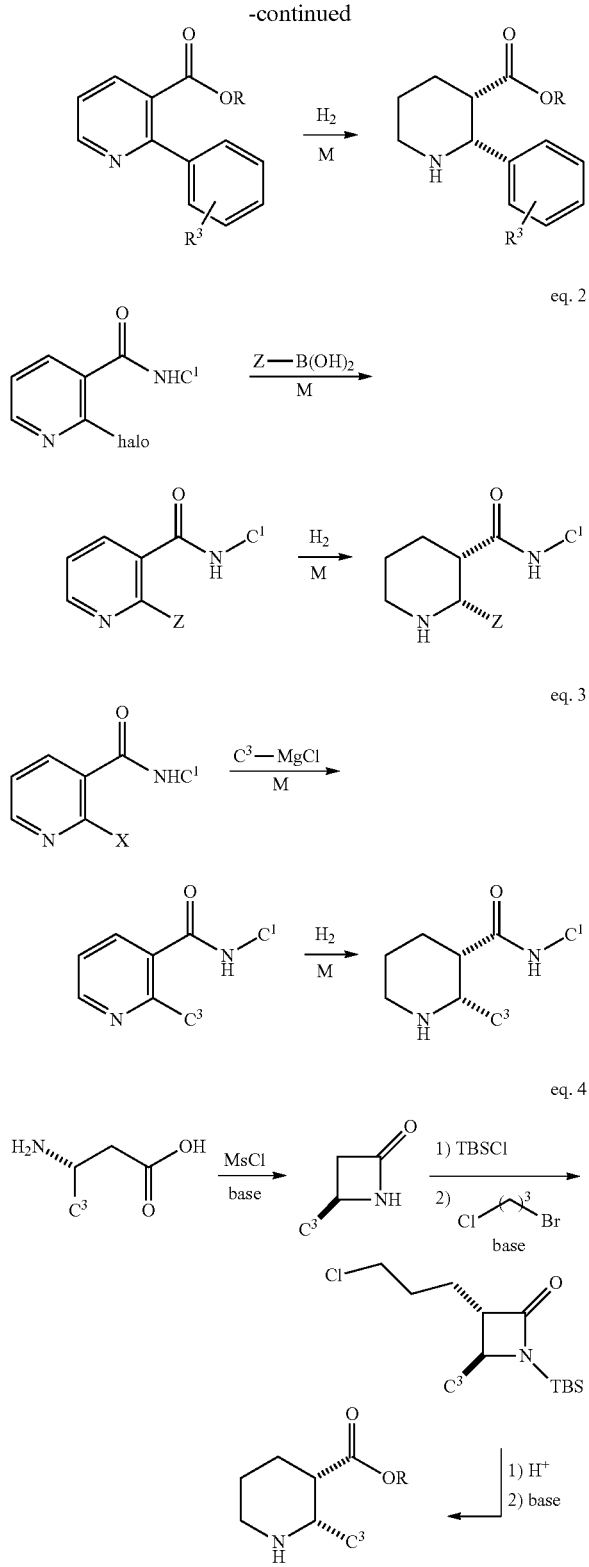

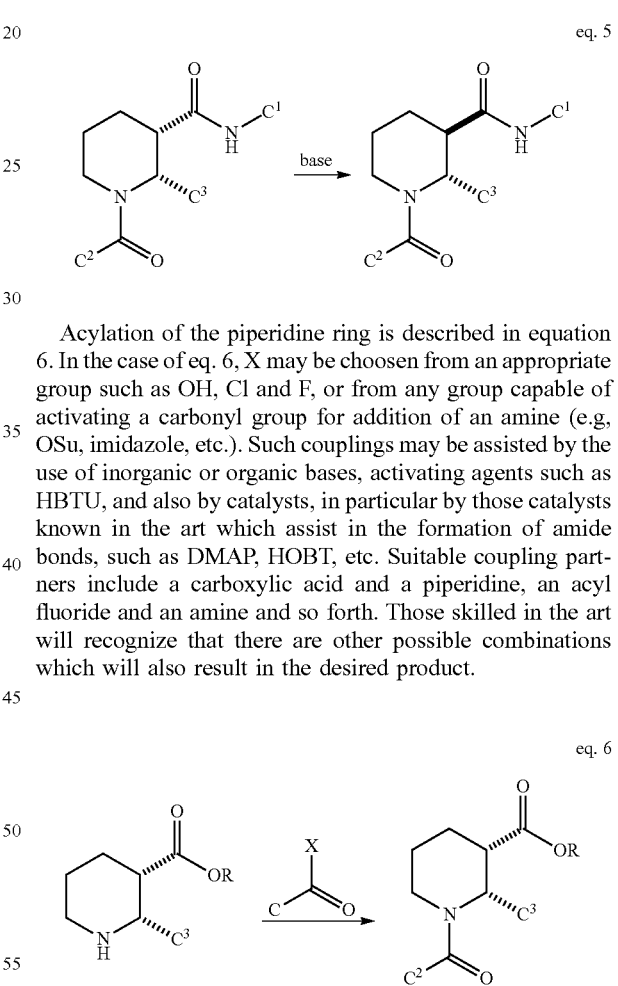

Equations 1-4 demonstrate some methods of forming the piperidine ring. Coupling at the 2-position of the pyridine ring can be accomplished via transition metal mediated couplings as shown in eq. 1-2, or metal catalyzed addition of an organometallic species such as the zincate or magnesium salt (eq. 3). Subsequent to coupling at the 2-position, transition metal mediated hydrogenation of the pyridine ring yields the piperidine ring system (eq. 1-3). Another method results in elaboration of a β-amino acid to a piperidine ring as described in eq. 4. Those skilled in the art will recognize that many synthetic methodologies can yield substituted piperidines, including C—C or C—N cyclization of acyclic precursors via alkylation or ring-closing metathesis. Relative stereochemistry may be set by a variety of methods, including facial selectivity during the hydrogenation step. Absolute stereochemistry may also be set via a variety of methods, via the use of chiral ligands or a chiral auxiliary, separation of chiral diastereoisomers, use of chiral starting materials, or classical resolution. Compounds with 2,3-trans stereochemistry may have the relative stereochemistry set during the piperidine formation, or may be derived via epimerization of a 2,3-cis piperidine as illustrated in eq. 5.

Acylation of the piperidine ring is described in equation 6. In the case of eq. 6, X may be choosen from an appropriate group such as OH, Cl and F, or from any group capable of activating a carbonyl group for addition of an amine (e.g, OSu, imidazole, etc.). Such couplings may be assisted by the use of inorganic or organic bases, activating agents such as HBTU, and also by catalysts, in particular by those catalysts known in the art which assist in the formation of amide bonds, such as DMAP, HOBT, etc. Suitable coupling partners include a carboxylic acid and a piperidine, an acyl fluoride and an amine and so forth. Those skilled in the art will recognize that there are other possible combinations which will also result in the desired product.

A variety of methods described above have been used to prepare compounds of the invention, some of which are described in the examples.

Figure 1:
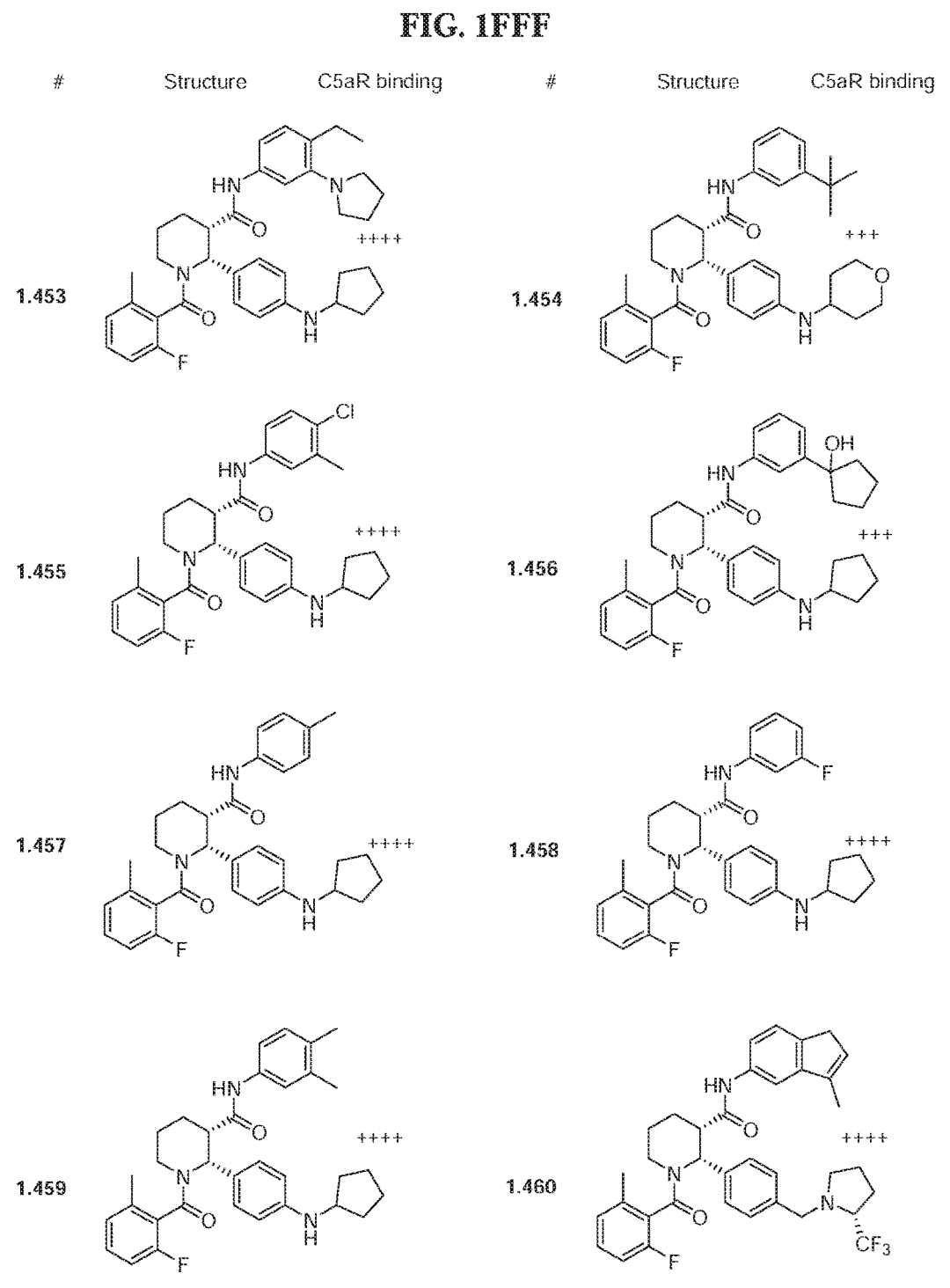

A family of specific compounds of particular interest having formula I consists of compounds, pharmaceutically acceptable salts, hydrates and rotomers thereof, as set forth in FIGS. 1A-1QQQ. For the compounds of FIGS. 1A-1QQQ, any bond not illustrating at attached atom or group is meant to be a methyl group. For example,

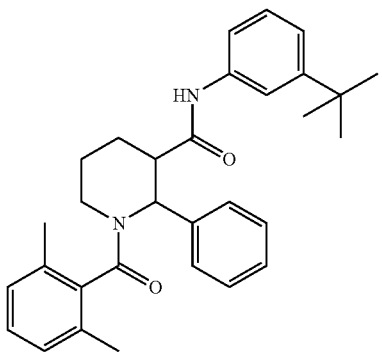 [SMILES: Cc1cccc(C)c1C(=O)N1CCCC(C(=O)Nc2cccc(C(C)(C)C)c2)C1c1ccccc1]

is meant to illustrate CH

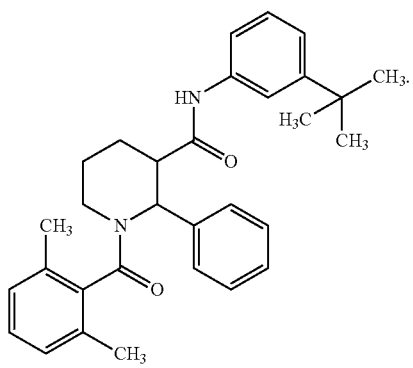 [SMILES: Cc1cccc(C)c1C(=O)N1CCCC(C(=O)Nc2cccc(C(C)(C)C)c2)C1c1ccccc1]

III. Pharmaceutical Compositions

In addition to the compounds provided above, compositions for modulating C5a activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

IV. Methods of Treating Diseases and Disorders Modulated by C5a

The compounds of the invention may be used as agonists, (preferably) antagonists, partial agonists, inverse agonists, of C5a receptors in a variety of contexts, both in vitro and in vivo. In one embodiment, the compounds of the invention are C5aR antagonist that can be used to inhibit the binding of C5a receptor ligand (e.g, C5a) to C5a receptor in vitro or in vivo. In general, such methods comprise the step of contacting a C5a receptor with a sufficient amount of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), in a cultured or isolated cell, or in a tissue or organ.

Preferably, the amount of C5a receptor modulator contacted with the receptor should be sufficient to inhibit C5a binding to C5a receptor in vitro as measured, for example, using a radioligand binding assay, calcium mobilization assay, or chemotaxis assay as described herein.

In one embodiment of the invention, the C5a modulators of the invention are used to modulate, preferably inhibit, the signal-transducing activity of a C5a receptor, for example, by contacting one or more compound(s) of the invention with a C5a receptor (either in vitro or in vivo) under conditions suitable for binding of the modulator(s) to the receptor. The receptor may be present in solution or suspension, in a cultured or isolated cell preparation or within a patient. Any modulation of the signal transducing activity may be assessed by detecting an effect on calcium ion calcium mobilization or by detecting an effect on C5a receptor-mediated cellular chemotaxis. In general, an effective amount of C5a modulator(s) is an amount sufficient to modulate C5a receptor signal transducing activity in vitro within a calcium mobilization assay or C5a receptor-mediated cellular chemotaxis within a migration assay.

When compounds of the invention are used to inhibit C5a receptor-mediated cellular chemotaxis, preferably leukocyte (e.g., neutrophil) chemotaxis, in an in vitro chemotaxis assay, such methods comprise contacting white blood cells (particularly primate white blood cells, especially human white blood cells) with one or more compounds of the invention. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound of the invention has been added.

In another embodiment, the compounds of the present invention are useful for facilitating organ transplants. In this embodiment, the compounds can be placed in a solution, with the organ prior to transplant.

In another embodiment, the compounds of the present invention further can be used for treating patients suffering from conditions that are responsive to C5a receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to C5a receptor modulation" if modulation of C5a receptor activity results in the reduction of inappropriate activity of a C5a receptor. As used herein, the term "patients" include primates (especially humans), domesticated companion animals (such as dogs, cats, horses, and the like) and livestock (such as cattle, pigs, sheep, and the like), with dosages as described herein.

Conditions that can be Treated by C5a Modulation:

Autoimmune Disorders— e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory Disorders and Related Conditions— e.g., Neutropenia sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant invention may also be useful in the treatment of age-related macular degeneration (Hageman et al, P.N.A.S. 102: 7227-7232, 2005).

Cardiovascular and Cerebrovascular Disorders— e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the invention may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—

Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present invention can be used to treat leukoclastic vasculitis, Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV Infection and AIDS—

C5a receptor modulators provided herein may be used to inhibit HIV infection, delay AIDS progression or decrease the severity of symptoms or HIV infection and AIDS.

Neurodegenerative Disorders and Related Diseases—

Within further aspects, C5a antagonists provided herein may be used to treat Alzheimer's disease, multiple sclerosis, and cognitive function decline associated with cardiopulmonary bypass surgery and related procedures.

Cancers—

The C5a antagonists provided herein are also useful for the treatment of cancers and precancerous conditions in a subject. Specific cancers that can be treated include, but are not limited to, sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

In another embodiment, the compounds of the present invention are useful in the treatment of cisplatin induced nephrotoxicity. In this embodiment, compound treatment can alleviate the nephrotoxicity induced by cisplatin chemotherapy of malignancies (Hao Pan et al, *Am J Physiol Renal Physiol*, 296, F496-504, 2009).

In one embodiment of the invention, the compounds of the invention can be used for the treatment of diseases selected from the group consisting of sepsis (and associated disorders), COPD, rheumatoid arthritis, lupus nephritis and multiple sclerosis.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally or topically. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In another aspect of the invention, the compounds of the invention can be used in a variety of non-pharmaceutical in vitro and in vivo application. For example, the compounds of the invention may be labeled and used as probes for the detection and localization of C5a receptor (cell preparations or tissue sections samples). The compounds of the invention may also be used as positive controls in assays for C5a receptor activity, i.e., as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

The compounds provided herein may also be used within a variety of well known cell separation methods. For example, modulators may be linked to the interior surface of a tissue culture plate or other support, for use as affinity ligands for immobilizing and thereby isolating. C5a receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

In FIGS. 1A-1QQQ, structures and activity are provided for representative compounds described herein. Activity is provided as follows for the binding assay as described herein: +, 500 nM≤$IC_{50}$<2000 nM; ++, 50 nM≤$IC_{50}$<500 nM; +++, 5 nM≤$IC_{50}$<50 nM; and ++++, $IC_{50}$<5 nM.

V. EXAMPLES

The following examples are offered to illustrate, but not to limit the claimed invention.

Reagents and solvents used below can be obtained from commercial sources such as Aldrich Chemical Co. (Milwaukee, Wis. USA). ¹H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:
EtOH: Ethanol
EtONa Sodium ethoxide
THF: Tetrahydrofuran
TLC: Thin layer chromatography
MeOH: Methanol Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of cis-1-(2-fluoro-6-methylbenzoyl)-2-phenylpiperidine-3-carboxylic acid (3-trifluoromethylphenyl)amide

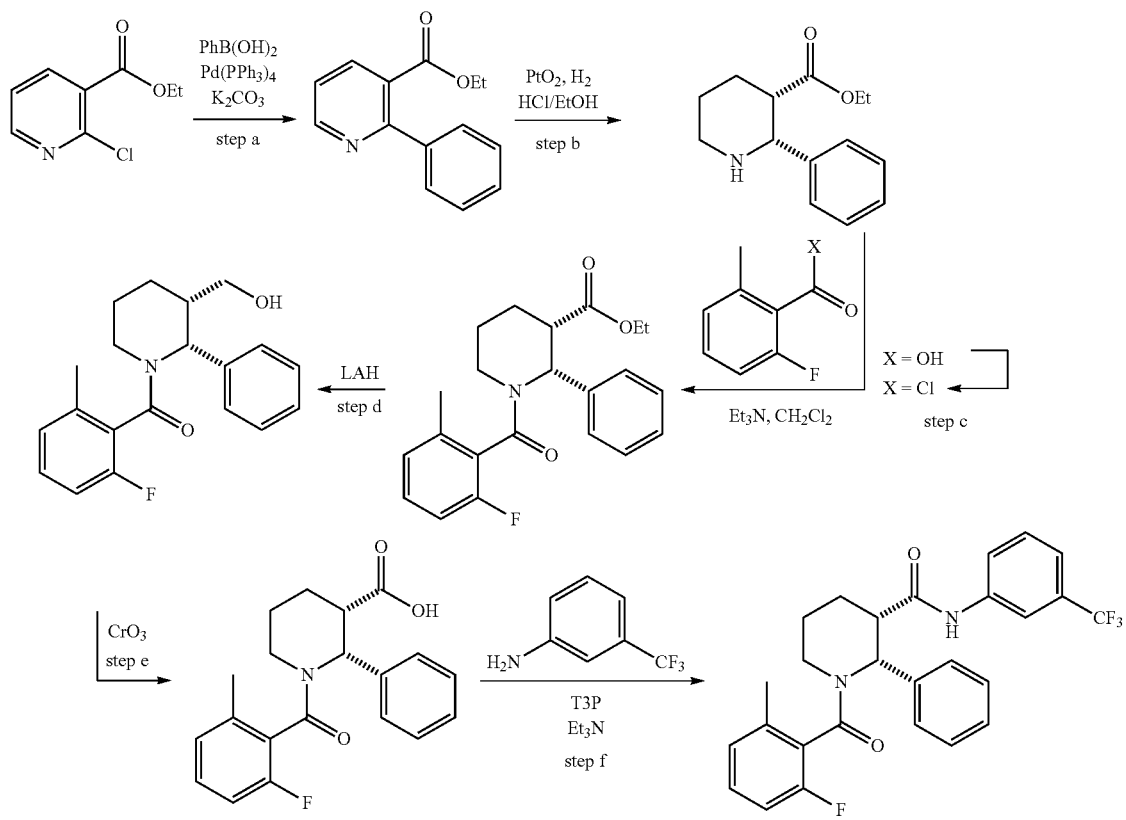

a) Pd(PPh$_3$)$_4$ (3.0 g, 2.6 mmol) was added to a solution of 2-chloro-3-carboxyethylpyridine (25 g, 134.7 mmol), phenylboronic acid (21.04 g, 172.6 mmol) and K$_2$CO$_3$ (55.1 g, 399 mmol) in 1,4-dioxane (200 mL) and water (200 mL). The reaction mixture was heated at 100° C. for 2 h. The solution was then cooled to room temperature and the dioxane was removed under reduced pressure. The resulting aqueous layer was extracted with ethyl acetate, and the combined organic layers were dried (Na$_2$SO$_4$), filtered through celite, and concentrated under reduced pressure. The residue was purified by flash chromatography (SiO$_2$, 10-100% EtOAc/hexanes) to get the 2-phenylpyridine derivative in 91% yield (27.98 g). LC-MS R$_t$ (retention time): 2.45 min, MS: (ES) m/z 228 (M+H$^+$).

b) PtO$_2$ (800 mg, 3.52 mmol) was added to a solution of 2-phenyl-nicotinic acid ethyl ester (20 g, 88 mmol, prepared in step a above) in EtOH (60 mL) and concentrated HCl (15 mL). The reaction mixture was hydrogenated using a Parr shaker at 40-45 psi, for 1 h. The reaction mixture was then filtered through celite, washed with EtOH, and the filtrate was concentrated under reduced pressure. The residue was diluted with CH$_2$Cl$_2$ and washed with saturated NaHCO$_3$. Purification by flash chromatography (SiO$_2$, 0-20% MeOH/CH$_2$Cl$_2$) gave the desired product in 85% yield (17.4 g). LC-MS R$_t$(retention time): 1.73 min, MS: (ES) m/z 234 (M+H$^+$).

c) Oxalyl chloride (3.2 mL, 30.75 mmol) was added to the solution of 2-fluoro-6-methylbenzoic acid (3.79 g, 24.6 mmol) in CH$_2$Cl$_2$ (20 mL) in a reaction flask at room temperature, followed by addition of a catalytic amount of DMF. The reaction was kept stirring for 2 h at room temperature. Solvent and excess oxalyl chloride were removed in vacuo and the residue was dried under high vacuum for 20 min. The resulting acid chloride was dissolved in dry CH$_2$Cl$_2$ (20 mL) and cooled to 0° C. followed by the addition of the piperidine made in step b (5.56 g, 20.5 mmol) and Et$_3$N (8.6 mL, 61.5 mmol). The mixture was then allowed to warm to room temperature and stirred overnight. The reaction mixture was diluted with CH$_2$Cl$_2$ and water was added. The layers were separated and the aqueous layer was extracted with CH$_2$Cl$_2$. The combined organic layers were dried (MgSO$_4$) and concentrated under reduced pressure. The residue was purified by flash chromatography (SiO$_2$, 10-35% EtOAc/hexanes) to give 7.47 g of the desired compound 99% yield). LC-MS R$_t$(retention time): 2.50 min and 2.58 min (two rotamers), MS: (ES) m/z 370 (M+H$^+$).

d) Lithium aluminum hydride solution (2.0 M in THF, 8.2 mL, 16.4 mmol) was added to a solution of the ester from step c (2.98 g, 8.06 mmol) in THF (100 ml) at 0° C. The resulting solution was kept stirring at 0° C. for 2 h at which time the reaction was completed. 15% Aqueous NaOH (625 µL) was added drop wise to quench the reaction followed by H$_2$O (625 µL). To the cloudy colloidal mixture was added additional water (1.85 mL), and the mixture was kept stirring for 1 h at rt. The mixture was then filtered through a celite plug, and the filtrate was concentrated under reduced pressure. Purification by flash chromatography (SiO$_2$, 33-67% EtOAc/hexanes) gave 2.46 g of the desired product (93% yield). LC-MS: R$_t$ (retention time): 1.90 min and 2.09 min (two rotamers), MS: (ES) m/z 328 (M+H$^+$).

e) A solution of the alcohol from step d (1.42 g, 4.33 mmol,) in acetic acid (65 ml) was added to a slurry of CrO$_3$ (2.61 g, 26.1 mmol) in H$_2$O (16 ml) at room temperature. The resulting mixture was kept stirring at room temperature until the reaction was completed (90 min). The mixture was filtered through a Celite plug and the filtrate was concentrated under reduced pressure. Purification by flash chromatography (SiO$_2$, 3-10% CH$_2$Cl$_2$:MeOH followed by 50-67% EtOAc/hexanes) gave 1.03 g of the desired product (70% yield). LC-MS: R$_t$ (retention time): 1.88 min and 2.12 min (two rotamers), MS: (ES) m/z 342 (M+H$^+$).

f) 3-Trifluoromethylaniline (16.2 mg, 0.1 mmol, 1.0 eq) was added to a solution of the acid prepared above (34.2 mg, 0.1 mmol) and triethylamine (6 eq) in CH$_2$Cl$_2$ (1 mL). T3P (95.5 mg, 0.15 mmol) was then slowly added and the solution was allowed to stir at room temperature for 1.5 h. The reaction mixture was diluted with CH$_2$Cl$_2$ (1 mL), washed with 1 N aqueous HCl followed by saturated aqueous NaHCO$_3$. The organic layer was separated, dried over anhydrous MgSO4, and concentrated under reduced pressure Purification by flash chromatography (SiO$_2$, 5-40% EtOAc/hexanes) gave 35 mg (73% yield) of the product as a white solid. $^1$H NMR (400 MHz, CDCl$_3$) δ ☐1.22-2.45 (m, 8H), 2.93-3.32 (m, 3H), 6.77-7.82 (m, 12H), 9.10 (s, 0.38H), 9.30 (s, 0.62H). LC-MS: R$_t$(retention time)=2.88 min, MS: (ES) m/z 485 (M+H$^+$).

Example 2

Synthesis of N-(3-tert-butylphenyl)-1-(5-chloro-3-methylpicolinoyl)-2-phenylpiperidine-3-carboxamide

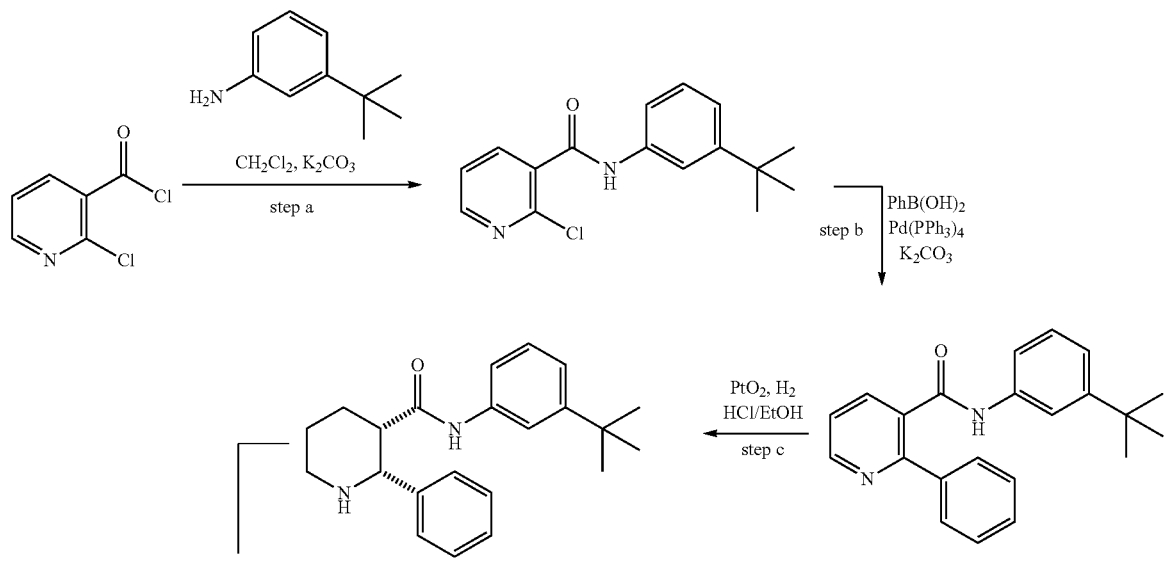

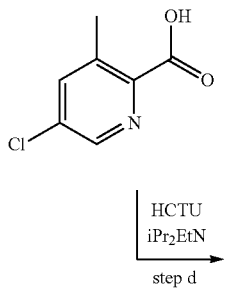

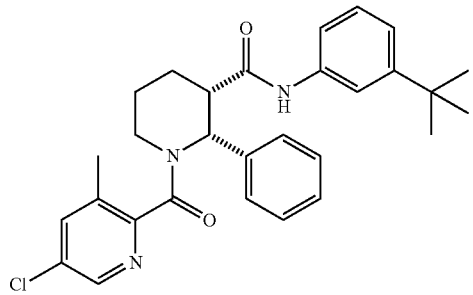

a) 2-Chloronicotinoyl chloride (1.05 eq) dissolved in anhydrous dichloromethane (0.5 M) was added to a solution of 3-tert-butylaniline (1 eq) and 2 M aq $K_2CO_3$ (2.2 eq) in anhydrous dichloromethane (0.5 M) at 0° C. over a period of 30 min, and the reaction mixture was allowed to stir at room temperature for an additional 1.5 h. The layers were separated and the aqueous layer was extracted with dichloromethane. The combined organic layer was washed with brine, dried ($MgSO_4$), filtered and concentrated to give the desired amide as a foamy solid which was used as such in the next step without further purification. MS: (ES) m/z 289.1 (M+H$^+$).

b) Pd(PPh$_3$)$_4$ (2-5 mol %) was added to a solution of the above pyridine amide (1 eq), phenylboronic acid (1.4 eq) and 2 M aq $K_2CO_3$ (2.4 eq) in toluene (0.7 M) and the reaction mixture was heated at 100° C. over night (~12 h). After cooling to room temperature, the reaction mixture was filtered through celite and the celite plug was washed with EtOAc. The filtrate was diluted with water and extracted with EtOAc, dried ($MgSO_4$), filtered and concentrated and concentrated under reduced pressure. The residue was purified by automated flash chromatography ($SiO_2$, 10% to 100% gradient of EtOAc-hexanes) and dried in vacuo to give the 2-phenyl-3-carboxyamidepyridine in 60-75% yield, MS: (ES) m/z 331.2 (M+H$^+$).

c) PtO$_2$ (10 mol %) was added to a solution of the 2-phenylpyridine derivative prepares above (1 eq) in EtOH and concentrated HCl (excess, 4:1 ratio) and the reaction mixture was hydrogenated using a Parr shaker at 40-45 psi, for 1.5 h. It was filtered through celite, washed with EtOH, and the filtrate was concentrated. The residue was diluted with CH$_2$Cl$_2$ and washed with saturated aq NaHCO$_3$. The residue was then purified by automated flash chromatography (SiO$_2$, 1% to 30% gradient of CH$_2$Cl$_2$-MeOH) and dried in vacuo to give the title compound in ~85% yield as a foamy solid. MS: (ES) m/z 337.2 (M+H$^+$).

d) 5-Chloro-3-methylpicolinic acid (30 mg, 0.16 mmol) and N-(3-tert-butylphenyl)-2-phenylpiperidine-3-carboxamide (50 mg, 0.15 mmol, prepared in step c above) were dissolved in anhydrous DMF (1 mL). N,N-Diisopropylethylamine (0.15 mL) was added at room temperature followed by HCTU (67 mg, 0.16 mmol). After stirring 2 h at ambient temperature, LC-MS and TLC indicated the completion of the reaction. The reaction mixture was diluted with EtOAc (50 mL) and washed with 1 N HCl (20 mL), saturated NaHCO$_3$ (30 mL), and brine (30 mL) and the resulting solution was concentrated under reduced pressure. The residue was purified by preparative HPLC (20→95% gradient of MeCN—H$_2$O with 0.1% TFA) and the pure fractions were lyophilized to afford the title compound (50 mg, 67% yield). HPLC retention time=2.88 minutes. $^1$H NMR (400 MHz, CDCl$_3$) δ 8.42 (d, 1H, J=0.8 Hz), 7.97 (br, 1H), 7.59 (d, 1H, J=0.8 Hz), 7.56 (d, 1H, J=7.6 Hz), 7.34 (m, 3H), 7.20 (m, 3H), 7.10 (d, 1H, J=7.6 Hz), 6.61 (two sets of br, 1H), 3.12 (two sets of m, 2H), 2.94 (three sets of m, 1H), 2.36 (s, 3H), 2.20 (two sets of br, 2H), 1.74 (br complex, 2H), 1.29 (s, 9H). MS: (ES) m/z 490.2 (M+H$^+$).

Example 3

Synthesis of cis-1-(2-methylbenzoyl)-2-(3-fluorophenyl)piperidine-3-carboxylic acid (3-tert-butylphenyl)amide

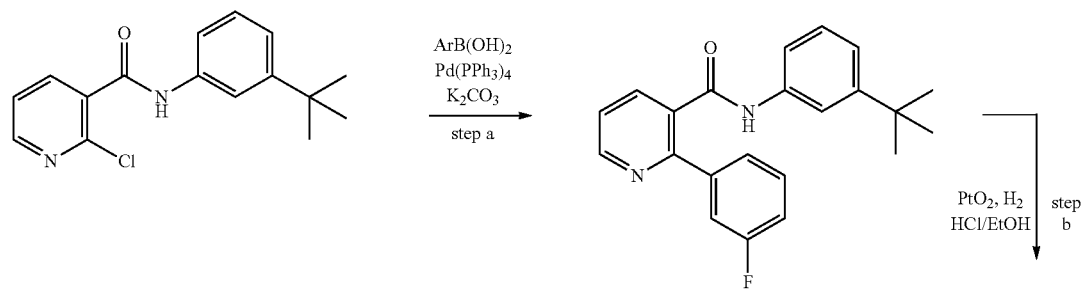

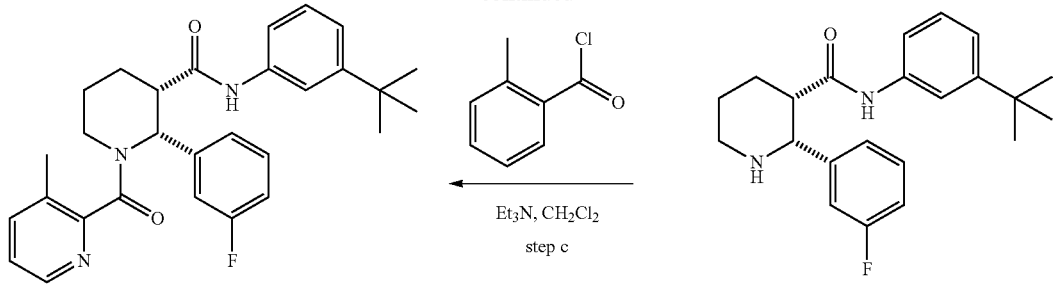

a) To a mixture of N-(3-tert-butylphenyl)-2-chloronicotinamide (570.2 mg, 2 mmol), 3-fluorophenylboronic acid (401.2 mg, 2.8 mmol), 3 mL of toluene, and 1 mL of 2 N potassium carbonate in water was added tetrakis(triphenylphosphine)palladium(0) (234.5 mg, 0.2 mmol). The mixture was then heated at 90° C. for 3 hour under nitrogen, before it was cooled down to room temperature. The reaction mixture was then diluted with 30 mL of water and 150 mL of EtOAc. The organic layer was separated, washed with brine, and dried ($Na_2SO_4$). The organic solvent was removed under reduced pressure and the residue was purified by silica gel column (40% EtOAc in hexane) to give N-(3-tert-butylphenyl)-2-(3-fluorophenyl)nicotinamide (691.4 mg, 99%). MS: (ES) m/z 394.5 (M+H$^+$).

b) A mixture of N-(3-tert-butylphenyl)-2-(3-fluorophenyl)nicotinamide (501.2 mg, 1.4 mmol), platinum oxide (51.9 mg, 0.21 mmol), and concentrated HCl (400 μL, 5.2 mmol) in 5 mL of ethanol was stirred vigorously under hydrogen balloon overnight. The mixture was filtered, and the solids washed with 25 mL of methanol three times. The combined solution was dried under reduced pressure. To the residue was added 30 mL of saturated sodium bicarbonate and 150 mL of EtOAc. The organic layer was separated, and dried over sodium sulfate. Evaporation of solvent gave the crude 2-(3-fluorophenyl)piperidine-3-carboxylic acid (3-tert-butylphenyl)amide as a brown solid, which was taken on directly to the next step. MS: (ES) m/z 355.7 (M+H$^+$).

c) To a solution of 2-(3-fluorophenyl)piperidine-3-carboxylic acid (3-tert-butylphenyl)amide (prepared above, 177.3 mg, 0.5 mmol) in 2 mL of dichloromethane was added Et$_3$N (100 μL, excess), and 2-methylbenzoyl chloride (92.3 mg, 0.6 mmol) at room temperature. The resulting solution was then stirred at this temperature until completion of the reaction (10 min.). The reaction mixture was then directly loaded onto a silica gel column, and was purified by using ISCO (30% EtOAc in hexane) to give the final product 2-(3-fluorophenyl)-1-(2-methylbenzoyl)piperidine-3-carboxylic acid (3-tert-butylphenyl)amide (151.2 mg, 64% yield). $^1$H NMR (400 MHZ, CDCl$_3$, mixture of rotomers): δ 7.91 (s, 0.6H), 7.85 (s, 0.4H), 7.18-7.46 (m, 9H), 7.11 (m, 1H), 6.95 (m, 1H), 6.67 (d, J=1.2 Hz, 1H), 3.36 (d, J=1.6 Hz, 0.4H), 3.26 (d, J=1.6 Hz, 1H), 3.05 (m, 1H), 2.89 (t, J=1.2 Hz, 1H), 2.45 (s, 1H), 2.02-2.40 (m, 4H), 1.70-1.84 (m, 3H), 1.44-1.64 (s, 1H), 1.32 (s, 6H), 1.25 (s, 1H). MS: (ES) m/z 473.2 (M+H$^+$).

Example 4

Synthesis of cis-1-(2-methylbenzoyl)-2-(2,2-dimethylpropyl)piperidine-3-carboxylic acid (3-tert-butylphenyl)amide

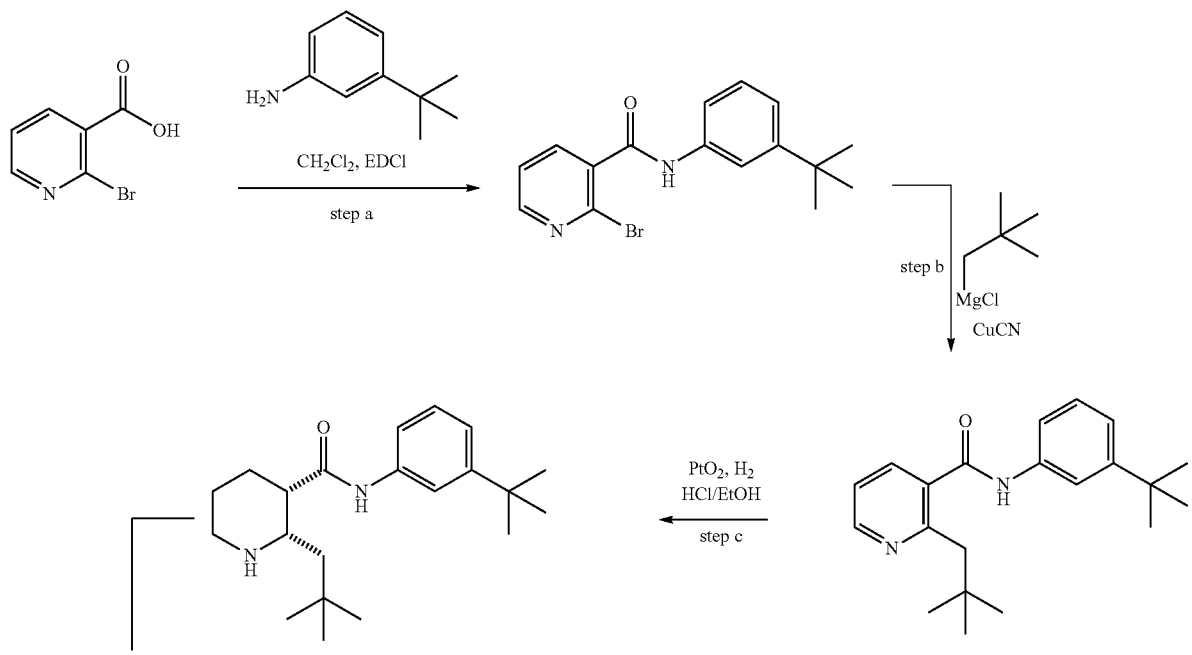

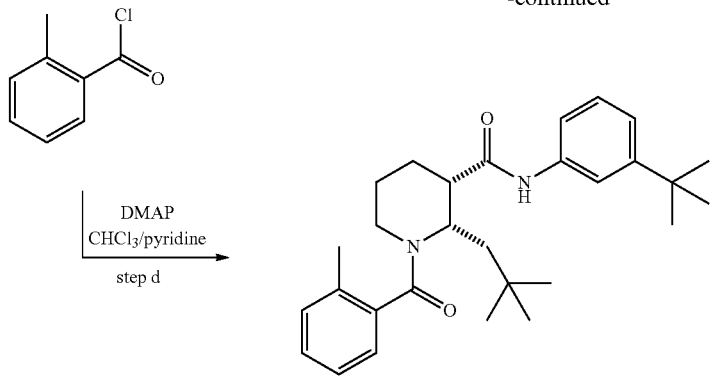

a) To a stirred solution of 2-bromonicotinic acid (1.01 g, 5 mmol) dissolved in anhydrous dichloromethane (8 mL) were added EDCI (1.34 g, 7 mmol) and 3-tert-butylaniline (0.74 g, 5 mmol) at room temperature and the reaction mixture was stirred for 12 hours. The mixture was then diluted with dichloromethane, followed by saturated sodium bicarbonate and water wash. The dichloromethane layer was dried over anhydrous magnesium sulfate, filtered and concentrated under reduced pressure. The residue was purified by flash chromatography to obtain 2-bromo-N-(3-tert-butylphenyl)nicotinamide in 59% yield (950 mg). Rt: 2.44 min (20-100-5 method). MS: (ES) m/z 333, 335 (M+H$^+$).

b) 2, 2-Dimethylpropylmagnesium chloride (1 M-diethylether, 4.8 mL, 4.8 mmol) was added to a suspension of copper cyanide (215 mg, 2.40 mmol) in THF (6 mL) at −78° C. After stirring at the same temperature for 1 hour, 2-bromo-N-(3-tert-butylphenyl)nicotinamide (200 mg, 0.601 mmol) was added all at once as a solid. The reaction mixture was gradually warmed to room temperature and the reaction was allowed to stir overnight. Saturated ammonium chloride solution and ethyl acetate was added, and the reaction mixture was filtered through celite and rinsed with ethyl acetate. The layers were separated and the product was extracted once more with ethyl acetate. The combined organic layers were washed with brine and dried over anhydrous sodium sulfate. After removing the solvent under reduced pressure, the crude material was purified using silica gel column chromatography using a gradient of 20%-50% ethyl acetate in hexanes to yield N-(3-tert-butylphenyl)-2-(2, 2-dimethylpropyl)nicotinamide (168 mg, 0.517 mmol, 86%). Rf=0.45 (toluene:ethyl acetate=2:1).

c) N-(3-tert-Butylphenyl)-2-(2, 2-dimethylpropyl)nicotinamide (168 mg, 0.517 mmol) was dissolved in ethanol (5 mL). Platinum oxide (11.6 mg, 0.0511 mmol) was added followed by concentrated hydrochloric acid (250 µL). The reaction mixture was hydrogenated using a Parr apparatus for 1.5 hours at 45 psi. Analysis of the reaction mixture showed incomplete conversion, and the sequence was repeated one more time. Platinum oxide was filtered off and the solvents were removed under reduced pressure. The crude material was neutralized using saturated sodium bicarbonate solution and extracted with ethyl acetate. The organic layer was then washed with brine and dried over anhydrous magnesium sulfate. Removal of solvent under reduced pressure gave the crude 2,3-cis-2-(2,2-dimethylpropyl)piperidine-3-carboxylic acid-(3-tert-butylphenyl)amide (153 mg) which was used in the next step without further purification.

d) To a solution of 2,3-cis-2-(2,2-dimethylpropyl)piperidine-3-carboxylic acid-(3-tert-butylphenyl)amide (84.8 mg, 0.257 mmol) in pyridine (415 µL, 5.13 mmol) at room temperature was added 2-methylbenzoyl chloride (81.6 mg, 0.528 mmol) in chloroform (415 µL). A catalytic amount (not weighed) of dimethylaminopyridine was added to enhance the reaction and the mixture was stirred for three days. Ethyl acetate and water was then added to the reaction mixture and the product was extracted with ethyl acetate three times. The combined organic layers were dried over anhydrous magnesium sulfate. After removal of the solvent under reduced pressure the crude material was purified via silica gel chromatography using 10%-20% ethyl acetate in hexanes to give 2,3-cis-2-(2,2-dimethylpropyl)-1-(2-methylbenzoyl)piperidine-3-carboxylic acid-(3-tert-butylphenyl)amide (47.0 mg, 0.105 mmol, 41%). Rf=0.6 (hexanes: ethyl acetate=2:1). Rt=3.16 min., 3.26 min. (compound exists as mixtures of several conformers. 20-100-5 method.). $^1$H NMR (CDCl$_3$) δ 9.68 (s, 1H), 9.43 (s, 1H), 8.33 (s, 1H), 8.28 (s, 1H)), 6.97-7.79 (m, 8H), 5.48 (br, 1H), 5.39 (dd, J=4, 10 Hz, 1H), 5.33 (dd, J=6, 6 Hz, 1H), 3.38 (ddd, J=4, 14, 14 Hz, 2H), 3.25 (dd, J=13, 13 Hz, 2H), 2.66 (dd, J=4, 8.4 Hz, 1H), 2.63 (ddd, J=2.8, 2.8, 8 Hz, 1H), 2.50 (s, 9H), 2.40 (s, 9H), 2.25 (s, 9H), 2.13 (s, 9H), 1.79-1.99 (m, 2H), 1.23-1.56 (m, 2H), 1.32 (s, 9H), 1.07 (s, 9H), 1.06 (s, 9H), 0.97 (s, 9H), 0.95 (s, 9H). MS: (ES) m/z 449 (M+H$^+$).

Example 5

Synthesis of cis-2-cyclopentyl-1-(2-methylbenzoyl)piperidine-3-carboxylic acid (3-tert-butylphenyl)amide

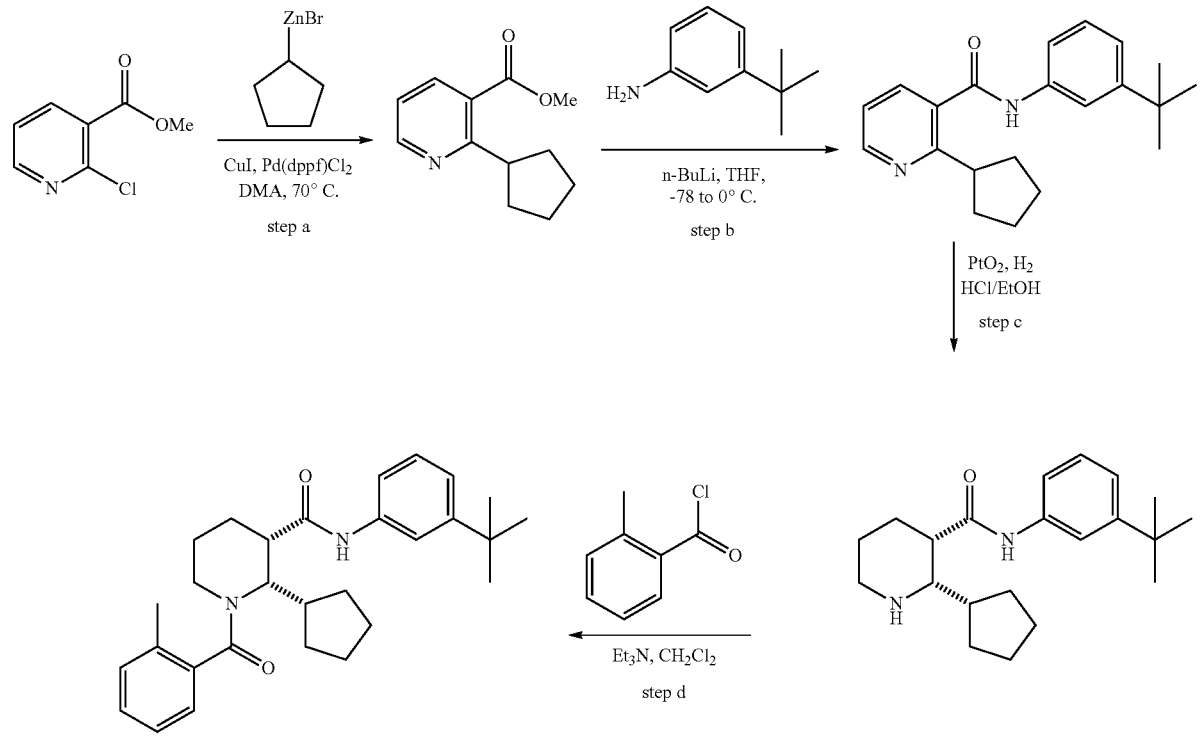

a) Cyclopentylzinc bromide (0.5 M, 6.5 mL, 3.26 mmol) was added to a room temperature stirred solution of the 2-chloronicotinic acid methyl ester (400 mg, 2.33 mmol), CuI (19 mg, 0.1 mmol) and Pd(dppf)Cl$_2$ (42 mg, 0.06 mmol) in anhydrous dimethylacetamide (1.7 mL) under nitrogen. The reaction mixture was heated to 70° C. for 3.5 hours, cooled to room temperature, filtered through celite, and the cake was rinsed with ethyl acetate. The filtrate was washed with water, brine, dried (MgSO$_4$), filtered and concentrated under reduced. The residue was purified by flash chromatography (SiO$_2$, 10-100% EtOAc/hexanes) to get the desired compound in 83% yield (400 mg). LC-MS R$_t$(retention time): 1.87 min; MS: (ES) min 206 (M+H$^+$).

b) n-BuLi (1.47 mL, 3.68 mmol) was added to the 3-tert-butylaniline (580 mg, 3.89 mmol) at −78 OC in dry THF (2 mL) under nitrogen and the solution was allowed to stir at 0° C. for 10 minutes. The reaction mixture was re-cooled to −78° C. and 2-cyclopentyl-nicotinic acid methyl ester (400 mg, 1.94 mmol) dissolved in dry THF (2 mL) was added to it. The reaction mixture was allowed to attain 0° C. over a period of 2 hours, quenched with saturated aqueous NH$_4$Cl, and extracted with ethyl acetate. The combined organic layers were dried (MgSO$_4$), filtered and concentrated under reduced pressure. The residue was purified by flash chromatography (SiO$_2$, 10-100% EtOAc/hexanes) to give the pure compound in 91% yield (572 mg). LC-MS R$_t$ (retention time): 2.61 min; MS: (ES) m/z 323 (M+H$^+$).

c) To a solution of the N-(3-tert-butylphenyl)-2-cyclopentylnicotinamide (570 mg, 1.77 mmol) in ethanol (10 mL) containing concentrated HCl (1 mL) was added platinum oxide (40 mg, 0.17 mmol) and the solution was hydrogenated using a Parr shaker at 40 psi for 1.5 hour. The reaction mixture was filtered through Celite, and the cake was rinsed with ethanol. The filtrate was concentrated, and the residue was dried under high vacuum for 2 hours to get quantitative yield of the desired piperidine as a HCl salt. LC-MS R$_t$ (retention time): 1.97 min; MS: (ES) m/n 329 (M+H$^+$).

d) To a solution of the cis-2-cyclopentylpiperidine-3-carboxylic acid (3-tert-butyl-phenyl)amide prepared above (123 mg, 0.34 mmol) in dry CH$_2$Cl$_2$ (1 mL) containing Et$_3$N (142 μL, 1.02 mmol) was added 2-methylbenzoyl chloride (53 mg, 0.34 mmol) and the mixture was stirred at room temperature for 2 hours. The reaction mixture was then diluted with ethyl acetate (20 mL), washed with 1 N aqueous HCl, water, and brine. The organic layer was dried (MgSO$_4$), filtered and concentrated under reduced pressure. The residue was purified by reverse phase preparative HPLC (20-95% gradient of CH$_3$CN—H$_2$O) and dried (Lyophilizer) to give the title compound in 65% yield (109 mg). $^1$H NMR (400 MHz, CDCl$_3$): δ 1.22-1.48 (☐m, 11H), 1.56-1.80 (m, 5H), 1.84-2.06 (m, 4H), 2.10-2.23 (m, 1H), 2.30 (s, 1.6H), 2.39 (s, 1.4H), 2.41-2.50 (m, 1H), ☐ 2.71-2.76 (☐☐m, 1H), 3.02-3.09 (m, 1H), 3.25-3.39 (m, 1H), 5.11 (bs, 1H), 7.05-7.30 (m, 6H), 7.47-7.55 (m, 2H), 8.32 (bs, 1H). LC-MS R$_t$ (retention time): 3.16 min; MS: (ES) m/z 447 (M+H)$^+$. LC-MS method: Agilent Zorbax SB-C18, 2.1×50 mm, 5μ, 35° C. 1 mL/min flow rate, a 2.5 min gradient of 20% to 100% B with a 1.0 min wash at 100% B; A=0.1% formic acid/5% acetonitrile/94.9 water, B=0.1% formic acid/5% water/94.9 acetonitrile.

Example 6

Synthesis of (2R,3S)-2-(4-Cyclopentylaminophenyl)-1-(2-methylbenzoyl)piperidine-3-carboxylic acid(3-chloro-4-methylphenyl)amide

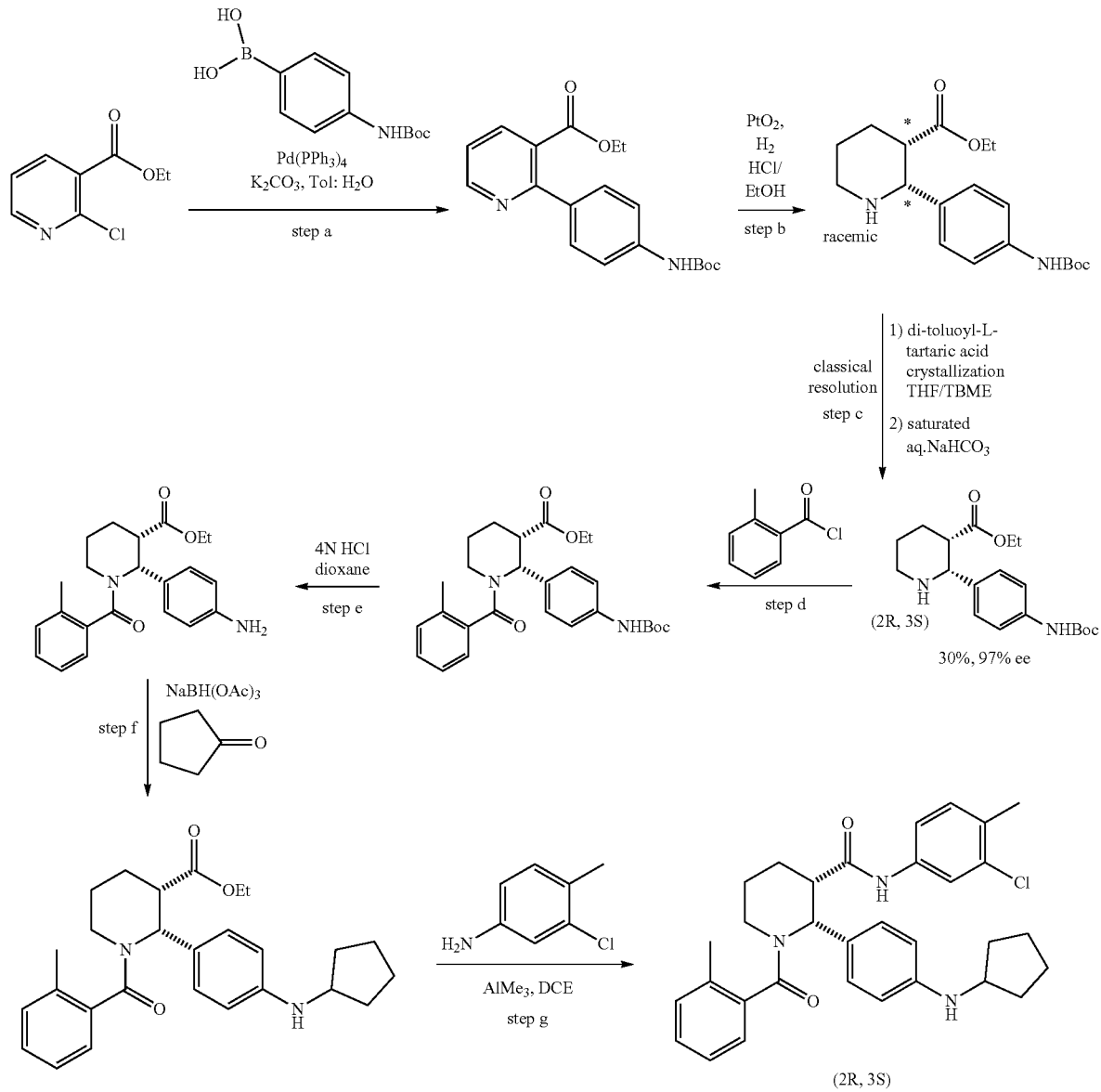

b) cis-2-(4-tert-Butoxycarbonylaminophenyl)piperidine-3-carboxylic acid ethyl ester was synthesized similarly as illustrated in example 1.

c: 1): cis-2-(4-tert-Butoxycarbonylaminophenyl)piperidine-3-carboxylic acid ethyl ester (61 g, 174.8 mmol) and di-p-toluoyl-L-tartaric acid (62 g, 174.8 mmol) was dissolved in EtOH (500 ml). The clear solution was concentrated and pumped to dry. The obtained white salt was then dissolved into 250 ml of ethyl acetate to form a clear solution. To this solution was added 500 ml of TBME slowly. The obtained solution was left at rt undisturbed for 3 days. At this time a lot of white crystals were formed. They were then filtered and washed with 100 ml of TBME to obtain a white solid (60 g).

The above salt was re-dissolved in ethanol, concentrated and pumped to dry. The obtained salt was dissolved into 500 ml of THF, followed by adding TBME (500 ml). The obtained clear solution was left at rt undisturbed for another 2.5 days. The obtained white crystals were filtered to obtain 20.5 g (enrichment 64:1) of the salt.

c:2) To a 0° C. stirred suspension of the salt (16.7 g) in CH$_2$Cl$_2$ (150 mL) was added saturated aqueous NaHCO$_3$ solution (100 mL) and the reaction mixture was allowed to stir at r.t over a period of 30 minutes. The layers were separated and the aqueous layer was extracted with CH$_2$Cl$_2$ (50 mL). The combined organic layer was washed with saturated aqueous NaHCO$_3$ (2×100 mL), dried and concentrated to give (2R,3S)-2-(4-tert-Butoxycarbonylaminophenyl)piperidine-3-carboxylic acid ethyl ester in 90% yield and ~ in 97% ee.

d) To a 0° C. solution of the (2R,3S)-2-(4-tert-Butoxycarbonylaminophenyl)-piperidine-3-carboxylic acid ethyl ester prepared above (600 mg, 1.72 mmol) in dry $CH_2Cl_2$ (5 mL) containing $Et_3N$ (480 μL, 3.44 mmol) was added 2-methylbenzoyl chloride (266 mg, 1.72 mmol) and the mixture was stirred at room temperature for over night. The reaction mixture was then diluted with $CH_2Cl_2$ (20 mL), washed with 1 N aqueous HCl, water, and brine. The organic layer was dried ($MgSO_4$), filtered and concentrated under reduced pressure to give (2R,3S)-2-(4-tert-Butoxycarbonylaminophenyl)-1-(2-methylbenzoyl)piperidine-3-carboxylic acid ethyl ester in quantitative yield and the crude product was used as such in the next step.

e) 4N HCl in 1,4-dioxane (5 mL, 20 mmol) was slowly added to a 0° C. solution of the above crude product (2R,3S)-2-(4-tert-Butoxycarbonylaminophenyl)-1-(2-methylbenzoyl)piperidine-3-carboxylic acid ethyl ester (840 mg, 1.72 mmol) in dry $CH_2Cl_2$ (4 mL). After the addition of the HCl, the reaction mixture was allowed to attain r.t and stirred for 1 h. It was diluted with $CH_2C_2$ (30 mL), cooled to 0° C. and neutralized with saturated aqueous $NaHCO_3$ to get the (2R,3S)-2-(4-aminophenyl)-1-(2-methylbenzoyl)piperidine-3-carboxylic acid ethyl ester (612 mg) in 97% yield over two steps.

f) $Na(OAC)_3BH$ (495 mg, 2.33 mmol) was added to a solution of the (2R,3S)-2-(4-aminophenyl)-1-(2-methylbenzoyl)piperidine-3-carboxylic acid ethyl ester (612 mg, 1.67 mmol), cyclopentanone (140 mg, 1.67 mmol) and acetic acid (100 mg, 1.67 mmol) in dry dichloroethane at r.t and the reaction mixture was heated to 50° C. for 4 h, cooled to r.t and stirred for 48 h. It was then diluted with $CH_2Cl_2$ (30 mL), washed with saturated aqueous $NaHCO_3$ solution, dried and concentrated in vacuo. The residue was purified by ISCO flash column using ethyl acete and hexanes as mobile phase (40 g column, 0-40% gradient) to afford (2R,3S)-2-(4-Cyclopentylaminophenyl)-1-(2-methylbenzoyl)piperidine-3-carboxylic acid ethyl ester (450 mg).

g) $Me_3Al$ (290 μL, 0.57 mmol, 2M in toluene) was added to a solution of the 3-Chloro-4-methylphenylamine (65 mg, 0.46 mmol) in dry dichloroethane (1 mL) at ambient temperature. Stirred for 20 minutes, then (2R,3S)-2-(4-Cyclopentylaminophenyl)-1-(2-methylbenzoyl)piperidine-3-carboxylic acid ethyl ester (100 mg, 0.23 mmol) dissolved in dry dichloroethane (1 mL) was added to it. The reaction mixture was then heated to 85° C. for 3 h, cooled to r.t, diluted with $CH_2Cl_2$ (20 mL), washed with saturated aqueous $NaHCO_3$ solution. The aqueous layer was extracted with $CH_2Cl_2$ (20 mL) and the combined organic layer was dried ($MgSO_4$) and concentrated. The residue was purified by reverse phase preparative HPLC (20-95% gradient of $CH_3CN$—$H_2O$ with 0.1% TFA as additive), the product containing fractions were pooled together and concentrated. The residue was diluted with $CH_2Cl_2$ (30 mL), washed with saturated aqueous $NaHCO_3$ solution. The $CH_2Cl_2$ layer was dried ($MgSO_4$) and concentrated to get the pure (2R,3S)-2-(4-Cyclopentylaminophenyl)-1-(2-methylbenzoyl)piperidine-3-carboxylic acid (3-chloro-4-methylphenyl)amide in 50% yield.

$^1$H NMR (400 MHz, $CDCl_3$) δ ☐8.4 (bs, 1H), 7.55 (s, 1H), 7.37-7.05 (m, 9H), 6.55-6.52 (m, 2H), 3.77-3.70 (m, 1H), 3.30-3.16 (m, 1H), 3.04-2.91 (m, 2H), 2.43-1.94 (m, 8H), 1.71-1.46 (m, 11H).

Example 7

Synthesis of ethyl (2R,3S)-2-[4-(cydopentylamino) phenyl]-1-(2-fluoro-6-methylbenzoyl)piperidine-3-carboxylate

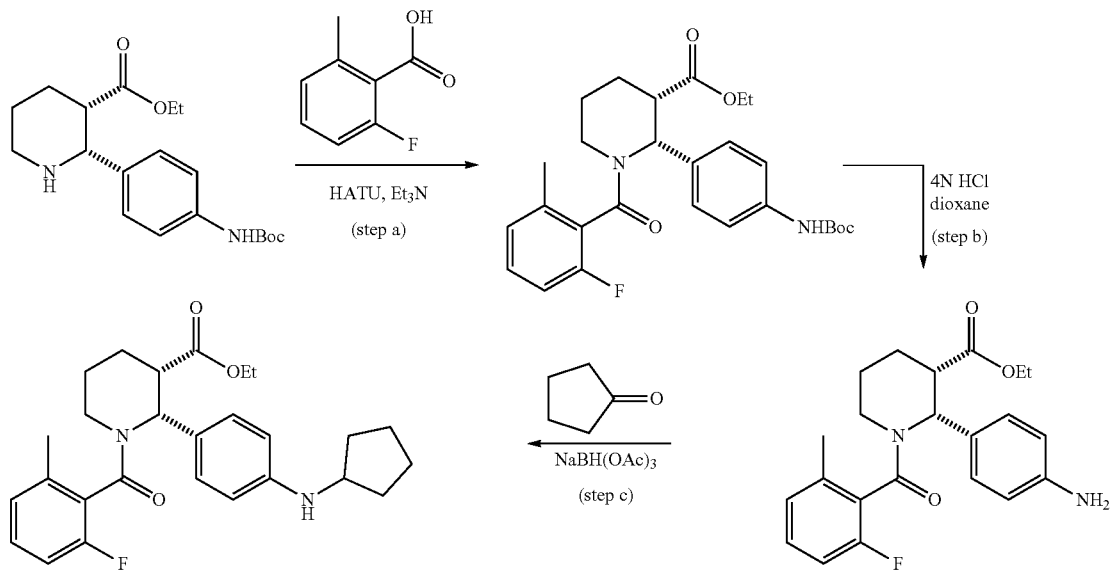

Step a) To a solution of (2R,3S)-2-(4-tert-butoxycarbonylaminophenyl)-piperidine-3-carboxylic acid ethyl ester (13.74 g, 39.36 mmol, prepared as in WO 2010/075257), 2-fluoro-6-methylbenzoic acid (6.37 g, 41.33 mmol) and $Et_3N$ (14.4 mL, 102.3 mmol) in dry DMF (110 mL) at 0° C. was added HATU (15.71 g, 41.33 mmol) and the mixture was then stirred at room temperature for 3 h. The reaction mixture was then diluted with water, extracted with ethyl acetate, and washed with brine. The combined organic layers were dried ($MgSO_4$), filtered, and concentrated under reduced pressure. The residue was purified by flash chromatography ($SiO_2$, 10-55% ethyl acetate in hexanes) to give 19 g (100%) of the product ethyl (2R,3S)-2-[4-(tert-butoxycarbonylamino)phenyl]-1-(2-fluoro-6-methylbenzoyl)piperidine-3-carboxylate. MS: (ES) m/z 485 (M+H$^+$)

Step b) 4 N HCl in 1,4-dioxane (110 mL, 440 mmol) was slowly added to a solution of the above ethyl (2R,3S)-2-[4-

(tert-butoxycarbonylamino)phenyl]-1-(2-fluoro-6-methyl-benzoyl)piperidine-3-carboxylate (19 g, 39.36 mmol) in dry $CH_2Cl_2$ (110 mL) at 0° C. After the addition of HCl, the reaction mixture was allowed to attain rt and stirred for 3 h. The solution was then diluted with ethyl acetate (200 mL), cooled to 0° C., and neutralized with saturated aqueous $NaHCO_3$ to get ethyl (2R,3S)-2-(4-aminophenyl)-1-(2-fluoro-6-methylbenzoyl)piperidine-3-carboxylate (15 g, 100%). MS: (ES) m/z 385 (M+H$^+$).

Step c) NaBH(OAc)$_3$ (14.12 g, 66.60 mmol) was added to a solution of ethyl (2R,3S)-2-(4-aminophenyl)-1-(2-fluoro-6-methylbenzoyl)piperidine-3-carboxylate (16 g, 41.65 mmol), and cyclopentanone (10.51 g, 125 mmol) in dry dichloroethane (200 mL) at rt. The reaction mixture was heated to 45° C. for 3 h, cooled to rt, quenched with saturated aqueous $NaHCO_3$ solution, extracted with dichloromethane, dried and concentrated in vacuo. The residue was purified by flash chromatography ($SiO_2$, ethyl acetate/hexanes 15-40%) to afford ethyl (2R,3S)-2-[4-(cyclopentylamino)phenyl]-1-(2-fluoro-6-methylbenzoyl)piperidine-3-carboxylate as white solid (17 g, 90%). MS: (ES) m/z 453 (M+H$^+$).

Synthesis of (2R,3S)-2-[4-(cyclopentylamino)phenyl]-1-(2-fluoro-6-methylbenzoyl)-N-[4-(hydroxymethyl)-3-(trifluoromethyl)phenyl]piperidine-3-carboxamide Step a) Ethyl (2R,3S)-2-[4-(cyclopentylamino)phenyl]-1-(2-fluoro-6-methyl-benzoyl)piperidine-3-carboxylate (2 g, 4.4 mmol) in 1,4-dioxane (9 mL) was added to 3 N aqueous HCl (6 mL) at room temperature and the reaction mixture was heated at 80° C. for 15 h. The solution was then cooled to 0° C. and neutralized with saturated aqueous $NaHCO_3$ and extracted with ethyl acetate. The ethyl acetate layer was concentrated under reduced pressure and the residue was purified by flash chromatography ($SiO_2$, 20% EtOAc in $CH_2Cl_2$) to get the desired acid (1.4 g, 74%). MS: (ES) m/z 425 (M+H$^+$).

Step b) Methanesulfonyl chloride (378 mg, 3.3 mmol) was added to a solution of (2R,3S)-2-[4-(cyclopentylamino)phenyl]-1-(2-fluoro-6-methyl-benzoyl)piperidine-3-carboxylic acid prepared above (1.4 g, 3.3 mmol) and Hunig's base (586 μL, 3.3 mmol) in dry $CH_2Cl_2$ (25 mL) at 0° C. under a nitrogen atmosphere. The solution was stirred for an additional 15 minutes, then [4-amino-2-(trifluoromethyl)phenyl]methanol (631 mg, 3.3 mmol) and Hunig's base (586 μL, 3.3 mmol) were added sequentially. The reaction mixture was allowed to attain room temperature over a period of 30 minutes. When TLC and LCMS indicated completion of the reaction, excess solvent was removed under reduced pressure. The residue was purified by flash chromatography (SiO2, 0-20% ethyl acetate in dichloromethane) to get the desired compound (1.2 g) in 61% yield. $^1$H NMR (400 MHz, CDCl$_3$) δ 9.50 (bs, 0.6H), 9.38 (bs, 0.4H), 7.75-7.70 (m, 1 H), 7.50-7.33 (m, 3H), 7.24-7.19 (m, 2H), 7.06-6.90 (m,

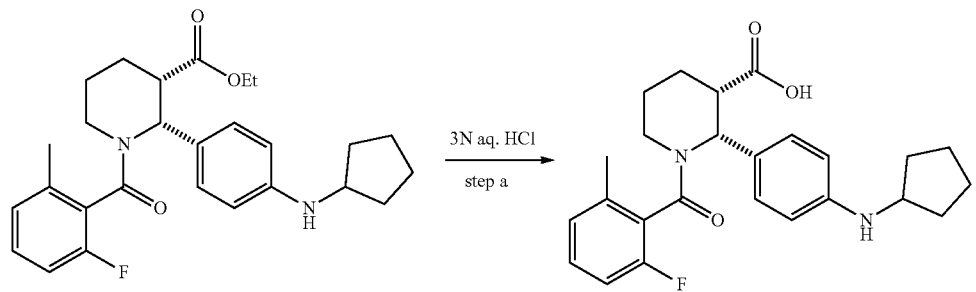

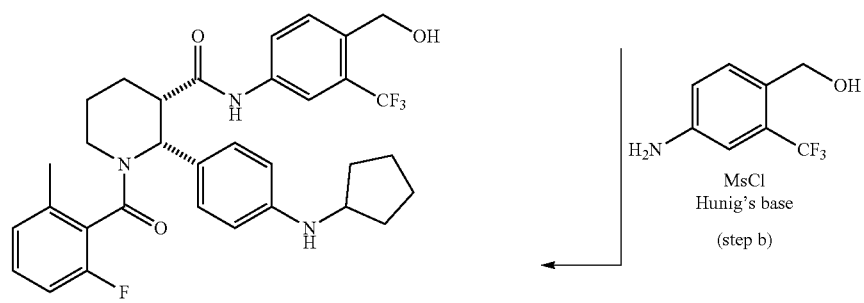

2H), 6.67-6.55 (m, 3H), 4.77-4.76 (m, 2H), 3.78-3.66 (m, 1H), 3.32-3.00 (m, 3H), 2.44-1.45 (m, 17H). MS: (ES) m/z 598 (M+H⁺).

Example 8

Synthesis of 4-[[(2R,3S)-2-[4-(cyclopentylamino) phenyl]-1-(2-fluoro-6-methyl-benzoyl)piperidine-3-carbonyl]amino]-2-(trifluoromethyl)benzoic acid

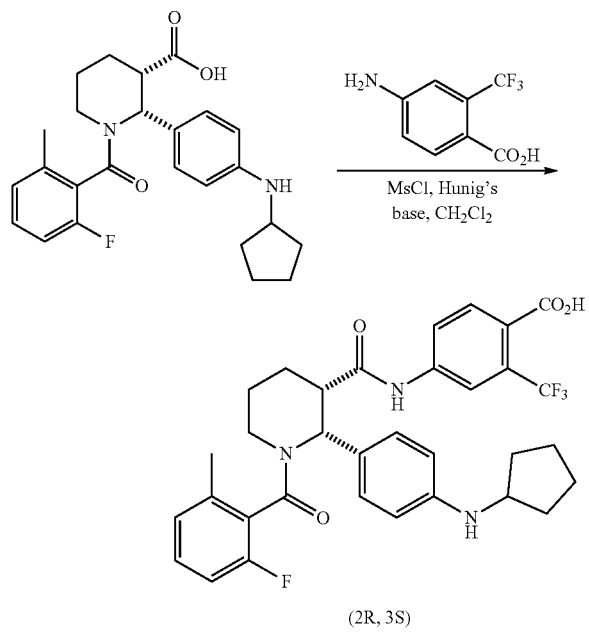

(2R, 3S)

The title compound was synthesized in similar fashion as the above example: ¹H NMR (400 MHz, CD₃OD) δ 10.4 (br, 1H), 8.05-7.65 (m, 4H), 7.36-6.95 (m, 5H), 6.50-6.47 (m, 1H), 3.92-3.94 (m, 1H), 3.50-3.21 (m, 3H), 2.50-1.59 (m, 18H). MS: (ES) m/z 612 (M+H⁺).

Example 9

Synthesis of cis-2-[4-(cyclopentylamino)phenyl]-1-(2-fluoro-6-methylbenzoyl)-N-[4-formyl-3-(trifluoromethyl)phenyl]piperidine-3-carboxamide

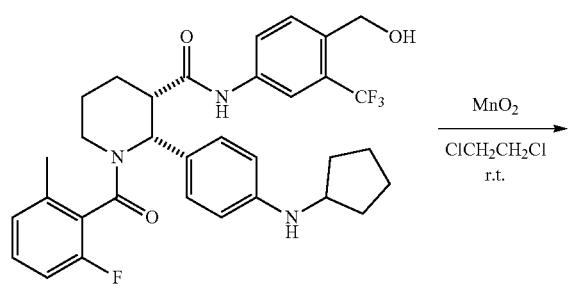

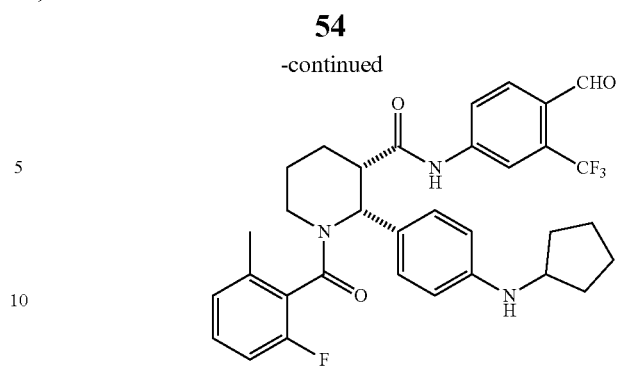

To a solution of cis-2-[4-(cyclopentylamino)phenyl]-1-(2-fluoro-6-methyl-benzoyl)-N-[4-(hydroxymethyl)-3-(trifluoromethyl)phenyl]piperidine-3-carboxamide (130 mg, 0.22 mmol) in 1,2-dichloroethane (2 mL) was added MnO₂ (380 mg, 4.4 mmol) at room temperature. The reaction mixture was stirred for 3 h and was then diluted with dichloromethane, filtered through a plug of SiO2, and the filtrate was concentrated under reduced pressure. The residue was purified by HPLC to get the desired compound (as a mixture of cis enantiomers) in 31% yield (40 mg). ¹H NMR (400 MHz, CDCl₃) δ 10.2 (bs, 1H), 8.12-6.88 (m, 10H), 3.82-3.04 (m, 4H), 2.88-1.40 (m, 18H). MS: (ES) m/z 596 (M+H⁺).

Example 10

(2R,3S)-2-(4-aminophenyl)-1-(2-fluoro-6-methyl-benzoyl)-N-[4-methyl-3-(trifluoromethyl)phenyl]piperidine-3-carboxamide

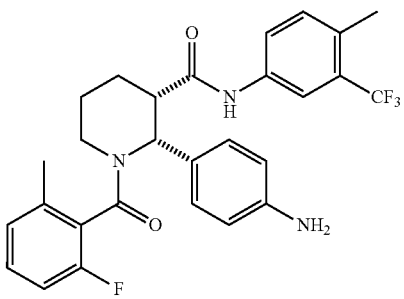

The title compound was synthesized in similar fashion as the above examples: ¹HNMR (400 MHz, CDCl₃) δ 9.21 (br, 0.6H), 8.91 (br, 0.4H), 7.67 (d, J=2.2 Hz, 0.4H), 7.60 (d, J=2.2 Hz, 0.6H), 7.51-7.47 (m, 1H), 7.41 (d, J=8.4 Hz, 1H), 7.33 (d, J=8.4 Hz, 1H), 7.24-7.03 (m, 2H), 6.95-6.84 (m, 2H), 6.68 (d, J=5.5 Hz, 1H), 6.62-6.60 (m, 1H), 3.65 (br, 2H), 3.28-2.96 (m, 3H), 2.44 (s, 1H), 2.41-2.38 (m, 3H), 2.11 (s, 3H), 1.80-1.74 (m, 1H), 1.70 (s, 3H). MS: (ES) m/z 514 (M+H⁺)

Example 11

The following are representative compounds prepared and evaluated using methods similar to the examples herein. Characterization data is provided for the compounds below. Biological evaluation is shown in FIGS. 1A-1QQQ for these compounds and others prepared as described herein.

(2R,3S)-2-(4-Cyclopentylaminophenyl)-1-(2-fluoro-6-methylbenzoyl)piperidine-3-carboxylic acid (4-methyl-3-trifluoromethylphenyl)amide

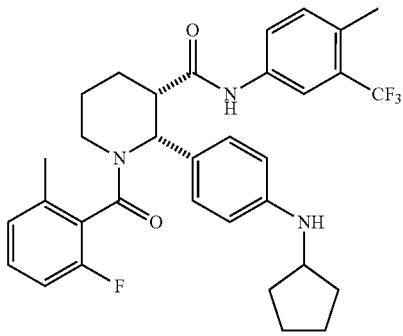

¹H NMR (400 MHz, TFA-d) δ 7.91 (d, J=8.6 Hz, 1H), 7.84 (d, J=8.6 Hz, 1H), 7.58-6.82 (m, 8H), 6.75 (1, J=8.6 Hz, 1H), 4.10-4.00 (m, 1H), 3.60-3.47 (m, 1H), 3.45-3.41 (m, 1H), 3.33-3.25 (m, 1H), 2.44-2.22 (m, 7H), 2.04-1.92 (m, 4H), 1.82-0.169 (m, 7H) (2R,3S)-1-(2-Chlorobenzoyl)-2-(4-cyclopentylaminophenyl)piperidine-3-carboxylic acid (4-methyl-3-trifluoromethylphenyl)amide

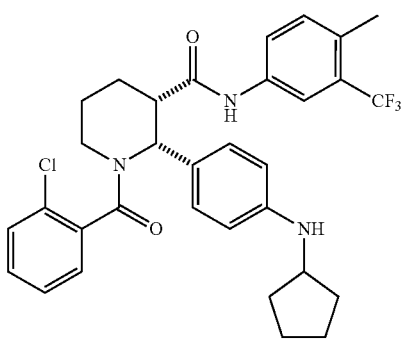

¹H NMR (400 MHz, CDCl₃) δ □9.41 (bs, 0.5H), 9.03 (bs, 0.5H), 7.55 (s, 1H), 7.49-7.39 (m, 3H), 7.31-7.27 (m, 2H), 7.18-7.04 (m, 2H), 6.83-6.74 (m, 3H), 3.76-3.64 (m, 1H), 3.22-2.90 (m, 5H), 2.39 (s, 3H), 2.32-2.20 (m, 1H), 2.16-2.04 (m, 1H), 2.0-1.86 (m, 2H) δ □1.80-1.72 (m, 3H), 1.56 (bs, 5H).

(2R,3S)-2-(4-Cyclopentylaminophenyl)-1-(2-fluoro-6-methylbenzoyl)piperidine-3-carboxylic acid (3-chloro-4-methylphenyl)amide

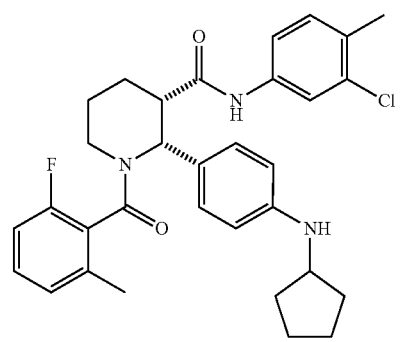

¹H NMR (DMSO-d₆) δ 10.22 (s, 1H), 7.67 (dd, J=1.8 Hz, J=11.0 Hz, 1H), 7.04-7.33 (m, 9H), 6.30 (dd, J=5.8 Hz, J=9.4 Hz, 1H), 5.52 (br, 1H), 3.56-3.64 (m, 1H), 3.00-3.17 (m, 2H), 2.90-2.98 (m, 1H), 2.23 (2.24) (s, 3H), 1.97 (2.33) (s, 3H), 1.32-2.22 (m, 12H)

(2R,3S)-1-(4-Chlorobenzoyl)-2-(4-Cyclopentylaminophenyl)piperidine-3-carboxylic acid (4-methyl-3-trifluoromethylphenyl)amide

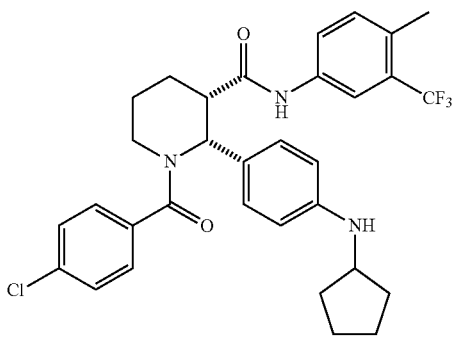

¹H NMR (400 MHz; CDCl₃) δ □8.79 (bs, 1H), 7.62 (s, 1H), 7.52-7.48 (m, 1H), 7.37-7.30 (m, 5H), 7.13 (d, J=8.4 Hz, 1H), 6.52-6.50 (m, 3H), 3.75-3.69 (m, 1H), 3.44 (bs, 1H), 3.09-2.97 (m, 2H), 2.39 (s, 3H), 2.37-2.30 (m, 1H), 2.13-2.08 (m, 1H), 2.10-1.93 (m, 2H), 1.80-1.59 (m, 7H), 1.48-1.42 (m, 2H)

(2R,3S)-2-(4-Cyclohexylaminophenyl)-1-(2-fluoro-6-methylbenzoyl)piperidine-3-carboxylic acid (3-ᵗ-butylphenyl)amide

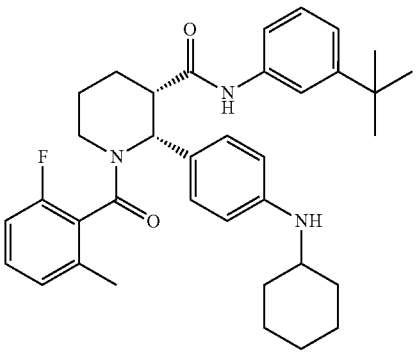 [SMILES: Cc1cccc(F)c1C(=O)N1CCC[C@H](C(=O)Nc2cccc(C(C)(C)C)c2)[C@@H]1c1ccc(NC2CCCCC2)cc1]

¹H NMR (400 MHz, CDCl₃): δ 8.24 (m, 1H), 7.40-6.85 (m, 8H), 6.65-6.40 (m, 3H), 3.57 (s, 1H), 3.30-2.90 (m, 4H), 2.50-1.85 (m, 9H), 1.80-1.50 (m, 5H), 1.40-1.00 (m, 13H)

(2R,3S)-2-(4-Cydopentylaminophenyl)-1-(2-fluoro-
6-methylbenzoyl)piperidine-3-carboxylic acid
(4-methyl-3-pyrrolidin-1-yl-phenyl)amide

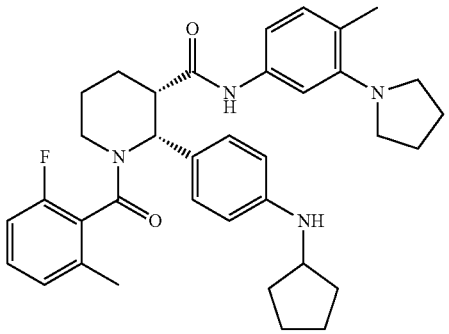 [SMILES: Cc1ccc(NC(=O)[C@H]2CCCN(C(=O)c3c(C)cccc3F)[C@H]2c2ccc(NC3CCCC3)cc2)cc1N1CCCC1]

¹H NMR (400 MHz, CDCl₃): δ 7.98 (m, 1H), 7.40-7.18 (m, 3H), 7.10-6.80 (m, 4H), 6.64-6.40 (m, 3H), 3.80-3.50 (m, 2H), 3.30-2.90 (m, 6H), 2.50-2.10 (m, 7H), 2.10-1.80 (m, 8H), 1.80-1.20 (m, 9H)

(2R,3S)-2-[4-(Cyclopentyloxy)phenyl]-1-(2-fluoro-
6-methylbenzoyl)piperidine-3-carboxylic acid
(3-chloro-4-methylphenyl)amide

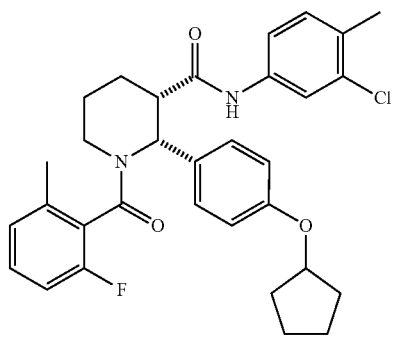

¹H NMR (400 MHz, CDCl₃) δ □8.68 (bs, 0.6H), 8.58 (bs, 0.4H), 7.59-7.40 (m, 3H), 7.29-6.90 (m, 4H), 6.80 (m, 2H), 6.65 (m, 1H), 4.72 (m, 1H), 3.30-2.92 (m, 3H), 2.44 (s, 1H), 2.42-2.30 (m, 1H), 2.30 (s, 1H), 2.29 (s, 2H), 2.20 (s, 2H), 2.19-2.12 (m, 1H), 2.08-1.92 (m, 2H), 1.90-1.72 (m, 7H) δ □1.60 (m, 2H).

(±)-(2R,3S)-2-(4-Cyclopentylaminophenyl)-1-(2-
fluoro-6-methylbenzoyl)piperidine-3-carboxylic acid
(4-chloro-3-methylphenyl)amide

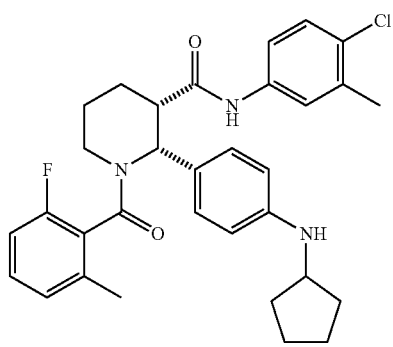

¹H NMR (400 MHz, CDCl₃) δ 8.25 (bs, 0.4H), 8.16 (bs, 0.6H), 7.44-7.20 (m, 6H), 7.06-6.84 (m, 2H), 6.59-6.50 (m, 2H), 3.75 (m, 1H), 3.66 (bs, 1H), 3.26-2.92 (m, 3H), 2.43 (s, 1H), 2.42-2.30 (m, 1H), 2.30 (s, 1H), 2.29 (s, 2H), 2.20 (s, 2H), 2.19-2.12 (m, 1H), 2.08-1.92 (m, 2H), 1.80-1.58 (m, 7H) δ □1.45 (m, 2H).

(2R,3S)-2-(4-Cyclobutylaminophenyl)-1-(2-fluoro-
6-methylbenzoyl)piperidine-3-carboxylic acid (3-ᵗ-
butylphenyl)amide

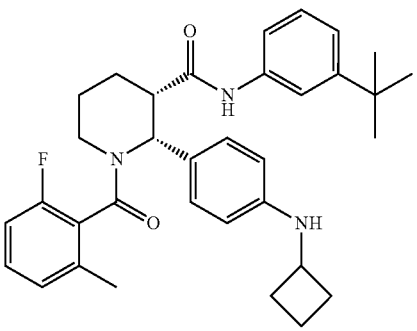 [SMILES: Cc1cccc(F)c1C(=O)N1CCC[C@H](C(=O)Nc2cccc(C(C)(C)C)c2)[C@@H]1c1ccc(NC2CCC2)cc1]

¹H NMR (400 MHz, CDCl₃) δ 8.20 (s, 0.6H), 8.39 (s, 0.4H), 7.44-6.88 (m, 10H), 6.25 (dd, J=12 Hz, J=6 Hz, 1H), 6.45 (t, J=8.4 Hz, 1H), 3.87 (m, 1H), 3.26-2.95 (m, 3H), 2.46-2.05 (m, 8H), 1.86-1.61 (m, 5H), 1.34-1.11 (m, 9H)

(2R,3S)-1-(2-fluoro-6-methylbenzoyl)-2-[4-(tetrahy-
dropyran-4-ylamino)phenyl]piperidine-3-carboxylic
acid (3-morpholin-4-yl-phenyl)amide

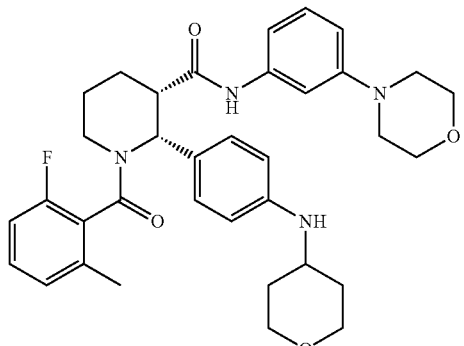

¹H NMR (400 MHz, CDCl₃) δ 7.61 (s, 1H), 7.34-6.92 (m, 10H), 6.78-6.65 (m, 1H), 6.62-6.53 (m, 1H), 3.98-3.85 (m, 4H), 3.83-3.70 (m, 1H), 3.55-3.30 (m, 3H), 3.27-2.98 (M, 4H), 2.42-1.92 (m, 8H), 1.81-1.45 (m, 7H)

(2R,3S)-1-(2-fluoro-6-methylbenzoyl)-2-[4-((R)-2-trifluoromethylpyrrolidin-1-ylmethyl)phenyl]piperidine-3-carboxylic acid (3-$t$-butylphenyl)amide

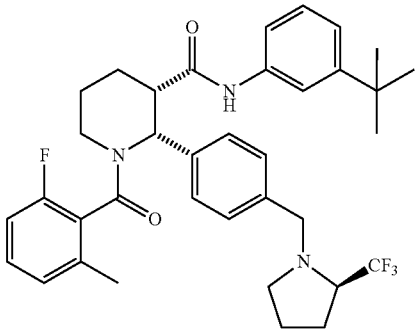

$^1$H NMR (400 MHz, CDCl$_3$) δ □8.01 (bs, 0.5H), 7.96 (bs, 0.5H), 7.55-7.37 (m, 3H), 7.30-7.19 (m, 6H), 7.13-7.06 (m, 1H), 7.01-6.90 (m, 1H), 6.85-6.64 (m, 1H), 4.15-4.11 (m, 1H), 3.58-3.54 (m, 1H), 3.30-3.20 (m, 2H), 3.17-2.80 (m, 2H), 2.45-2.17 (m, 4H), 2.00-1.94 (m, 2H), 1.86-1.60 (m, 8H), 1.31-1.26 (m, 7H)

Example 12

Materials and Methods
  A. Cells
    1. C5a Receptor Expressing Cells
    a) U937 Cells U937 cells are a monocytic cell line which express C5aR, and are available from American Tissue Cell Collection (Virginia). These cells were cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, and 10% FBS. Cells were grown under 5% CO$_2$/95% air, 100% humidity at 37° C. and subcultured twice weekly at 1:6 (cells were cultured at a density range of 1×10$^5$ to 2×10$^6$ cells/mL) and harvested at 1×10$^6$ cells/mL. Prior to assay, cells are treated overnight with 0.5 mM of cyclic AMP (Sigma, OH) and washed once prior to use. cAMP treated U937 cells can be used in C5aR ligand binding and functional assays.
    b) Isolated Human Neutrophils Optionally, human or murine neutrophils can be used to assay for compound activity. Neutrophils may be isolated from fresh human blood using density separation and centrifugation. Briefly, whole blood is incubated with equal parts 3% dextran and allowed to separate for 45 minutes. After separation, the top layer is layered on top of 15 mls of Ficoll (15 mls of Ficoll for every 30 mls of blood suspension) and centrifuged for 30 minutes at 400×g with no brake. The pellet at the bottom of the tube is then isolated and resuspended into PharmLyse RBC Lysis Buffer (BD Biosciences, San Jose, Calif.) after which the sample is again centrifuged for 10 minutes at 400×g with brake. The remaining cell pellet is resuspended as appropriate and consists of isolated neutrophils.
  B. Assays
    1. Inhibition of $^{125}$I-C5a Binding to C5aR cAMP treated U937 cells expressing C5aR were centrifuged and resuspended in assay buffer (20 mM HEPES pH 7.1, 140 mM NaCl, 1 mM CaCl$_2$, 5 mM MgCl$_2$, and with 0.1% bovine serum albumin) to a concentration of 3×10$^6$ cells/mL. Binding assays were set up as follows. 0.1 mL of cells was added to the assay plates containing 5 μL of the compound, giving a final concentration of ~2-10 μM each compound for screening (or part of a dose response for compound IC$_{50}$ determinations). Then 0.1 mL of $^{125}$I labeled C5a (obtained from Perkin Elmer Life Sciences, Boston, Mass.) diluted in assay buffer to a final concentration of ~50 μM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess C5a (1 μg/mL, for non-specific binding) were used to calculate the percent of total inhibition for compound. The computer program Prism from GraphPad, Inc. (San Diego, Ca) was used to calculate IC$_{50}$ values. IC$_{50}$ values are those concentrations required to reduce the binding of radiolabeled C5a to the receptor by 50%. (For further descriptions of ligand binding and other functional assays, see Dairaghi, et al., *J. Biol. Chem.* 274: 21569-21574 (1999), Penfold, et al., *Proc. Natl. Acad. Sci. USA.* 96:9839-9844 (1999), and Dairaghi, et al., *J. Biol. Chem.* 272:28206-28209 (1997)).
    2. Calcium Mobilization Optionally, compounds may be further assayed for their ability to inhibit calcium flux in cells. To detect the release of intracellular stores of calcium, cells (e.g., cAMP stimulated U937 or neutrophils) are incubated with 3 μM of INDO-1AM dye (Molecular Probes; Eugene, Oreg.) in cell media for 45 minutes at room temperature and washed with phosphate buffered saline (PBS). After INDO-1AM loading, the cells are resuspended in flux buffer (Hank's balanced salt solution (HBSS) and 1% FBS). Calcium mobilization is measured using a Photon Technology International spectrophotometer (Photon Technology International; New Jersey) with excitation at 350 nm and dual simultaneous recording of fluorescence emission at 400 nm and 490 nm. Relative intracellular calcium levels are expressed as the 400 nm/490 nm emission ratio. Experiments are performed at 37° C. with constant mixing in cuvettes each containing 10$^6$ cells in 2 mL of flux buffer. The chemokine ligands may be used over a range from 1 to 100 nM. The emission ratio is plotted over time (typically 2-3 minutes). Candidate ligand blocking compounds (up to 10 μM) are added at 10 seconds, followed by chemokines at 60 seconds (i.e., C5a; R&D Systems; Minneapolis, Minn.) and control chemokine (i.e., SDF-1α; R&D Systems; Minneapolis, Minn.) at 150 seconds.
    3. Chemotaxis Assays Optionally, compounds may be further assayed for their ability to inhibit chemotaxis in cells. Chemotaxis assays are performed using 5 μm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). C5aR ligands (i.e., C5a, R&D Systems; Minneapolis, Minn.) are use to evaluate compound mediated inhibition of C5aR mediated migration. Other chemokines (i.e., SDF-1α R&D Systems; Minneapolis, Minn.) are used as specificity controls. The lower chamber is loaded with 29 μl of chemokine (i.e., 0.03 nM C5a) and varying amounts of compound; the top chamber contains 100,000 U937 or neutrophil cells in 20 μl. The chambers are incubated 1.5 hours at 37° C., and the number of cells in the lower chamber quantified either by direct cell counts in five high powered fields per well or by the CyQuant assay (Molecular Probes), a fluorescent dye method that measures nucleic acid content and microscopic observation.

C. Identification of Inhibitors of C5aR

1. Assay

To evaluate small organic molecules that prevent the C5a receptor from binding ligand, an assay was employed that detected $^{125}$I-C5a binding to cells expressing C5aR on the cell surface (for example, cAMP stimulated U937 cells or isolated human neutrophils). For compounds that inhibited binding, whether competitive or not, fewer radioactive counts are observed when compared to uninhibited controls.

Equal numbers of cells were added to each well in the plate. The cells were then incubated with radiolabeled C5a. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = (1 - [(\text{sample cpm}) - (\text{nonspecific cpm})] / [(\text{total cpm}) - (\text{nonspecific cpm})]) \times 100.$$

2. Dose Response Curves

To ascertain a candidate compound's affinity for C5aR as well as confirm its ability to inhibit ligand binding, inhibitory activity was titered over a $1\times10^{-10}$ to $1\times10^{-4}$ M range of compound concentrations. In the assay, the amount of compound was varied; while cell number and ligand concentration were held constant.

D. In Vivo Efficacy Models

The compounds of interest can be evaluated for potential efficacy in treating a C5a mediated conditions by determining the efficacy of the compound in an animal model. In addition to the models described below, other suitable animal models for studying the compound of interest can be found in Mizuno, M. et al., *Expert Opin. Investig. Drugs* (2005), 14(7), 807-821, which is incorporated herein by reference in its entirety.

1. Models of C5a Induced Leukopenia a) C5a Induced Leukopenia in a Human C5aR Knock-in Mouse Model To study the efficacy of compounds of the instant invention in an animal model, a recombinant mouse can be created using standard techniques, wherein the genetic sequence coding for the mouse C5aR is replaced with sequence coding for the human C5aR, to create a hC5aR-KI mouse. In this mouse, administration of hC5a leads to upregulation of adhesion molecules on blood vessel walls which bind blood leukocytes, sequestering them from the blood stream. Animals are administered 20 ug/kg of hC5a and 1 minute later leukocytes are quantified in peripheral blood by standard techniques. Pretreatment of mice with varying doses of the present compounds can almost completely block the hC5a induced leukopenia.

b) C5a Induced Leukopenia in a Cynomolgus Monkey Model

To study the efficacy of compounds of the instant invention in a non-human primate model model, C5a induced leucopenia is studied in a cynomolgus model. In this model administration of hC5a leads to upregulation of adhesion molecules on blood vessel walls which bind blood leukocytes, hence sequestering them from the blood stream. Animals are administered 10 ug/kg of hC5a and 1 minute later leukocytes are quantified in peripheral blood.

c) Mouse Model of ANCA Induced Vasculitis

On day 0, hC5aR-KI mice are intravenously injected with 50 mg/kg purified antibody to myeloperoxidase (Xiao et al, *J. Clin. Invest.* 110: 955-963 (2002)). Mice are further dosed with oral daily doses of compounds of the invention or vehicle for seven days, then mice are sacrificed and kidneys collected for histological examination. Analysis of kidney sections can show significantly reduced number and severity of crescentic and necrotic lesions in the glomeruli when compared to vehicle treated animals.

d) Mouse Model of Choroidal Neovascularization

To study the efficacy of compounds of the instant invention in treatment of age related macular degeneration (AMD) the bruch membrane in the eyes of hC5aR-KI mice are ruptured by laser photocoagulation (Nozika et al, *PNAS* 103: 2328-2333 (2006). Mice are treated with vehicle or a daily oral or appropriate intra-vitreal dose of a compound of the invention for one to two weeks. Repair of laser induced damage and neovascularization are assessed by histology and angiography.

2. Rheumatoid Arthritis Models a) Rabbit Model of Destructive Joint Inflammation To study the effects of candidate compounds on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J. Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of candidate compound (dose 1=50 μM or dose 2=100 μM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1—minimal, 2—mild, 3—moderate, 4—moderate-marked.

b) Evaluation of a Compound in a Rat Model of Collagen Induced Arthritis

A 17 day developing type II collagen arthritis study is conducted to evaluate the effects of a candidate compound on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3): 857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A candidate compound is dosed daily in a sub-cutaneous manner from day 0 till day 17 at a efficacious dose. Caliper measurements of the ankle joint diameter were taken, and reducing joint swelling is taken as a measure of efficacy.

3. Rat Model of Sepsis

To study the effect of compounds of interest on inhibiting the generalized inflammatory response that is associated with a sepsis like disease, the Cecal Ligation and Puncture (CLP) rat model of sepsis is used. A Rat CLP study is conducted essentially as described in Fujimura N. et al. (*American Journal Respiratory Critical Care Medicine* 2000; 161: 440-446). Briefly described here, Wistar Albino Rats of both sexes weighing between 200-250 g are fasted for twelve hours prior to experiments. Animals are kept on normal 12 hour light and dark cycles and fed standard rat chow up until 12 hours prior to experiment. Then animals are split into four groups; (i) two sham operation groups and (ii) two CLP groups. Each of these two groups (i.e., (i) and (ii)) is split into vehicle control group and test compound group. Sepsis is induced by the CLP method. Under brief anesthesia a midline laparotomy is made using minimal dissection and the cecum is ligated just below the ileocaecal valve with 3-0 silk, so the intestinal continuity is maintained. The antimesinteric surface of the cecum is perforated with an 18 gauge needle at two locations 1 cm apart and the cecum is gently squeezed until fecal matter is extruded. The bowel is then returned to the abdomen and the incision is closed. At the end of the operation, all rats are resuscitated with saline, 3 ml/100 g body weight, given subcutaneously. Postoperatively, the rats are deprived of food, but have free access to water for the next 16 hours until they are sacrificed. The sham operated groups are given a laparotomy and the cecum is manipulated but not ligated or perforated. Beneficial effects of treatment are measured by histopathological scoring of tissues and organs as well as measurement of several key indicators of hepatic function, renal function, and lipid peroxidation. To test for hepatic function aspartate transaminase (AST) and alanine transaminase (ALT) are measured. Blood urea nitrogen and creatinine concentrations are studied to assess renal function. Pro-inflammatory cytokines such as TNF-alpha and IL-1beta are also assayed by ELISA for serum levels.

4. Mouse SLE Model of Experimental Lupus Nephritis.

To study the effect of compounds of interest on a Systemic Lupus Erythematosus (SLE), the MRL/lpr murine SLE model is used. The MRL/Mp-Tmfrsf6$^{lpr/lpr}$ strain (MRL/lpr) is a commonly used mouse model of human SLE. To test compounds efficacy in this model male MRL/lpr mice are equally divided between control and C5aR antagonists groups at 13 weeks of age. Then over the next 6 weeks compound or vehicle is administered to the animals via osmotic pumps to maintain coverage and minimize stress effects on the animals. Serum and urine samples are collected bi-weekly during the six weeks of disease onset and progression. In a minority of these mice glomerulosclerosis develops leading to the death of the animal from renal failure. Following mortality as an indicator of renal failure is one of the measured criteria and successful treatment will usually result in a delay in the onset of sudden death among the test groups. In addition, the presence and magnitude of renal disease may also be monitored continuously with blood urea nitrogen (BUN) and albuminuria measurements. Tissues and organs were also harvested at 19 weeks and subjected to histopathology and immunohistochemistry and scored based on tissue damage and cellular infiltration.

5. Rat Model of COPD

Smoke induced airway inflammation in rodent models may be used to assess efficacy of compounds in Chronic Obstructive Pulmonary Disease (COPD). Selective antagonists of chemokines have shown efficacy in this model (see, Stevenson, et al., *Am. J Physiol Lung Cell Mol Physiol.* 288 L514-L522, (2005)). An acute rat model of COPD is conducted as described by Stevenson et al. A compound of interest is administered either systemically via oral or IV dosing; or locally with nebulized compound. Male Sprague-Dawley rats (350-400 g) are placed in Perspex chambers and exposed to cigarette smoke drawn in via a pump (50 mL every 30 seconds with fresh air in between). Rats are exposed for a total period of 32 minutes. Rats are sacrificed up to 7 days after initial exposure. Any beneficial effects of treatment are assessed by a decrease inflammatory cell infiltrate, decreases in chemokine and cytokine levels.

In a chronic model, mice or rats are exposed to daily tobacco smoke exposures for up to 12 months. Compound is administered systemically via once daily oral dosing, or potentially locally via nebulized compound. In addition to the inflammation observed with the acute model (Stevensen et al.), animals may also exhibit other pathologies similar to that seen in human COPD such as emphysema (as indicated by increased mean linear intercept) as well as altered lung chemistry (see Martorana et al, *Am. J. Respir. Crit. Care Med.* 172(7): 848-53.

6. Mouse EAE Model of Multiple Sclerosis

Experimental autoimmune encephalomyelitis (EAE) is a model of human multiple sclerosis. Variations of the model have been published, and are well known in the field. In a typical protocol, C57BL/6 (Charles River Laboratories) mice are used for the EAE model. Mice are immunized with 200 ug myelin oligodendrocyte glycoprotein (MOG) 35-55 (Peptide International) emulsified in Complete Freund's Adjuvant (CFA) containing 4 mg/ml *Mycobacterium tuberculosis* (Sigma-Aldrich) s.c. on day 0. In addition, on day 0 and day 2 animals are given 200 ng of pertussis toxin (Calbiochem) i.v. Clinical scoring is based on a scale of 0-5: 0, no signs of disease; 1, flaccid tail; 2, hind limb weakness; 3, hind limb paralysis; 4, forelimb weakness or paralysis; 5, moribund. Dosing of the compounds of interest to be assessed can be initiated on day 0 (prophylactic) or day 7 (therapeutic, when histological evidence of disease is present but few animals are presenting clinical signs) and dosed once or more per day at concentrations appropriate for their activity and pharmacokinetic properties, e.g. 100) mg/kg s.c. Efficacy of compounds can be assessed by comparisons of severity (maximum mean clinical score in presence of compound compared to vehicle), or by measuring a decrease in the number of macrophages (F4/80 positive) isolated from spinal cords. Spinal cord mononuclear cells can be isolated via discontinuous Percoll-gradient. Cells can be stained using rat anti-mouse F4/80-PE or rat IgG2b-PE (Caltag Laboratories) and quantitated by FACS analysis using 10 ul of Polybeads per sample (Polysciences).

7. Mouse Model of Kidney Transplantation

Transplantation models can be performed in mice, for instance a model of allogenic kidney transplant from $C_{57}BL/6$ to BALB/c mice is described in Faikah Gueler et al, JASN Express, Aug. 27, 2008. Briefly, mice are anesthetized and the left donor kidney attached to a cuff of the aorta and the renal vein with a small caval cuff, and the ureters removed en block. After left nephrectomy of the recipient, the vascular cuffs are anastomosed to the recipient abdominal aorta and vena cava, respectively, below the level of the native renal vessels. The ureter is directly anastomosed into the bladder. Cold ischemia time is 60 min, and warm ischemia time is 30 min. The right native kidney can be removed at the time of allograft transplantation or at post-transplantation day 4 for long-term survival studies. General physical condition of the mice is monitored for evidence of rejection. Compound treatment of animals can be started before surgery or immediately after transplantation, eg by sub cut injection once daily. Mice are studied for renal function and survival. Serum creatinine levels are measured by an automated method (Beckman Analyzer, Krefeld, Germany).

8. Mouse Model of Ischemia/Reperfusion

A mouse model of ischemia/reperfusion injury can be performed as described by Xiufen Zheng et al, *Am. J. Pathol*, Vol 173:4, October, 2008. Briefly, CD1 mice aged 6-8 weeks are anesthetized and placed on a heating pad to maintain warmth during surgery. Following abdominal incisions, renal pedicles are bluntly dissected and a microvascular clamp placed on the left renal pedicle for 25-30 minutes. Following ischemia the clamps are removed along with the right kidney, incisions sutured, and the animals allowed to recover. Blood is collected for serum creatinine and BUN analysis as an indicator of kidney health. Alternatively animal survival is monitored over time. Compound can be administered to animals before and/or after the surgery and the effects on serum creatinine, BUN or animal survival used as indicators of compound efficacy.

9. Mouse Model of Tumor Growth

C57BL/6 mice 6-16 weeks of age are injected subcutaneously with 1×105 TC-1 cells (ATCC, VA) in the right or left rear flank. Beginning about 2 weeks after cell injection, tumors are measured with calipers every 2-4 d until the tumor size required the mice are killed. At the time of sacrifice animals are subjected to a full necropsy and spleens and tumors removed. Excised tumors are measured and weighed. Compounds may be administered before and/or after tumor injections, and a delay or inhibition of tumor growth used to assess compound efficacy.

What is claimed is:

1. A process for preparing a compound of formula (ii),

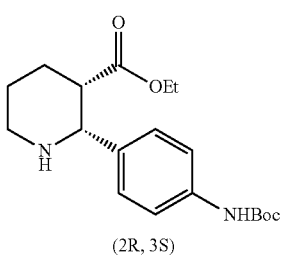

(ii)

(2R, 3S)

comprising
(a) treating a compound of formula (i)

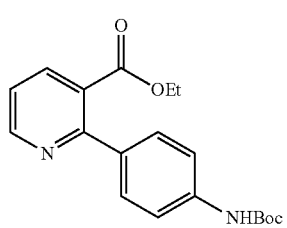

(i)

with $H_2$ and a platinum oxide catalyst under reducing conditions; and (b) subjecting the product of step (a) to resolution with di-toluoyl-L-tartaric acid to provide compound (ii).

2. A process in accordance with claim 1, wherein compound (ii) is prepared in about 97% enantiomeric excess.

3. A process in accordance with claim 1, further comprising a step wherein the compound of formula (i) is prepared by treating ethyl 2-chloronicotinate with N-Boc-4-aminophenylboronic acid in the presence of $Pd(PPh_3)_4$.

4. A process in accordance with claim 1, wherein step (a) is carried out in ethanol and HCl.

5. A process in accordance with claim 1, wherein step (b) is carried out in THF and tert-butyl methyl ether.

6. A process for preparing a compound of formula (ii),

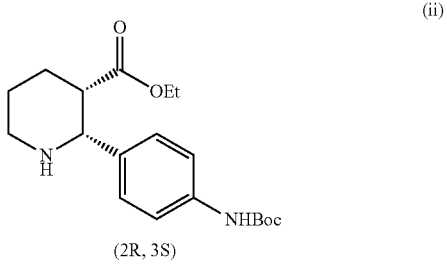 [SMILES: CCOC(=O)[C@H]1CCCN[C@H]1c1ccc(NC(=O)OC(C)(C)C)cc1]

(ii)

(2R, 3S)

comprising subjecting a compound of formula (iia)

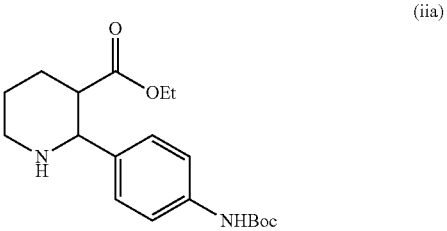 [SMILES: CCOC(=O)C1CCCNC1c1ccc(NC(=O)OC(C)(C)C)cc1]

(iia)

to resolution with di-toluoyl-L-tartaric acid to provide compound (ii).

7. A process in accordance with claim 6, wherein compound (ii) is prepared in about 97% enantiomeric excess.

8. A compound having the formula:

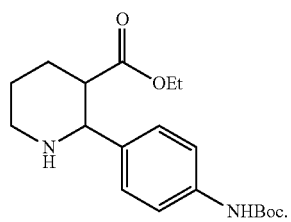 [SMILES: CCOC(=O)C1CCCNC1c1ccc(NC(=O)OC(C)(C)C)cc1]

9. A compound of claim 8, having the formula:
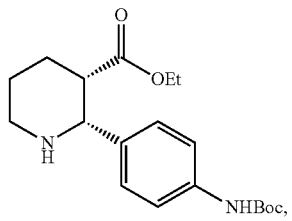
which is provided in about 97% enantiomeric excess.
10. A compound having the formula:
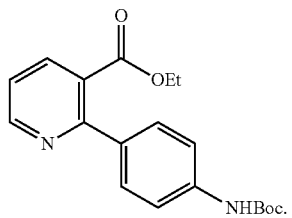 [SMILES: CCOC(=O)c1cccnc1-c1ccc(NC(=O)OC(C)(C)C)cc1]
* * * * *